United States Patent

Aissaoui et al.

(10) Patent No.: US 6,703,392 B2
(45) Date of Patent: Mar. 9, 2004

(54) 1,2,3,4-TETRAHYDROISOQUINOLINE DERIVATIVES

(75) Inventors: Hamed Aissaoui, Wittenheim (FR); Michael Cappi, München (DE); Martine Clozel, Saint-Louis (FR); Walter Fischli, Allschwil (CH); Ralf Koberstein, Lörrach (DE)

(73) Assignee: Actelion Pharmaceuticals Ltd., Allschwil (CH)

(*) Notice: Subject to any disclaimer, the term of this patent is extended or adjusted under 35 U.S.C. 154(b) by 0 days.

(21) Appl. No.: 10/239,693
(22) PCT Filed: Mar. 12, 2001
(86) PCT No.: PCT/EP01/02733
§ 371 (c)(1), (2), (4) Date: Feb. 24, 2003
(87) PCT Pub. No.: WO01/68609
PCT Pub. Date: Sep. 20, 2001

(65) Prior Publication Data
US 2003/0176415 A1 Sep. 18, 2003

(30) Foreign Application Priority Data
Mar. 14, 2000 (EP) .................. PCT/EP00/02245

(51) Int. Cl.$^7$ .................. C07D 217/04; C07D 401/02; A61K 31/47
(52) U.S. Cl. .................. 514/252.04; 546/139; 546/148; 546/149; 544/238; 544/333; 514/256; 514/307
(58) Field of Search .................. 514/252.04, 256, 514/307; 546/139, 148, 149; 544/256, 307

(56) References Cited

U.S. PATENT DOCUMENTS 3,480,714 A 11/1969 Werner

FOREIGN PATENT DOCUMENTS

| | | |
|---|---|---|
| DE | 204917 | 12/1983 |
| DE | 258817 | 8/1988 |
| DE | 261158 | 10/1988 |
| EP | 0494623 | 7/1992 |
| JP | 61 053 268 | 3/1986 |
| JP | 07 267 961 | 10/1995 |
| JP | 10 095 766 | 4/1998 |
| WO | WO 9823593 | 6/1998 |
| WO | WO 99/09024 | 2/1999 |
| WO | WO 99/58533 | 11/1999 |
| WO | WO 00/29399 | 5/2000 |
| WO | WO 00/35882 | 6/2000 |
| WO | WO 00/78742 | 12/2000 |
| WO | WO 00/78744 | 12/2000 |
| WO | WO 01/02368 | 1/2001 |

OTHER PUBLICATIONS

Chemical Abstracts vol. 110, No. 19, Abstract No. 173523 (May 8, 1989), Columbus, Ohio.
Chemelli et al. Narcolepsy in orexin knockout mice: molecular genetics of sleep regulation. Cell. Aug. 20, 1999;98(4):437–51.

Corrodi & Hardegger, Helv. Chim. Acta, 1956 39:889–897 (in German, English abstract not available).

Hazebroucq, G. 2,3,4,5-tetrahydro-1H-3-benzazepin-1-ones and hexahydroimidazoisoquinolines. Ann. Chim. (Paris) 1966 1(5/6):221–54 (in French, English abstract not available).

J. March (4$^{th}$ Ed) *Advanced Organic Chemistry*. Wiley-Interscience publication, p. 1042, No Date Given.

Chemical Abstracts vol. 109, No. 9, Abstract No. 170679 (Nov. 7, 1988), Columbus, Ohio.

Chemical Abstracts vol. 110, No. 1, Abstract No. 459 (Jan. 2, 1989), Columbus, Ohio.

Lukevics et al. Silyl modification of biologically active compounds. 4. Derivatives of amino acids in the tetrahydroquinoline, tetrahydroisoquinoline, and tetrahydrosilaisoquinoline series. Chem. Heterocycl. Compd. (N.Y.) 1997 33(2):234–238.

Chemical Abstracts vol. 110, No. 23, Abstract No. 205079 (Jun. 5, 1989), Columbus, Ohio.

Sakurai et al. Orexins and orexin receptors: a family of hypothalamic neuropeptides and G protein-coupled receptors that regulate feeding behavior. Cell. Feb. 20, 1998;92(4):573–85.

Vaccaro et al. Inhibitors of acyl CoA:cholesterol acyltransferase, J Med Chem. 1996 Apr 12;39(8):1704–19.

Hori M. et al. Benzaza cycloalkane derivatives. IV, 16:68–71 (in Japanese with English summary), No Date Given.

Kempter G. et al. Synthesis of heteroanalogs of piperidinoacetanilides. Wiss. Z.—Martin–Luther–Univ. Halle–Wittenberg, Math.–Naturwiss. Reihe 1983, 32(5):3–25 (an English Abstract is included herewith).

Primary Examiner—Zinna Northington Davis
(74) Attorney, Agent, or Firm—Jones Day

(57) ABSTRACT

The invention relates to novel 1,2,3,4-tetrahydroisochinoline derivatives of formula (I) and their use as active ingredients in the preparation of pharmaceutical compositions. The invention also concerns related aspects including processes for the preparation of the compounds, pharmaceutical compositions containing one or more of those compounds and especially their use as orexin receptor antagonists.

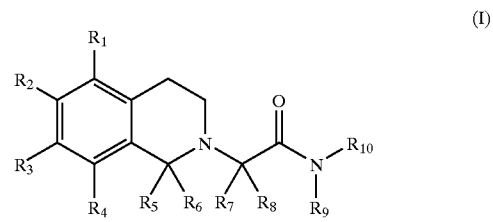

(I)

22 Claims, No Drawings

1,2,3,4-TETRAHYDROISOQUINOLINE DERIVATIVES

This is a national stage application of International Application PCT/EP01/02733, filed Mar. 12, 2001, which was published under PCT Article 21(2) as PCT Publication No. WO 01/68609 in English, and which claims the benefit of International Application PCT/EP00/02245 filed Mar. 14, 2000. Both International Applications PCT/EP01/02733 and PCT/EP00/02245 are hereby incorporated by reference in their entireties.

The present invention relates to novel 1,2,3,4-tetrahydroisoquinoline derivatives of the general formula I and their use as pharmaceuticals. The invention also concerns related aspects including processes for the preparation of the compounds, pharmaceutical compositions containing one or more compounds of formula I, and especially their use as orexin receptor antagonists.

The orexins (hypocretins) comprise two neuropeptides produced in the hypothalamus: the orexin A (OX-A) (a 33 aminoacid peptide) and the orexin B (OX-B) (a 28 aminoacid peptide) (Sakurai T. et al., Cell, 1998, 92, 573–585). Orexins are found to stimulate food consumption in rats suggesting a physiological role for these peptides as mediators in the central feedback mechanism that regulates feeding behavior (Sakurai T. et al., Cell, 1998, 92, 573–585). On the other hand, it was also proposed that orexins regulate states of sleep and wakefulness opening potentially novel therapeutic approaches for narcoleptic patients (Chemelli R. M. et al., Cell, 1999, 98, 437–451). Two orexin receptors have been cloned and characterized in mammals which belong to the G-protein coupled receptor superfamily (Sakurai T. et al., Cell, 1998, 92, 573–585), the orexin-1 receptor ($OX_1$) which is selective for OX-A and the orexin-2 receptor ($OX_2$) which is capable to bind OX-A as well as OX-B.

Orexin receptors are found in the mammalian host and may be responsible for many biological functions such as pathologies including, but not limited to, depression; anxiety; addictions; obsessive compulsive disorder; affective neurosis; depressive neurosis; anxiety neurosis; dysthymic disorder; behaviour disorder; mood disorder; sexual dysfunction; psychosexual dysfunction; sex disorder; schizophrenia; manic depression; delerium; dementia; severe mental retardation and dyskinesias such as Huntington's disease and Tourette syndrome; feeding disorders such as anorexia, bulimia, cachexia and obesity; diabetes; appetite/taste disorders; vomiting/nausea; asthma; cancer; Parkinson's disease; Cushing's syndrome/disease; basophil adenoma; prolactinoma; hyperprolactinemia; hypopituitarism; hypophysis tumor/adenoma; hypothalamic diseases; inflammatory bowel disease; gastric diskinesia; gastric ulcus; Froehlich's syndrome; adrenohypophysis disease; hypophysis disease; pituitary growth hormone; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; disturbed biological and circadian rhythms; sleep disturbances associated with deseases such as neurological disorders, neuropathic pain and restless leg syndrome; heat and lung diseases, acute and congestive heart failure; hypotension; hypertension; urinary retention; osteoporosis; angina pectoris; myocardinal infarction; ischaemic or haemorrhagic stroke; subarachnoid haemorrhage; ulcers; allergies; benign prostatic hypertrophy; chronic renal failure; renal disease; impaired glucose tolerance; migraine; hyperalgesia; pain; enhanced or exaggerated sensitivity to pain such as hyperalgesia, causalgia, and allodynia; acute pain; burn pain; a typical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; conditions associated with visceral pain such as irritable bowel syndrome, migraine and angina; urinary bladder incontinence e.g. urge incontinence; tolerance to narcotics or withdrawal from narcotics; sleep disorders; sleep apnea; narcolepsy; insomnia; parasomnia; jet-lag syndrome; and neurodegerative disorders including nosological entities such as disinhibition-dementia-parkinsonism-amyotrophy complex; pallido-ponto-nigral degeneration epilepsy; seizure disorders and other diseases related to orexin.

The present invention provides 1,2,3,4-tetrahydroisoquinoline derivatives which are non-peptide antagonists of human orexin receptors, in particular $OX_1$ receptors. In particular, these compounds are of potential use in the treatment of obesity and/or sleep disorders.

So far not much is known about low molecular weight compounds which have a potential to antagonise either specifically $OX_1$ or $OX_2$ or both receptors at the same time. Recently WO 9909024 has been published wherein phenylurea and phenylthiourea derivatives as $OX_1$ antagonists are disclosed. Also quite recently WO 9958533 has been published disclosing the same type of compounds which are again described as being preferably $OX_1$ receptor antagonists. The novel compounds of the present invention belong to an entirely different class of low molecular weight compounds as compared to all prior art orexin receptor antagonists so far published.

The present invention relates to novel 1,2,3,4-tetrahydroisoquinoline derivatives of the general formula (I).

Formula (I)

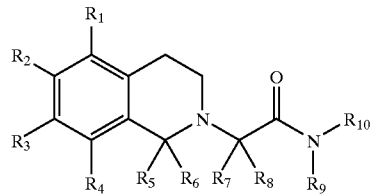

wherein:

$R^1$, $R^2$, $R^3$, $R^4$ independently represent cyano, nitro, halogen, hydrogen, hydroxy, lower alkyl, lower alkenyl, lower alkoxy, lower alkenyloxy, trifluoromethyl, trifluoromethoxy, cycloalkyloxy, aryloxy, aralkyloxy, heterocyclyloxy, heterocyclylalkyloxy, $R^{11}CO—$, $NR^{12}R^{13}CO—$, $R^{12}R^{13}N—$, $R^{11}OOC—$, $R^{11}SO_2NH—$ or $R^{14}—CO—NH—$ or $R^2$ and $R^3$ together as well as $R^1$ and $R^2$ together and $R^3$ and $R^4$ together may form with the phenyl ring a five, six or seven-membered ring containing one or two oxygen atoms;

$R^5$, $R^6$, $R^7$, $R^8$, $R^9$, $R^{10}$ independently represent hydrogen, aryl, aralkyl, lower alkyl, lower alkenyl, trifluoromethyl, cycloalkyl, heterocyclyl or heterocyclyl-lower alkyl;

$R^{11}$ represents lower alkyl, aryl, aralkyl, heterocyclyl or heterocyclyl-lower alkyl;

$R^{12}$ and $R^{13}$ independently represent hydrogen, alkyl, cycloalkyl, aryl, aralkyl, heterocyclyl or heterocyclyl-lower alkyl;

$R^{14}$ represents alkyl, aryl, cycloalkyl, heterocyclyl, $R^{12}R^{13}N$— or $R^{11}O$—.

The compounds of formula I can contain one or more asymmetric centres and can be present in the form of optically pure enantiomers, mixtures of enantiomers such as, for example, racemates, optically pure diastereoisomers, mixtures of diastereoisomers, diastereoisomeric racemates, mixture of diastereoisomeric racemates, or meso forms and pharmaceutically acceptable salts thereof.

In the present description the term "lower alkyl", alone or in combination, signifies a straight-chain or branched-chain alkyl group with 1 to 8 carbon atoms, preferably a straight or branched-chain alkyl group with 1–5 carbon atoms. Examples of straight-chain and branched $C_1$–$C_8$ alkyl groups are methyl, ethyl, propyl, isopropyl, butyl, pentyl, hexyl, heptyl, octyl, isobutyl tert-butyl, the isomeric pentyls, the isomeric hexyls, the isomeric heptyls and the isomeric octyls, preferably methyl, ethyl, propyl, isopropyl, butyl, 2-butyl, tert-butyl and pentyl.

The term "lower alkenyl", alone or in combination, signifies a straight-chain or branched-chain alkenyl group with 2 to 5 carbon atoms, preferably allyl and vinyl.

The term "lower alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert-butoxy, preferably methoxy and ethoxy.

Lower alkenyloxy groups are preferably vinyloxy and allyloxy.

The term "cycloalkyl", alone or in combination, signifies a cycloalkyl ring with 3 to 8 carbon atoms and preferably a cycloalkyl ring with 3 to 6 carbon atoms. Examples of $C_3$–$C_8$ cycloalkyl are cyclopropyl, cyclobutyl, cyclopentyl, cyclohexyl, cycloheptyl and cyclooctyl, preferably cyclopropyl, cyclohexyl and particularly cyclohexyl or lower alkyl substituted cycloalkyl which may preferably be substituted with lower alkyl such as methyl-cyclopropyl, dimethyl-cyclopropyl, methyl-cyclobutyl, methyl-cyclopentyl, methyl-cyclohexyl, dimethyl-cyclohexyl, The term "aryl", alone or in combination, signifies a phenyl or naphthyl group which optionally carries one or more substituents, preferably one or two substituents, each independently selected from cyano, halogen, hydroxy, lower alkyl, lower alkenyl, lower alkoxy, lower alkenyloxy, nitro, trifluoromethyl, trifluoromethoxy, amino, carboxy and the like, such as phenyl, p-tolyl, 4-methoxyphenyl, 4-tert-butoxyphenyl 4-fluorophenyl, 2-chlorophenyl, 4-hydroxyphenyl, 1-naphthyl and 2-naphthyl. Preferred are carboxyphenyl, lower alkoxy-phenyl, hydroxyphenyl and particularly phenyl.

The term "aralkyl", alone or in combination, signifies an alkyl or cycloalkyl group as previously defined in which one hydrogen atom has been replaced by an aryl group as previously defined. Preferred are benzyl and benzyl substituted in the phenyl ring with hydroxy, lower alkyl, lower alkoxy or halogen preferably chlorine. Particularly preferred is benzyl.

For the term "heterocyclyl" and "heterocyclyl-lower alkyl", the heterocyclyl group is preferably a 5- to 10-membered monocyclic or bicyclic ring, which may be saturated, partially unsaturated or aromatic containing for example 1, 2 or 3 heteroatoms selected from oxygen, nitrogen and sulphur which may be the same or different. Example of such heterocyclyl groups are pyrrolidinyl, piperidinyl, piperazinyl, morpholinyl, pyridyl pyrimidinyl, pyrazinyl, pyridazinyl, quinolyl, isoquinolyl, thienyl, thiazolyl, isothiazolyl, furyl, imidazoyl, pyrazolyl, pyrrolyl, indazolyl, indolyl, isoindolyl, isoxazolyl, oxazolyl, quinoxalinyl, phthalazinyl, cinnolinyl, dihydropyrrolyl, pyrrolidinyl, isobenzofuranyl, tetrahydrofuranyl, dihydropyranyl. The heterocyclyl group may have up to 5, preferably 1, 2 or 3 optional substituents. Examples of suitable substituents include halogen, lower allyl, amino, nitro, cyano, hydroxy, lower alkoxy, carboxy and lower alkyloxy-carbonyls.

The term "halogen" signifies fluorine, chlorine, bromine or iodine and preferably chlorine and bromine and particularly chlorine.

The term "carboxy", alone or in combination, signifies a —COOH group.

A group of preferred compounds according to the present invention are compounds of formula (I) wherein $R^2$, $R^3$, $R^6$, $R^7$, $R^8$ and $R^9$ are hydrogen. Examples of preferred compounds are:

2-[1-(3,4-Dimethoxy-benzyl)-5,8-dimethoxy-3,4-dihydro-1H-isoquinolin-2-yl]-N-(pyridin-2-yl-methyl)-acetamide:

2-[1-(3,4-dimethoxy-benzyl)-8-(cyclopropyl-methoxy)-5-methoxy-3,4-dihydro-1H-isoquinolin-2-yl]-N-(pyridin-2-yl-methyl)-acetamide:

2-[1-(3,4-dimethoxy-benzyl)-8-(2-fluoro-ethoxy)-5-methoxy-3,4-dihydro-1H-isoquinolin-2-yl]-N-(pyridin-2-yl-methyl)-acetamide:

2-[1-(3,4-dimethoxy-benzyl)-8-(2,2-difluoro-ethoxy)-5-methoxy-3,4-dihydro-1H-isoquinolin-2-yl]-N-(pyridin-2-yl-methyl)-acetamide:

2-[1-(3,4-dimethoxy-benzyl)-8-ethoxy-5-methoxy-3,4-dihydro-1H-isoquinolin-2-yl]-N-(pyridin-2-yl-methyl)-acetamide:

2-[1-(3,4-dimethoxy-benzyl)-8-propoxy-5-methoxy-3,4-dihydro-1H-isoquinolin-2-yl]-N-(pyridin-2-yl-methyl)-acetamide:

2-[1-(3,4-dimethoxy-benzyl)-8-allyloxy-5-methoxy-3,4-dihydro-1H-isoquinolin-2-yl]-N-(pyridin-2-yl-methyl)-acetamide:

2-[1-(3,4-dimethoxy-benzyl)-8-isopropoxy-5-methoxy-3,4-dihydro-1H-isoquinolin-2-yl]-N-(pyridin-2-yl-methyl)-acetamide:

2-[1-(3,4-dimethoxy-benzyl)-5-propoxy-8-methoxy-3,4-dihydro-1H-isoquinolin-2-yl]-N-(pyridin-2-yl-methyl)-acetamide:

Another group of preferred compounds according to the present invention are compounds of formula (II)

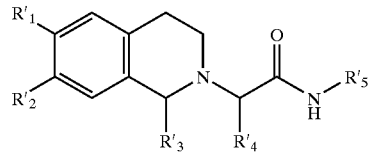

General formula II wherein:

$R'^1$ and $R'^2$ independently represent hydrogen, hydroxy, alkoxy, heteroaryloxy, carbamoyloxy or halogen or may form with the phenyl ring a five, six or seven membered-ring containing one or two oxygen atoms, $R^{r3}$, $R^{r4}$, $R^{r5}$ independently represent aryl, aralkyl, lower alkyl, lower alkenyl trifluoromethyl, cycloallyl, heterocyclyl or heterocyclyl-lower alkyl.

The compounds of formula (II) can contain one or more asymmetric centres and can be present in the form of optically pure enantiomers, mixtures of enantiomers such as, for example, racemates, optically pure diastereoisomers, mixtures of diastereoisomers, diastereoisomeric racemates, mixture of diastereoisomeric racemates, or meso forms and pharmaceutically acceptable salts thereof Examples of preferred compounds of formula (II) are:

2-[1-(3,4-Dimethoxy-benzyl)-6,7-dimethoxy-3,4-dihydro-1H-isoquinolin-2-yl]-N-benzyl-acetamide
2-[1-(3,4-Dimethoxy-benzyl)-6,7-dimethoxy-3,4-dihydro-1H-isoquinolin-2-yl]-N-naphthalen-1-ylmethyl-acetamide
2-[1-(3,4-Dimethoxy-benzyl)-6,7-dimethoxy-3,4-dihydro-1H-isoquinolin-2-yl]-N-(2-methoxy-benzyl)-acetamide
2-[1-(3,4-Dimethoxy-benzyl)-6,7-dimethoxy-3,4-dihydro-1H-isoquinolin-2-yl]-N-(4-fluoro-benzyl)-acetamide
2-[1-(3,4-Dimethoxy-benzyl)-6,7-dimethoxy-3,4-dihydro-1H-isoquinolin-2-yl]-N-(6-methoxy-naphthalen-2-ylmethyl)-acetamide
2-[1-(3,4-Dimethoxy-benzyl)-6,7-dimethoxy-3,4-dihydro-1H-isoquinolin-2-yl]-N-(4-methoxy-naphthalen-2-ylmethyl)-acetamide
2-[1-(3,4-Dimethoxy-benzyl)-6,7-dimethoxy-3,4-dihydro-1H-isoquinolin-2-yl]-N-(3,6)-difluoro-benzyl)-acetamide
2-[1-(3,4-Dimethoxy-benzyl)-6,7-dimethoxy-3,4-dihydro-1H-isoquinolin-2-yl]-N-(1-phenyl-ethyl)-acetamide
2-[1-(3,4-Dimethoxy-benzyl)-6,7-dimethoxy-3,4-dihydro-1H-isoquinolin-2-yl]-N-(pyridin-3-ylmethyl)-acetamide
2-[1-(3,4-Dimethoxy-benzyl)-6,7-dimethoxy-3,4-dihydro-1H-isoquinolin-2-yl]-N-(2-methyl-benzyl)-acetamide
2-[1-(3,4-Dimethoxy-benzyl)-6,7-dimethoxy-3,4-dihydro-1H-isoquinolin-2-yl]-N-(3-methyl-benzyl)-acetamide
2-[1-(3,4-Dimethoxy-benzyl)-6,7-dimethoxy-3,4-dihydro-1H-isoquinolin-2-yl]-N-(indan-1-yl)-acetamide
2-[1-(3,4-Dimethoxy-benzyl)-6,7-dimethoxy-3,4-dihydro-1H-isoquinolin-2-yl]-N-(1,2,3,4-tetrahydro-naphthalen-1-yl)-acetamide
2-[1-(3,4-dimethoxy-benzyl)-6-methoxy-7-(pyrazin-2-yloxy)-3,4-dihydro-1H-isoquinolin-2-yl]-N-(indan-1-yl)-acetamide
2-[1-(3,4-dimethoxy-benzyl)-6-methoxy-7-(thiazol-2-yloxy)-3,4-dihydro-1H-isoquinolin-2-yl]-N-(indan-1-yl)-acetamide
2-[1-(3,4-Dimethoxy-benzyl)-6-methoxy-7-isopropoxy-3,4-dihydro-1H-isoquinolin-2-yl]-N-(5-methoxy-indan-1-yl)-acetamide
2-[1-(3,4-Dimethoxy-benzyl)-6-methoxy-7-isopropoxy-3,4-dihydro-1H-isoquinolin-2-yl]-N-(6-methoxy-indan-1-yl)-acetamide
2-[1-(3,4-Dimethoxy-benzyl)-6-methoxy-7-isopropoxy-3,4-dihydro-1H-isoquinolin-2-yl]-N-(6-methyl-indan-1-yl)-acetamide
2-[1-(3,4-Dimethoxy-benzyl)-6-methoxy-7-isopropoxy-3,4-dihydro-1H-isoquinolin-2-yl]-N-(2-methyl-1,2,3,4-tetrahydronaphthalen-1-yl)-acetamide
2-[1-(3,4-Dimethoxy-benzyl)-6-methoxy-7-isopropoxy-3,4-dihydro-1H-isoquinolin-2-yl]-N-(4-methyl-indan-1-yl)-acetamide
2-[1-(3,4-Dimethoxy-benzyl-6,7-dimethoxy-3,4-dihydro-1H-isoquinolin-2-yl]-N-(6-methoxy-indan-1-yl)-acetamide
2-[1-(3,4-Dimethoxy-benzyl)-6,7-dimethoxy-3,4-dihydro-1H-isoquinolin-2-yl]-N-(6-methyl-indan-1-yl)-acetamide
2-{-[4-(pyrimidin-2-yloxy)-3-methoxy-benzyl]-6,7-dimethoxy-3,4-dihydro-1H-isoquinolin-2-yl}-N-benzyl-acetamide
2-[1-(3,4-dimethoxy-benzyl)-6-methoxy-7-(N,N-dimethylcarbamoyloxy)-3,4-dihydro-1H-isoquinolin-2-yl]-N-(indan-1-yl)-acetamide
2-[1-(3,4-dimethoxy-benzyl)-7-(3-fluoro-propoxy)-6-methoxy-3,4-dihydro-1H-isoquinolin-2-yl]-N-(indan-1-yl)-acetamide
2-[1-(3,4-dimethoxy-benzyl)-7-(2-fluoro-ethoxy)-6-methoxy-3,4-dihydro-1H-isoquinolin-2-yl]-N-(indan-1-yl)-acetamide
2-[1-(3,4-dimethoxy-benzyl)-7-(2,2-difluoro-ethoxy)-6-methoxy-3,4-dihydro-1H-isoquinolin-2-yl]-N-(indan-1-yl)-acetamide
2-[1-(3,4-dimethoxy-benzyl)-7-(but-2-oxy)-6-methoxy-3,4-dihydro-1H-isoquinolin-2-yl]-N-(indan-1-yl)-acetamide
2-[1-(3,4-dimethoxy-benzyl)-7-(cyclopropyl-methoxy)-6-methoxy-3,4-dihydro-1H-isoquinolin-2-yl]-N-(indan-1-yl)-acetamide
2-[1-(3,4-dimethoxy-benzyl)-7-ethoxy-6-methoxy-3,4-dihydro-1H-isoquinolin-2-yl]-N-(indan-1-yl)-acetamide
2-[1-(3,4-dimethoxy-benzyl)-7-propoxy-6-methoxy-3,4-dihydro-1H-isoquinolin-2-yl]-N-(indan-1-yl)-acetamide
2-[1-(3,4-dimethoxy-benzyl)-7-allyloxy-6-methoxy-3,4-dihydro-1H-isoquinolin-2-yl]-N-(indan-1-yl)-acetamide
2-[1-(3,4-dimethoxy-benzyl)-7-isopropoxy-6-methoxy-3,4-dihydro-1H-isoquinolin-2-yl]-N-(indan-1-yl)-acetamide
2-[1-(3,4-dimethoxy-benzyl)-7-(1-methyl-prop-2-oxy)-6-methoxy-3,4-dihydro-1H-isoquinolin-2-yl]-N-benzyl-acetamide
2-[1-(3,4-Dimethoxy-benzyl)-6-methoxy-7-isopropoxy-3,4-dihydro-1H-isoquinolin-2-yl]-N-[(1S)-indan-1-yl]-acetamide
2-[1-(3,4-Dimethoxy-benzyl)-6-methoxy-7-isopropoxy-3,4-dihydro-1H-isoquinolin-2-yl]-N-benzyl-acetamide
2-[(1S)-1-(3,4-Dimethoxy-benzyl)-6,7-dimethoxy-3,4-dihydro-1H-isoquinolin 2-yl]-N-[(1S)-indan-1-yl]-acetamide
2-[1-(3,4-dimethoxy-benzyl)-7-ethoxy-6-methoxy-3,4-dihydro-1H-isoquinolin-2-yl]-N-benzyl-acetamide
2-[1-(3,4-dimethoxy-benzyl)-7-propoxy-6-methoxy-3,4-dihydro-1H-isoquinolin-2-yl]-N-benzyl-acetamide
2-[1-(3,4-dimethoxy-benzyl)-7-allyloxy-6-methoxy-3,4-dihydro-1H-isoquinolin-2-yl]-N-benzyl-acetamide
N-benzyl-2-[1-(3,4-Dimethyl-benzyl)-6,7-dimethoxy-3,4-dihydro-1H-isoquinolin-2-yl]-acetamide
2-[1-(3,4-Dimethyl-benzyl)-6,7-dimethoxy-3,4-dihydro-1H-isoquinolin-2-yl]-N-[(1S)-indan-1-yl]-acetamide
N-benzyl-2-[-(3,4-Diethyl-benzyl)-6,7-dimethoxy-3,4-dihydro-H-isoquinolin-2-yl]-acetamide
2-[1-(3,4-Diethyl-benzyl)-6,7-dimethoxy-3,4-dihydro-1H-isoquinolin-2-yl]-N-(pyridin-2-yl-methyl)-acetamide
2-[1-(3,4-Diethyl-benzyl)-6,7-dimethoxy-3,4-dihydro-1H-isoquinolin-2-yl]-N-(pyridin-3-yl-methyl)-acetamide
2-[1-(3,4-Diethyl-benzyl)-6,7-dimethoxy-3,4-dihydro-1H-isoquinolin-2-yl]-N-(pyridin-4-yl-methyl)-acetamide
2-[1-(3,4-Dichloro-benzyl)-6,7-dimethoxy-3,4-dihydro-1H-isoquinolin-2-yl]-N-(pyridin-3-yl-methyl)-acetamide Examples of particularly preferred compounds of formula (II) are:

2-[1-(3,4-Dimethoxy-benzyl)-6,7-dimethoxy-3,4-dihydro-1H-isoquinolin-2-yl]-N-benzyl-acetamide
2-[1-(3,4-Dimethoxy-benzyl)-6,7-dimethoxy-3,4-dihydro-1H-isoquinolin-2-yl]-N-naphthalen-1-ylmethyl-acetamide 2-[1-(3,4-Dimethoxy-benzyl)-6,7-dimethoxy-3,4-dihydro-1H-isoquinolin-2-yl]-N-(indan-1-yl)-acetamide 2-[1-(3,4-Dimethoxy-benzyl)-6,7-dimethoxy-3,4-dihydro-1H-isoquinolin-2-yl]-N-(1,2,3,4-tetrahydro-naphthalen-1-yl)-acetamide 2-[1-(3,4-dimethoxy-benzyl)-6-methoxy-7-pyrazin-2-yloxy)-3,4-dihydro-1H-isoquinolin-2-yl]-N-(indan-1-yl)-acetamide 2-[1-(3,4-dimethoxy-benzyl)-6-methoxy-7-(thiazol-2-yloxy)-3,4-dihydro-1H-isoquinolin-2-yl]-N-(indan-1-yl)-acetamide 2-[1-(3,4-Dimethoxy-benzyl)-6-methoxy-7-isopropoxy-3,4-dihydro-1H-isoquinolin-2-yl]-N-(5-methoxy-indan-1-yl)-acetamide 2-[1-(3,4-Dimethoxy-benzyl)-6-methoxy-7-isopropoxy-3,4-dihydro-1H-isoquinolin-2-yl]-N-(6-methoxy-indan-1-yl)-acetamide 2-[1-(3,4-Dimethoxy-benzyl)-6-methoxy-7-isopropoxy-3,4-dihydro-1H-isoquinolin-2-yl]-N-(6-methyl-indan-1-yl)-acetamide 2-[1-(3,4-Dimethoxy-benzyl)-6-methoxy-7-isopropoxy-3,4-dihydro-1H-isoquinolin-2-yl]-N-(2-methyl-1,2,3,4-tetrahydronaphthalen-1-yl)-acetamide 2-[1-(3,4-Dimethoxy-benzyl)-6-methoxy-7-isopropoxy-3,4-dihydro-1H-isoquinolin-2-yl]-N-(4-methyl-indan-1-yl)-acetamide 2-[1-(3,4-Dimethoxy-benzyl)-6,7-dimethoxy-3,4-dihydro-1H-isoquinolin-2-yl]-N-(6-methoxy-indan-1-yl)-acetamide 2-[1-(3,4-Dimethoxy-benzyl)-6,7-dimethoxy-3,4-dihydro-1H-isoquinolin-2-yl]-N-(6-methyl-indan-1-yl)-acetamide 2-{1-[4-(pyrimidin-2-yloxy)-3-methoxy-benzyl]-6,7-dimethoxy-3,4-dihydro-1H-isoquinolin-2-yl}-N-benzyl-acetamide 2-[1-(3,4-dimethoxy-benzyl)-6-methoxy-7-(N,N-dimethylcarbamoyloxy)-3,4-dihydro-1H-isoquinolin-2-yl]-N-(indan-1-yl)-acetamide 2-[1-(3,4-dimethoxy-benzyl)-7-(3-fluoro-propoxy)-6-methoxy-3,4-dihydro-1H-isoquinolin-2-yl]-N-(indan-1-yl)-acetamide 2-[1-(3,4-dimethoxy-benzyl)-7-(2-fluoro-ethoxy)-6-methoxy-3,4-dihydro-1H-isoquinolin-2-yl]-N-(indan-1-yl)-acetamide 2-[1-(3,4-dimethoxy-benzyl)-7-(2,2-difluoro-ethoxy)-6-methoxy-3,4-dihydro-1H-isoquinolin-2-yl]-N-(indan-1-yl)-acetamide 2-[1-(3,4-dimethoxy-benzyl)-7-(but-2-oxy)-6-methoxy-3,4-dihydro-1H-isoquinolin-2-yl]-N-(indan-1-yl)-acetamide 2-[1-(3,4-dimethoxy-benzyl)-7-(cyclopropyl-methoxy)-6-methoxy-3,4-dihydro-1H-isoquinolin-2-yl]-N-(indan-1-yl)-acetamide 2-[1-(3,4-dimethoxy-benzyl)-7-ethoxy-6-methoxy-3,4-dihydro-1H-isoquinolin-2-yl]-N-(indan-1-yl)-acetamide 2-[1-(3,4-dimethoxy-benzyl)-7-propoxy-6-methoxy-3,4-dihydro-1H-isoquinolin-2-yl]-N-(indan-1-yl)-acetamide 2-[1-(3,4-dimethoxy-benzyl)-7-allyloxy-6-methoxy-3,4-dihydro-1H-isoquinolin-2-yl]-N-(indan-1-yl)-acetamide 2-[1-(3,4-dimethoxy-benzyl)-7-isopropoxy-6-methoxy-3,4-dihydro-1H-isoquinolin-2-yl]-N-(indan-1-yl)-acetamide 2-[1-(3,4-dimethoxy-benzyl)-7-(1-methyl-prop-2-oxy)-6-methoxy-3,4-dihydro-1H-isoquinolin-2-yl]-N-benzyl-acetamide 2-[1-(3,4-Dimethoxy-benzyl)-6-methoxy-7-isopropoxy-3,4-dihydro-1H-isoquinolin-2-yl]-N-[(1S)-indan-1-yl]-acetamide 2-[1-(3,4-Dimethoxy-benzyl)-6-methoxy-7-isopropoxy-3,4-dihydro-1H-isoquinolin-2-yl]-N-benzyl-acetamide 2-[(1S)-1-(3,4-Dimethoxy-benzyl)-6,7-dimethoxy-3,4-dihydro-1H-isoquinolin-2-yl]-N-[(1S)-indan-1-yl]-acetamide 2-[1-(3,4-dimethoxy-benzyl)-7-ethoxy-6-methoxy-3,4-dihydro-1H-isoquinolin-2-yl]-N-benzyl-acetamide 2-[1-(3,4-dimethoxy-benzyl)-7-propoxy-6-methoxy-3,4-dihydro-1H-isoquinolin-2-yl]-N-benzyl-acetamide 2-[1-(3,4-dimethoxy-benzyl)-7-allyloxy-6-methoxy-3,4-dihydro-1H-isoquinolin-2-yl]-N-benzyl-acetamide N-benzyl-2-[1-(3,4-Dimethyl-benzyl)-6,7-dimethoxy-3,4-dihydro-1H-isoquinolin-2-yl]-acetamide 2-[1-(3,4-Dimethyl-benzyl)-6,7-dimethoxy-3,4-dihydro-1H-isoquinolin-2-yl]-N-[(1S)-indan-1-yl]-acetamide N-benzyl-2-[1-(3,4-Diethyl-benzyl)-6,7-dimethoxy-3,4-dihydro-1H-isoquinolin-2-yl]-acetamide 2-[1-(3,4-Diethyl-benzyl)-6,7-dimethoxy-3,4-dihydro-1H-isoquinolin-2-yl]-N-(pyridin-2-yl-methyl)-acetamide 2-[1-(3,4-Diethyl-benzyl)-6,7-dimethoxy-3,4-dihydro-1H-isoquinolin-2-yl]-N-(pyridin-3-yl-methyl)-acetamide 2-[1-(3,4-Diethyl-benzyl)-6,7-dimethoxy-3,4-dihydro-1H-isoquinolin-2-yl]-N-(pyridin-4-yl-methyl)-acetamide 2-[1-(3,4-Dichloro-benzyl)-6,7-dimethoxy-3,4-dihydro-1H-isoquinolin-2-yl]-N-(pyridin-3-yl-methyl)-acetamide Examples of physiologically usable or pharmaceutically acceptable salts of the compounds of formula (I) are salts with physiologically compatible mineral acids such as hydrochloric acid, sulphuric or phosphoric acid; or with organic acids such as methanesulphonic acid, acetic acid, trifluoroacetic acid, citric acid, fumaric acid, maleic acid, tartaric acid, succinic acid or salicylic acid. The compounds of formula (I) with free carboxy groups can also form salts with physiologically compatible bases.

Examples of such salts are alkali metal, alkali earth metal, ammonium and alkylammoniumsalts such as Na, K, Ca or tetraalkylammonium salt. The compounds of formula (I) can also be present in the form of a zwitterion.

The compounds of formula (I) can contain several asymmetric centres and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates and the meso-forms.

Preferred compounds as described above have $IC_{50}$ values below 1000 nM; especially preferred compounds have $IC_{50}$ values below 100 nM which have been determinated with the FLIPR (Fluorometric Imaging Plates Reader) method described in the beginning of the experimental section.

The compounds of the general formula (I) and their pharmaceutically usable salts can be used for the treatment of diseases or disorders where an antagonist of a human orexin receptor is required such as obesity, diabetes, prolactinoma, narcolepsy, insomnia, sleep apnea, parasomnia, depression; anxiety, addictions, schizophrenia and dementia.

The compounds of formula (I) and their pharmaceutically usable salts are particularly useful for the treatment of obesity and sleep disorders.

The compounds of formula (I) and their pharmaceutically usable salts can be used as medicament (e.g. in the form of pharmaceutical preparations). The pharmaceutical preparations can be administered internally, such as orally (e.g. in the form of tablets, coated tablets, dragées, hard and soft gelatine capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically usable salts can be processed with pharmaceutically inert, inorganic or organic adjuvants for the production of tablets, coated tablets, dragées, and hard gelatine capsules. Lactose, corn starch or derivatives thereof, talc, stearic acid or its salts etc. can be used, for example, as such adjuvants for tablets, dragées, and hard gelatine capsules.

Suitable adjuvants for soft gelatine capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Morever, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances. The invention also relates to processes for the preparation of compounds of Formula I.

The compounds of general formula (I) of the present invention are prepared according to the general sequence of reactions outlined in the schemes below, wherein $R^1, R^2, R^3, R^4, R^5, R^6, R^7, R^8, R^{10}$ are as defined in formula (I) above. As the case may be any compound obtained with one or more optically active carbon atom may be resolved into pure enantiomers or diastereomers, mixtures of enantiomers or diastereomers, diastereomeric racemates and the mesoforms in a manner known per se.

The compounds obtained may also be converted into a pharmaceutically acceptable salt thereof in a manner known per se.

The compounds of formula (I) may be prepared as single compounds or as libraries of compounds comprising at least 2, e.g. 5 to 1000 compounds of formula (I).

Compound libraries may be prepared by a combinatorial approach or by multiple parallel synthesis using solution phase chemistry.

For the combinatorial approach, the compounds of general formula (I) wherein $R^6$, $R^7$, $R^9$ are hydrogen, are prepared using an Ugi-three-components-condensation reaction (Ugi-3-CC) which involves the one-pot reaction between a 1,2,3,4-tetrahydroisoquinoline derivative, an aldehyde and an isocyanide (Scheme 1).

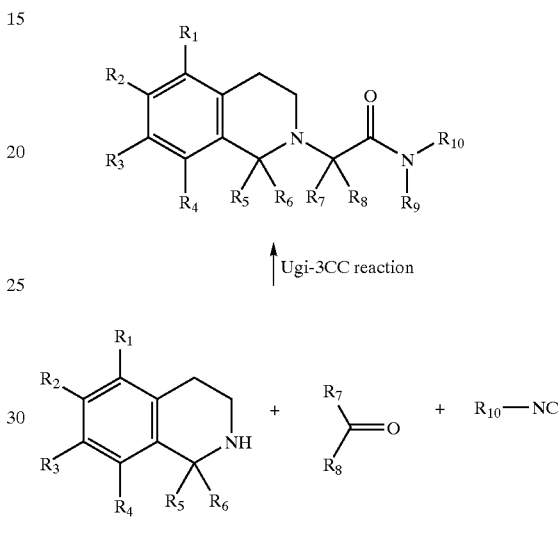

Isocyanides not commercially available might be prepared from the corresponding amines by N-formylation followed by treatment with $POCl_3$ (see e.g. J. March, fourth edition, Wiley-Interscience publication, p. 1042).

The compounds of the general formula (I) wherein $R^6$ and $R^7$ are hydrogen, may also be prepared by different procedures. The synthetic route depends on the last chemical transformation which has to be carried out.

In all cases in which the coupling of the tetrahydroisoquinoline with the amide side-chain is the final step the standard procedure shown in (Scheme 2) was followed. The tetrahydroisoquinolines as well as the amines ($R^9R^{10}NH$) could be either commercially available or synthesized.

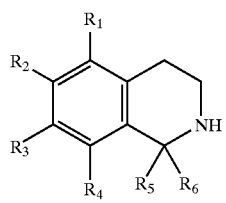

-continued

Procedure B

Procedure A

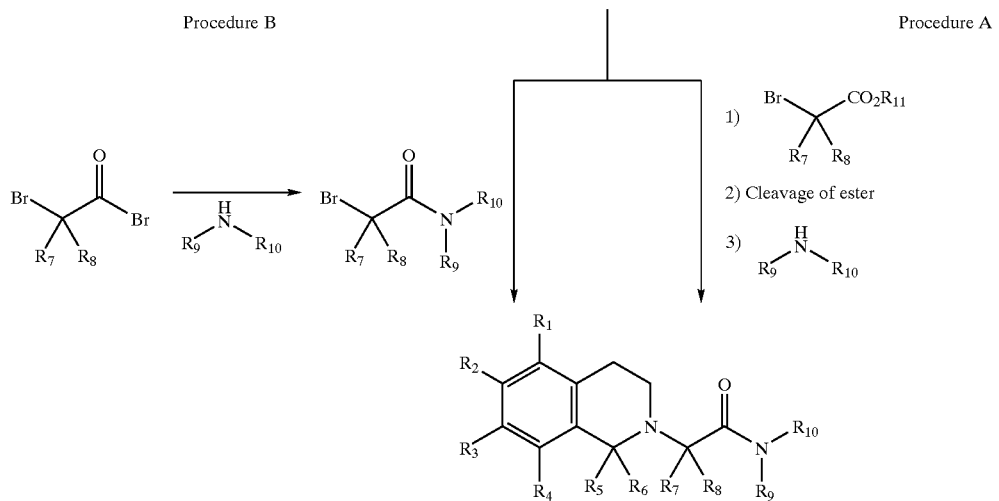

Tetrahydroisoquinolines not commercially available might be prepared from the corresponding phenylethylamines by coupling with the desired carboxylic acid followed by treatment with POCl$_3$ and finally NaBH$_4$ (see experimental part). All aminoindan-derivatives were prepared by reaction of 1-indanones with O-methylhydroxylamine followed by reduction with borane-tetrahydrofuran complex (Vaccaro W. et al., J. Med. Chem., 1996, 39, 1704–1719).

Compounds of general formula (I) wherein one substituent of the 1-benzyl-tetrahydroisoquinoline scaffold is a carbamoyloxy-, heteroaryloxy- or alkoxy-residue (not methoxy) are synthesized according to (Scheme 3). The benzyl-protected phenols are prepared by the procedure shown in (Scheme 2).

Scheme 3

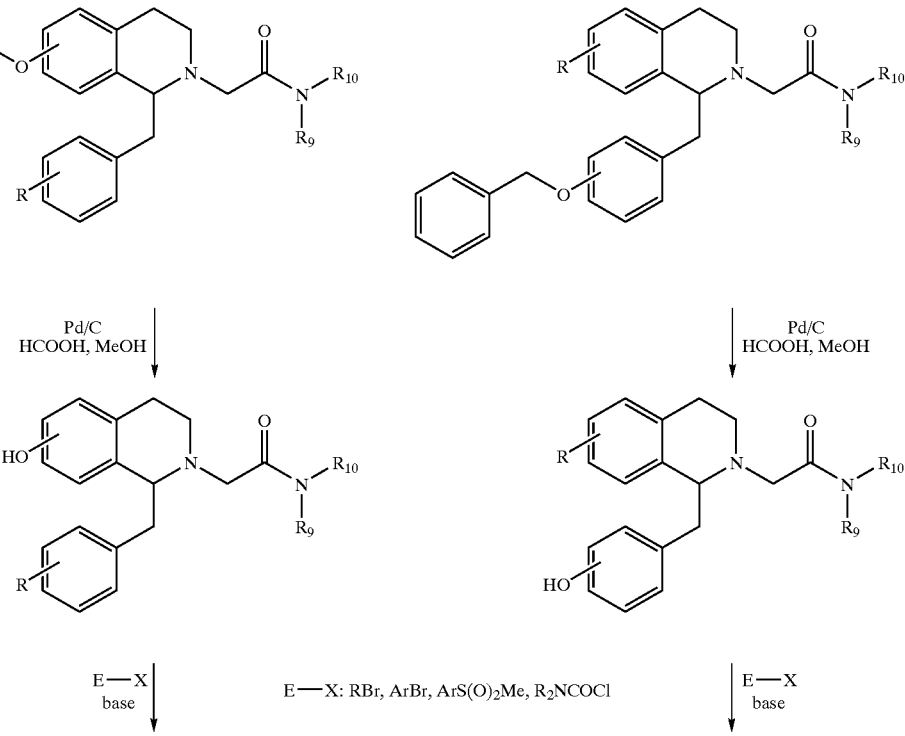

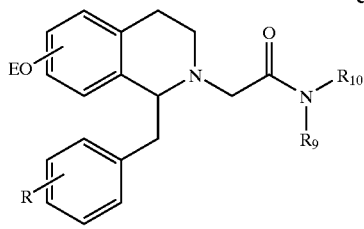

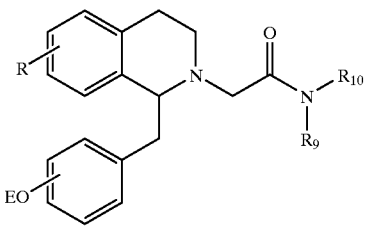

In the case $R^5$ (general formula I) is a heterocyclyl-methyl substituent the final step is the substitution of a mesylate function with the corresponding nitrogen containing nucleophile according to (Scheme 4). The required starting material was synthesized by the same procedure as described earlier (Scheme 2).

Scheme 4

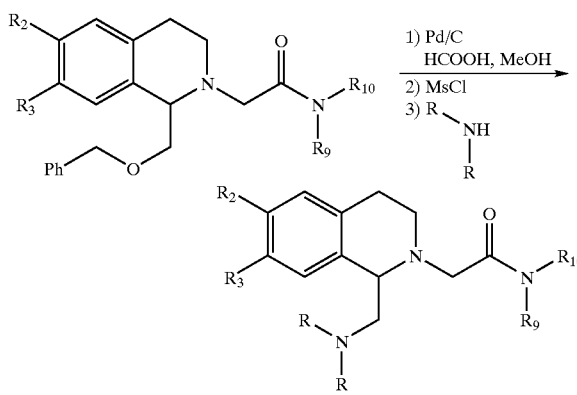

Stereochemically pure compounds of general formula I are obtained by kinetic resolution of the tetrahydroisoquinoline (Corrodi H., Hardegger E., Helv. Chim. Acta, 1956, 39, 889–897) and coupling of the pure enantiomer with the amide linker according to Scheme 2. Furthermore 2-[(1S)-1-(3,4-Dimethoxybenzyl)-6,7-dimethoxy-3,4-dihydro-1H-isoquinolin-2-yl]-N-[(1S)-indan-1-yl]-acetamide could also be obtained by crystallization of the diastereoisomeric mixture of the two 2-{1[R,S]-(3,4-Dimethoxybenzyl)-6,7-dimethoxy-3,4-dihydro-1H-isoquinolin-2-yl}-N-[(1S)-indan-1-yl]-acetamides from methanol.

Experimental Section
I. Biology
Determination of $OX_1$ Receptor Antagonist Activity The $OX_1$ receptor antagonist activity of the compounds of formula (I) was determinated in accordance with the following experimental method.
Experimental Method:
Intracellular Calcium Measurements Chinese hamster ovary (CHO) cells expressing the human orexin-1 receptor and the human orexin-2 receptor, respectively, were grown in culture medium (Ham F-12 with L-Glutamine) containing 300 μg/ml G418, 100 U/ml penicillin, 100 μg/ml streptomycin and 10% inactivated foetal calf serum (FCS).

The cells were seeded at 80,000 cells/well into 96-well black clear bottom sterile plates (Costar) which had been precoated with 1% gelatine in Hanks' Balanced Salt Solution (HBSS). All reagents were from Gibco BRL.

The seeded plates were incubated overnight at 37° C. in 5% $CO_2$.

Human orexin-A as an agonist was prepared as 1 mM stock solution in methanol:water (1:1), diluted in HBSS containing 0.1% bovine serum albumin (BSA) and 2 mM HEPES for use in the assay at a final concentration of 10 nM.

Antagonists were prepared as 10 mM stock solution in DMSO, then diluted in 96-well plates, first in DMSO, then in HBSS containing 0.1% bovine serum albumin (BSA) and 2 mM HEPES.

On the day of the assay, 100 μl of loading medium (HBSS containing 1% FCS, 2 mM HEPES, 5 mM probenecid (Sigma) and 3 μM of the fluorescent calcium indicator fluo-3 AM (1 mM stock solution in DMSO with 10% pluronic acid) (Molecular Probes) was added to each well.

The 96-well plates were incubated for 60 min at 37° C. in 5% $CO_2$. The loading solution was then aspirated and cells were washed 3 times with 200 μl HBSS containing 2.5 mM probenecid, 0.1% BSA, 2 mM HEPES. 100 μl of that same buffer was left in each well. Within the Fluorescent Imaging Plate Reader (FLIPR, Molecular Devices), antagonists were added to the plate in a volume of 50 μl, incubated for 20 min and finally 100 μl of agonist was added. Fluorescence was measured for each well at 1 second intervals, and the height of each fluorescence peak was compared to the height of the fluorescence peak induced by 10 nM orexin-A with buffer in place of antagonist. For each antagonist, $IC_{50}$ value (the concentration of compound needed to inhibit 50% of the agonistic response) was determined.

II. Chemistry

The following examples illustrate the preparation of pharmacologically active compounds of the invention but do not at all limit the scope thereof. All temperatures are stated in ° C.

All hydrochloride salts were prepared by dissolving the free-base in dichloromethane and treating with an excess of ethereal HCl (2M).
General Procedures:
A. General Procedure A:
1-[(3,4-Dimethoxy-benzyl)-6,7-dimethoxy-3,4-dihydro-1H-isoquinolin-2-yl]-acetic acid benzyl ester To a white suspension of 1-(4,5-dimethoxybenzyl)6,7-dimethoxy-1,2,3,4-tetrahydroisoquinoline-hydrochloride (1 g, 2.632 mmol) in a mixture of toluene/DMF (9/1) (10 ml), were added triethylamine (1.1 ml, 7.896 mmol) and chlorobenzylacetate (440 μl, 2.895 mmol). The reaction mixture was stirred at reflux under argon for 20 h. After cooling, the mixture was diluted in $CH_2Cl_2$ and washed with water.

The aqueous phase was extracted twice with $CH_2Cl_2$, the combined organic phases were dried over anhydrous $MgSO_4$, filtered and concentrated to give a crude brown-orange oil. Flash chromatography (AcOEt/hexane 1/1) gave 1.15 g (89%) of the title product as a brown-orange oil.
TLC (AcOEt/hexane: 1/1): $R_f$=0.55.
LC-MS (MeCN/$H_2O$: 1/1): $R_t$=4.16 min. m/z=492 (M+1).
1-(3,4-Dimethoxybenzyl)-6,7-dimethoxy-(3,4-dihydro-1H-isoquinolin-2-yl)-acetic acid.

To a solution of 1-[(3,4-dimethoxy-benzyl)-6,7-dimethoxy-3,4-dihydro-1H-isoquinolin-2-yl]-acetic acid benzyl ester (1.15 g, 2.34 mmol) in dry AcOEt (20 ml) was added in one portion Pd-C 10% (250 mg). The resulting black suspension was hydrogenated at normal pressure and room temperature for 20 h. The mixture was then filtered over celite and concentrated in vacuo to give brown crystals.

LC-MS (MeCN/H$_2$O: 1/1): R$_t$=3.34 min. m/z=402 (M+1).

EXAMPLE 1
2-[1-(3,4-Dimethoxy-benzyl)-6,7-dimethoxy-3,4-dihydro-1H-isoquinolin-2-yl]-N-benzyl-acetamide To a solution of 1-(4,5-dimethoxybenzyl)-6,7-dimethoxy-(3,4-dihydro-1H-isoquinolin-2-yl)-acetic acid (100 mg, 0.249 mmol) in 4 ml of dry DMF, were added 129.6 mg (0.249 mmol) of PyBOP, 29.9 µl (0.226 mmol) of benzylamine and dropwise 110 µl (0.521 mmol) of diisopropylethylamine (Hünig's base). The mixture reaction was stirred at RT under argon for 20 h. The mixture was then dissolved in CH$_2$Cl$_2$ and washed with water. The aqueous phase was extracted twice with CH$_2$Cl$_2$, the combined organic extracts were dried over MgSO$_4$, filtered and concentrated to give a crude brown residue. Flash chromatography (AcOEt/hexane 8/2) gave 126 mg (94%) of the title compound as a brown viscous oil.

TLC (AcOEt/hexane: 8/2): R$_f$=0.65.
LC-MS MeCN/H$_2$O: 1/1): R$_t$=4.83 min. m/z=491(M+1).

EXAMPLE 2
2-[1-(3,4-Dimethoxy-benzyl)-6,7-dimethoxy-3,4-dihydro-1H-isoquinolin-2-yl]-N-naphthalen-1-ylmethyl-acetamide In analogy to Example 1 but for the final step, reaction of 1-(4,5-dimethoxybenzyl)-6,7-dimethoxy-(3,4-dihydro-1H-isoquinolin-2-yl)-acetic acid with 1-naphthlalenemethylamine to give the title compound as the free-base (brown viscous oil) and the hydrochloride salt (brown crystals)

—TLC (AcOEt): R$_f$=0.55.
—LC-MS MeCN/H$_2$O: 1/1): R$_t$=5.97 min. m/z=541(M+1).

EXAMPLE 3
2-[1-(3,4-Dimethoxy-benzyl-6,7-dimethoxy-3,4-dihydro-1H-isoquinolin-2-yl]-N-(6-methoxy-naphthalen-2-ylmethyl)-acetamide In analogy to Example 1 but for the final step, reaction of 1-(4,5-dimethoxybenzyl)-6,7-dimethoxy-(3,4-dihydro-1H-isoquinolin-2-yl)-acetic acid with 6-methoxynaphthalene-2-methylamine to give the title compound as the free-base (brown oil).

—TLC (AcOEt): R$_f$=0.40 —LC-MS (MeCN/H$_2$O: 1/1): R$_t$=4.68 min. m/z=571(M+1).

2-(3-Bromo-4-methoxy-phenyl)-N-[2-(3,4-dimethoxy)-ethyl]-acetamide
LC-MS (MeCN/H$_2$O: 1/1): R$_t$ 4.28 min, 409 (M+1, ES+).
N-[2-(3,4-Dimethoxy-phenyl)-ethyl]-2-(3,4-dimethyl-phenyl)-acetamide
LC-MS (MeCN/H$_2$O: 1/1): R$_t$ 4.36 min, 328 (M+1, ES+).
2-(3,4-Diethyl-phenyl)-N-[2-(3,4-dimethoxy)-ethyl]-acetamide
LC-MS (MeCN/H$_2$O: 1/1): R$_t$ 4.18 min, 356 (M+1, ES+).
2-(3,4-Dichloro-phenyl)-N-[2-(3,4-dimethoxy)-ethyl]-acetamide
LC-MS (MeCN/H$_2$O: 1/1): R$_t$ 4.12 min, 369 (M+1, ES+).
1-(4-Bromo-3-methoxy-benzyl)-6,7-dimethoxy-1,2,3,4-tetrahydro-isoquinoline
LC-MS (MeCN/H$_2$O: 1/1): R$_t$ 2.96 min, 393 (M+1, ES+).
1-(3,4-Dimethyl-benzyl)-6,7-dimethoxy-1,2,3,4-tetrahydro-isoquinoline
LC-MS (MeCN/H$_2$O: 1/1): R$_t$ 3.19 min, 312 (M+1, ES+).
1-(3,4-Diethyl-benzyl)-6,7-dimethoxy-1,2,3,4-tetrahydro-isoquinoline
LC-MS (MeCN/H$_2$O: 1/1): R$_t$ 2.25 min, 340 (M+1, ES+).
1-(3,4-Dichloro-benzyl)-6,7-dimethoxy-1,2,3,4-tetrahydro-isoquinoline
LC-MS (MeCN/H$_2$O: 1/1): R$_t$ 3.20 min, 353 (M+1, ES+).
1-[(3,4-Dimethoxy-benzyl)-6,7-dimethoxy-1,2,3,4-tetrahydro-naphthalen-2-yl]-phenyl-acetic acid methyl ester To a white suspension of 1-(4,5-dimethoxybenzyl)6,7-dimethoxy-1,2,3,4-tetrahydroisoquinoline-hydrochloride (5 g, 0.013 mol) in dry toluene (50 ml), were added triethylamine (5.5 ml, 0.039 mol) and bromo-phenyl-acetic acid methyl ester (2.07 ml, 0.013 mol). The reaction mixture was stirred at reflux under argon for 20 h. After cooling, the mixture was diluted in CH$_2$Cl$_2$ and washed with water. The aqueous phase was extracted twice with CH$_2$Cl$_2$, the combined organic phases were dried over anhydrous MgSO$_4$, filtered and concentrated to give a crude brown-orange oil. Flash chromatography (AcOEt/hexane 1/1) gave 5.85 g (90%) of the title product as a brown-orange oil.

TLC (AcOEt/hexane: 1/1): R$_f$=0.55.
LC-MS (MeCN/H$_2$O: 1/1): R$_t$ 4.00 min and R$_t$ 4.36 min, 492 (M+1, ES+).

1-[(3,4-Dimethoxy-benzyl)-6,7-dimethoxy-1,2,3,4-tetrahydro-naphthalen-2-yl]-phenyl-acetic acid To a solution of 1-[(3,4-Dimethoxy-benzyl)-6,7-dimethoxy-1,2,3,4-tetrahydro-naphthalen-2-yl]-phenyl-acetic acid methyl ester (5.85 g, 0.011 mmol) in a mixture dioxane/MeOH (4/3) (160 ml) was added dropwise 2M NaOH$_{(aq)}$ (81 ml). The resulting mixture was stirred at RT for 20 h under nitrogen. The mixture was then concentrated in vacuo, combined with water and AcOEt. The aqueous phase was acidified until pH 1 with 2N HCl, extracted three times with with CH$_2$Cl$_2$, the combined organic phases were dried over anhydrous MgSO$_4$, filtered and concentrated to give the titled product (5.55 g, 97%) as yellow-green crystals.

LC-MS (MeCN/H$_2$O: 1/1): R$_t$ 3.62 min and R$_t$ 3.65 min, 478 (M+1, ES+).

EXAMPLE 4
2-[1-(3,4-Dimethoxy-benzyl)-6,7-dimethoxy-1,2,3,4-tetrahydro-naphthalen-2-yl]-N-indan-1-yl-2-phenyl-acetamide:

To a solution of 1-[(3,4-Dimethoxy-benzyl)-6,7-dimethoxy-1,2,3,4-tetrahydro-naphthalen-2-yl]-phenyl-acetic acid (100 mg, 0.209 mmol) in 5 ml of dry DMF, were added PyBOP (109 mg, 0.209 mmol), 1-aminoindane (32.3 mg, 0.19 mmol) and dropwise diisopropylethylamine (Hünig's base). (75 µl, 0.437 mmol). The mixture reaction was stirred at RT under argon for 20 h. The mixture was then dissolved in CH$_2$Cl$_2$ and washed with water. The aqueous phase was extracted twice with CH$_2$Cl$_2$, the combined organic extracts were dried over MgSO$_4$, filtered and concentrated to give a crude brown residue. Flash chromatography (AcOEt) gave 72 mg (64%) of the title compound as a pale brown oil.

TLC (AcOEt): R$_f$=0.65.
LC-MS (MeCN/H$_2$O: 1/1): R$_t$ 4.35 min and R$_t$ 4.60 min, 593 (M+1, ES+).

EXAMPLE 5
N-Butyl-2-[1-(3,4-Dimethoxy-benzyl)-6,7-dimethoxy-1,2,3,4-tetrahydro-naphthalen-2-yl]-2-phenyl-acetamide prepared by reaction of 1-[(3,4-Dimethoxy-benzyl)-6,7-dimethoxy-1,2,3,4-tetrahydro-naphthalen-2-yl]-phenyl-acetic acid with n-butylamine.

LC-MS (MeCN/H$_2$O: 1/1): R$_t$ 4.09 min 533 (M+1, ES+).

1-[(3,4-Dimethoxy-benzyl)-6,7-dimethoxy-1,2,3,4-tetrahydro-naphthalen-2-yl]-pyrimidin-acetic acid ethyl ester To a white suspension of 1-(4,5-dimethoxybenzyl)-6,7-dimethoxy-1,2,3,4-tetrahydroisoquinoline-hydrochloride (1.65 g, 4.36 mmol) in dry DMF (5 ml), were added triethylamine (1.82 ml, 0.013 mol) and bromo-pyrimidin-acetic acid ethyl ester (1.07 g, 4.36 mmol). The reaction mixture was stirred at reflux under argon for 20 h. After cooling, the mixture was diluted in AcOEt and washed with water. The aqueous phase was extracted twice with $CH_2Cl_2$, the combined organic phases were dried over anhydrous AcOEt, filtered and concentrated to give a crude brown-orange oil. Flash chromatography (AcOEt) gave 1.4 g (63%) of the title product as a brown-orange oil.

TLC (AcOEt): $R_f$=0.55.

LC-MS (MeCN/$H_2$O: 1/1): $R_t$ 4.54 min and $R_t$ 4.69 min, 508 (M+1, ES+).

1-[(3,4-Dimethoxy-benzyl)-6,7-dimethoxy-1,2,3,4-tetrahydro-naphthalen-2-yl]-pyrimidin-acetic acid To a solution of 1-[(3,4-Dimethoxy-benzyl)-6,7-dimethoxy-1,2,3,4-tetrahydro-naphthalen-2-yl]-pyrimidin-acetic acid ethyl ester (1.4 g, 2.75 mmol) in a mixture dioxane/MeOH (4/3) (35 ml) was added dropwise 2M $NaOH_{(aq)}$ (24 ml). The resulting mixture was stirred at RT for 20 h under nitrogen. The mixture was then concentrated in vacuo, combined with water and AcOEt. The aqueous phase was acidified until pH 1 with 2N HCl, extracted three times with with $CH_2Cl_2$, the combined organic phases were dried over anhydrous $MgSO_4$, filtered and concentrated to give the titled product (1.23 g, 93%) as yellow-green crystals.

LC-MS (MeCN/$H_2$O: 1/1): $R_t$ 3.11 min and $R_t$ 3.24 min, 480 (M+1, ES+).

EXAMPLE 6

2-[1-(3,4-Dimethoxy-benzyl)-6,7-dimethoxy-1,2,3,4-tetrahydro-naphthalen-2-yl]-2-N-indan-2-yl-2-pyrimidin-5-yl-acetamide prepared by reaction of 1-[(3,4-Dimethoxy-benzyl)-6,7-dimethoxy-1,2,3,4-tetrahydro-naphthalen-2-yl]-pyrimidin-acetic acid with 2-aminoindane hydrochloride.

LC-MS (MeCN/$H_2$O: 1/1): $R_t$ 4.64 min and $R_t$ 4.83 min, 595 (M+1, ES+).

EXAMPLE 7

N-benzyl-2-[1-(3,4-Dimethyl-benzyl)-6,7-dimethoxy-3,4-dihydro-1H-isoquinolin-2-yl]-acetamide:

prepared by reaction of 1-(3,4-dimethyl-benzyl)-6,7-dimethoxy-1,2,3,4-tetrahydroisoquinoline and 2-bromoacetyl bromide with benzylamine.

LC-MS (MeCN/$H_2$O: 1/1): $R_t$=4.35 min, 459 (M+1, ES+).

EXAMPLE 8

2-[1-(3,4-Dimethyl-benzyl)-6,7-dimethoxy-3,4-dihydro-1H-isoquinolin-2-yl]-N-indan-1-yl-acetamide:

prepared by reaction of 1-(3,4-dimethyl-benzyl)-6,7-dimethoxy-1,2,3,4-tetrahydroisoquinoline and 2-bromoacetyl bromide with 1-aminoindane.

LC-MS (MeCN/$H_2$O: 1/1): $R_t$=4.47 min, 485(M+1, ES+).

EXAMPLE 9

2-[1-(3,4-Dimethyl-benzyl)-6,7-dimethoxy-3,4-dihydro-1H-isoquinolin-2-yl]-N-pyridin-2-yl-acetamide:

prepared by reaction of 1-(3,4-dimethyl-benzyl)-6,7-dimethoxy-1,2,3,4-tetrahydroisoquinoline and 2-bromoacetyl bromide with 2-picolylamine.

LC-MS (MeCN/$H_2$O: 1/1): $R_t$=2.99 min, 460 (M+1, ES+).

EXAMPLE 10

2-[1-(3,4-Dimethyl-benzyl)-6,7-dimethoxy-3,4-dihydro-1H-isoquinolin-2-yl]-N-pyridin-3-yl-acetamide:

prepared by reaction of 1-(3,4-dimethyl-benzyl)-6,7-dimethoxy-1,2,3,4-tetrahydroisoquinoline and 2-bromoacetyl bromide with 3-picolylamine.

LC-MS (MeCN/$H_2$O: 1/1): $R_t$=2.61 min, 460 (M+1, ES+).

EXAMPLE 11

N-benzyl-2-[1-(3,4-Diethyl-benzyl)-6,7-dimethoxy-3,4-dihydro-1H-isoquinolin-2-yl]-acetamide:

prepared by reaction of 1-(3,4-diethyl-benzyl)-6,7-dimethoxy-1,2,3,4-tetrahydroisoquinoline and 2-bromoacetyl bromide with benzylamine.

LC-MS (MeCN/$H_2$O: 1/1): $R_t$=4.35 min, 459 (M+1, ES+).

EXAMPLE 12

2-[1-(3,4-Diethyl-benzyl)-6,7-dimethoxy-3,4-dihydro-1H-isoquinolin-2-yl]-N-(pyridin-2-yl-methyl)-acetamide:

prepared by reaction of 1-(3,4-diethyl-benzyl)-6,7-dimethoxy-1,2,3,4-tetrahydroisoquinoline and 2-bromoacetyl bromide with 2-picolylamine.

LC-MS (MeCN/$H_2$O: 1/1): $R_t$=2.87 min, 488 (M+1, ES+).

EXAMPLE 13

2-[1-(3,4-Diethyl-benzyl)-6,7-dimethoxy-3,4-dihydro-1H-isoquinolin-2-yl]-N-(pyridin-3-yl-methyl)-acetamide:

prepared by reaction of 1-(3,4-diethyl-benzyl)-6,7-dimethoxy-1,2,3,4-tetrahydroisoquinoline and 2-bromoacetyl bromide with 3-picolylamine.

LC-MS (MeCN/$H_2$O: 1/1): $R_t$=2.85 min. 488 (M+1, ES+).

EXAMPLE 14

2-[1-(3,4-Diethyl-benzyl)-6,7-dimethoxy-3,4-dihydro-1H-isoquinolin-2-yl]-N-(pyridin-4-yl-methyl)-acetamide:

prepared by reaction of 1-(3,4-diethyl-benzyl)-6,7-dimethoxy-1,2,3,4-tetrahydroisoquinoline and 2-bromoacetyl bromide with 4-picolylamine.

LC-MS MeCN/$H_2$O: 1/1): $R_t$=2.71 min. 488 (M+1, ES+).

EXAMPLE 15

2-[1-(3,4-Dichloro-benzyl)-6,7-dimethoxy-3,4-dihydro-1H-isoquinolin-2-yl]-N-(pyridin-2-yl-methyl-acetamide:

prepared by reaction of 1-(3,4-dichloro-benzyl)-6,7-dimethoxy-1,2,3,4-tetrahydroisoquinoline and 2-bromoacetyl bromide with 2-picolylamine.

LC-MS (MeCN/$H_2$O: 1/1): $R_t$=3.72 min, 501 (M+1, ES+).

EXAMPLE 16

2-[1-(3,4-Dichloro-benzyl)-6,7-dimethoxy-3,4-dihydro-1H-isoquinolin-2-yl]-N-(pyridin-3-yl-methyl)-acetamide:

prepared by reaction of 1-(3,4-dichloro-benzyl)-6,7-dimethoxy-1,2,3,4-tetrahydroisoquinoline and 2-bromoacetyl bromide with 3-picolylamine.

LC-MS (MeCN/$H_2$O: 1/1): $R_t$=3.29 min, 501 (M+1, ES+).

B Coupling of 1,2,3,4-Tetrahydroisoquinolines with 2-Bromoacetamides

B.1 Starting Materials: Synthesis of 1,2,3,4-Tetrahydroisoquinoline Derivatives:

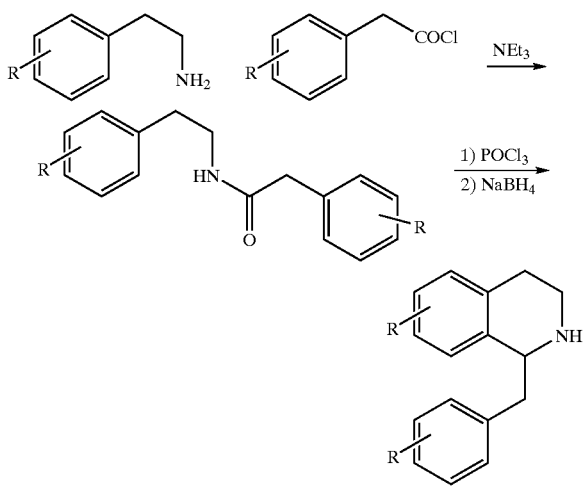

B.1.1 Synthesis of the Phenylethylamides:

Procedure I:

A solution of the respective phenylethylamine (80 mmol) and of triethylamine (90 mmol) in THF (120 mL) was cooled to 0° C. and treated portionwise with the respective acetyl chloride (80 mmol). After stirring for 10 min at 0° C. and for 14 h at room temperature a sat. aqueous $NaHCO_3$ solution was added, the phases were separated and the aqueous phase was extracted three times with ethyl acetate (150 mL). The solvent was removed in vacuo and the residue was either recrystalized from toluene or purified by flash chromatography to give the following amides:

N-[2-(3-Methoxy-phenyl)-ethyl]-3,4-dimethoxyphenyl-acetamide:
prepared by reaction of 3-methoxyphenylethylamine with 3,4-dimethoxyphenyl acetyl chloride.
LC-MS: rt=4.1 min, 330 (M+1, ES+).

N-[2-(3,4-Dimethoxy-phenyl)-ethyl]-phenyl-acetamide:
prepared by reaction of 3,4-dimethoxyphenylethylamine with phenyl acetyl chloride.

N-[2-(3,4-Dimethoxy-phenyl)-ethyl]-3-methoxyphenyl-acetamide:
prepared by reaction of 3,4-dimethoxyphenylethylamine with 3-methoxyphenyl acetyl chloride.
LC-MS: rt=4.0 min, 330 (M+1, ES+).

N-[2-(3,4-Dimethoxy-phenyl)-ethyl]-4-methoxyphenyl-acetamide:
prepared by reaction of 3,4-dimethoxyphenylethylamine with 4-methoxyphenyl acetyl chloride.
LC-MS: rt=4.0 min, 330 (M+1, ES+).

N-[2-(3,4-Dimethoxy-phenyl)-ethyl]-2,5-dimethoxyphenyl-acetamide:
prepared by reaction of 3,4-dimethoxyphenylethylamine with 2,5-dimethoxyphenyl acetyl chloride.
LC-MS: rt=4.1 min, 360 (M+1, ES+).

N-[2-(2,5-Dimethoxy-phenyl)-ethyl]-3,4-dimethoxyphenyl-acetamide:
prepared by reaction of 2,5-dimethoxyphenylethylamine with 3,4-dimethoxyphenyl acetyl chloride.
LC-MS: rt=4.2 min, 360 (M+1, ES+).

N-[2-(3,4-Dimethoxy-phenyl)-ethyl]-3-phenyl-propionamide:
prepared by reaction of 3,4-dimethoxyphenylethylamine with 3-phenyl propionyl chloride.
LC-MS: rt=4.2 min, 314 (M+1, ES+).

N-[2-(3,4-Dimethoxy-phenyl)-ethyl]-2-phenyl-butyramide:
prepared by reaction of 3,4-dimethoxyphenylethylamine with 2-Phenylbutyryl chloride.
$R_f$=0.21 (ethyl acetate/heptane 1/1)

N-[2-(2,5-Dimethoxy-phenyl)-ethyl]-diphenyl-acetamide:
prepared by reaction of 2,5-dimethoxyphenylethylamine with diphenylacetyl chloride.
LC-MS: rt=5.3 min, 376 (M+1, ES+).

N-[2-(2,5-Dimethoxy-phenyl)-ethyl]-2,5-dimethoxyphenyl-acetamide:
prepared by reaction of 2,5-dimethoxyphenylethylamine with 2,5-dimethoxyphenyl acetyl chloride.
LC-MS: rt=4.6 min, 360 (M+1, ES+).

N-[2-(3,4-Dimethoxy-phenyl)-ethyl]-4-chlorophenyl-acetamide:
prepared by reaction of 3,4-dimethoxyphenylethylamine with 4-chlorophenyl acetyl chloride.
LC-MS: rt=4.4 min, 334 (M+1, ES+).

N-[2-(2,5-Dimethoxy-phenyl)-ethyl]-phenyl-acetamide:
prepared by reaction of 2,5-dimethoxyphenylethylamine with phenylacetyl chloride.
LC-MS: rt=4.5 min, 300 (M+1, ES+).

N-[2(3-methoxy-isopropoxy-phenyl)-ethyl]-3,4-dimethoxyphenyl-acetamide:
prepared by reaction of 3-methoxy-4-isopropoxyphenylethylamine with 3,4-dimethoxyphenyl acetyl chloride.
LC-MS: rt=4.2 min, 388 (M+1, ES+).

N-[2-3,4,5-Trimethoxy-phenyl)ethyl]-3,4-dimethoxyphenyl-acetamide:
prepared by reaction of 3,4,5-trimethoxyphenylethylamine with 3,4-dimethoxyphenyl acetyl chloride.
LC-MS: rt=3.8 min, 390 (M+1, ES+).

N-[2-2,3,4-Trimethoxy-phenyl)-ethyl]-3,4-dimethoxyphenyl-acetamide:
prepared by reaction of 2,3,4-trimethoxyphenylethylamine with 3,4-dimethoxyphenyl acetyl chloride.
LC-MS: rt=4.1 min, 390 (M+1, ES+).

N-[2-(3-Dimethoxy-phenyl)ethyl]-3,4-dimethoxyphenyl-acetamide:
prepared by reaction of 3,5-timethoxyphenylethylamine with 3,4-dimethoxyphenyl acetyl chloride.
LC-MS: rt=4.2 min, 360 (M+1, ES+).

N-[2-3-Benzyloxy-4-methoxy-phenyethyl]-3,4-dimethoxyphenyl-acetamide:
prepared by reaction of 3-benzyloxy-4-methoxyphenylethylamine with 3,4-dimethoxyphenyl acetyl chloride.
LC-MS: rt=4.7 min, 436 (M+1, ES+), 434 (M−1, ES−).

N-[2-(4-(Benzyloxy-3-methoxy-phenyl)ethyl]-3,4-dimethoxyphenyl-acetamide:
prepared by reaction of 4-benzyloxy-3-methoxyphenylethylamine with 3,4-dimethoxyphenyl acetyl chloride.
LC-MS: rt=4.8 min, 436 (M+1, ES+).

N-[2-(2-Benzyloxy-5-methoxy-phenyl)ethyl]-3,4-dimethoxyphenyl-acetamide:
prepared by reaction of 2-benzyloxy-5-methoxyphenylethylamine with 3,4-dimethoxyphenyl acetyl chloride.
LC-MS: rt=4.8 min, 436 (M+1, ES+).

N-[2-(5-Benzyloxy-2-methoxy-phenyl)-ethyl]-3,4-dimethoxyphenyl-acetamide:

prepared by reaction of 5-benzyloxy-2-methoxyphenylethylamine with 3,4-dimethoxyphenyl acetyl chloride.

LC-MS: rt=4.9 min, 436 (M+1, ES+).

N-[2-(3,4-Dimethoxy-phenyl)-ethyl]-benzyloxy-acetamide:

prepared by reaction of 3,4-dimethoxyphenylethylamine with benzyloxy acetyl chloride.

LC-MS: rt=4.2 min, 330 (M+1, ES+).

Procedure II:

A solution of the respective phenylethylamine (25.0 mmol) and the respective phenylacetic acid (25.0 mmol) in 100 mL toluene was refluxed for 24 h in the presence of a Dean-Stark. The solvent was removed in vacuo and the residue was either recrystalized from toluene or purified by flash chromatography to give the following amides:

N-[2-(3,4-Dimethoxy-phenyl)-ethyl]-3,4-methylenedioxyphenyl-acetamide:

prepared by reaction of 3,4-dimethoxyphenylethylamine and 3,4-methylenedioxyphenylacetic acid.

LC-MS: rt=4.1 min, 344 (M+1, ES+).

N-[2-(3,4-Dimethoxy-phenyl)-ethyl]-4-dimethylaminophenyl-acetamide:

prepared by reaction of 3,4-dimethoxyphenylethylamine and 4-dimethyl-aminophenylacetic acid.

LC-MS: rt=3.1 min, 343 (M+1, ES+).

N-[2-(3,4-Dimethoxy-phenyl)-ethyl]-4-fluorophenyl-acetamide:

prepared by reaction of 3,4-dimethoxyphenylethylamine and 4-fluorophenyl-acetic acid.

LC-MS: rt=4.1 min, 318 (M+1, ES+).

N-[2-(3,4-Dimethoxy-phenyl)-ethyl]-3,4-difluorophenyl-acetamide:

prepared by reaction of 3,4-dimethoxyphenylethylamine and 3,4-difluorophenylacetic acid.

LC-MS: rt=4.2 min, 336 (M+1, ES+).

N-[2-(3,4-Dimethoxy-phenyl)-ethyl]-3,4,5-trimethoxyphenyl-acetamide:

prepared by reaction of 3,4-dimethoxyphenylethylamine and 3,4,5-trimethoxyphenylacetic acid.

LC-MS: rt=3.8 min, 390 (M+1, ES+).

N-[2-(3,4-Dimethoxy-phenyl)-ethyl]-2,3,4-trimethoxyphenyl-acetamide:

prepared by reaction of 3,4-dimethoxyphenylethylamine and 2,3,4-trimethoxyphenylacetic acid.

LC-MS: rt=4.1 min, 390 (M+1, ES+).

N-[2-(3,4-Dimethoxy-phenyl)-ethyl]-naphthalen-2-yl-acetamide:

prepared by reaction of 3,4-dimethoxyphenylethylamine and 2-naphthylacetic acid.

LC-MS: rt=4.9 min, 350 (M+1, ES+).

N-[2-2,5-Dimethoxy-phenyl)-ethyl]-3,4-methylenedioxyphenyl-acetamide:

prepared by reaction of 2,5-dimethoxyphenylethylamine and 3,4-methylenedioxyphenylacetic acid.

LC-MS: rt=4.3 min, 344 (M+1, ES+).

N-[2-(3,4-Dimethoxy-phenyl)-ethyl]-4-hydroxy-3-methoxy-phenyl-acetamide:

prepared by reaction of 3,4-dimethoxyphenylethylamine and 4-hydroxy-3-methoxy-phenylacetic acid.

LC-MS: rt=3.6 min, 346 (M+1, ES+), 344 (M−1, ES−).

N-[2-(3,4-Dimethoxy-phenyl)-ethyl]-3-benzyloxy-4-methoxy-phenyl-acetamide:

prepared by reaction of 3,4-dimethoxyphenylethylamine and 3-benzyloxy-4-methoxy-phenylacetic acid.

LC-MS: rt=4.6 min, 436 (M+1, ES+), 434 (M−1, ES−).

B.1.2. Synthesis of 1,2,3,4-Tetrahydroisoquinolines via Bischler-Napieralski-Reaction (General Procedure):

To a suspension of the respective acetamide (60 mmol) in acetonitrile (100 mL) was added phosphorus oxychloride (16.2 mL, 177 mmol). The mixture was heated to reflux for 6 h and the solvent was removed in vacuo. The resulting oil was taken up in MeOH (70 mL), evaporated to dryness, dissolved in MeOH (130 mL) and cooled to 0° C. NaBH$_4$ was added in small (!) portions and the reaction mixture was stirred for 14 h. The solvent was removed in vacuo, dichloromethane (150 mL) and water (100 mL) were added, the phases were separated and the aqueous phase was extracted three times with dichloromethane (100 mL). The combined organic phases were concentrated in vacuo to give the following tetrahydroisoquinolines, which were purified either by flash chromatography or by crystallization as hydrochloride salt:

1-(3,4-Dimethoxy-benzyl)6-methoxy-1,2,3,4-tetrahydroisoquinoline:

prepared by cyclisation of N-[2-(3-Methoxy-phenyl)-ethyl]-3,4-dimethoxyphenyl-acetamide.

LC-MS: rt=3.1 min, 314 (M+1, ES+).

1-Benzyl-6,7-dimethoxy-1,2,3,4-tetrahydroisoquinoline:

prepared by cyclisation of N-[2-(3,4-Dimethoxy-phenyl)-ethyl]-phenyl acetamide.

R$_f$ (dichloromethane/methanol 5/1)=0.51.

LC-MS: rt=3.1 min, 284 (M+1, ES+).

1-(3-Methoxy-benzyl)-6,7-dimethoxy-1,2,3,4-tetrahydroisoquinoline:

prepared by cyclisation of N-[2-(3,4-Dimethoxy-phenyl)-ethyl]-3-methoxyphenyl acetamide.

LC-MS: rt=3.0 min, 314 (M+1, ES+).

1-(4-Methoxy-benzyl)-6,7-dimethoxy-1,2,3,4-tetrahydroisoquinoline:

prepared by cyclisation of N-[2-(3,4-Dimethoxy-phenyl)-ethyl]-4-methoxyphenyl acetamide.

LC-MS: rt=3.0 min, 314 (M+1, ES+).

1-(2,5-Dimethoxy-benzyl)-6,7-dimethoxy-1,2,3,4-tetrahydroisoquinoline:

prepared by cyclisation of N-[2-(3,4-Dimethoxy-phenyl)-ethyl]-2,5-dimethoxy-phenyl acetamide.

LC-MS: rt=3.2 min, 344 (M+1, ES+).

1-(3,4-Dimethoxy-benzyl)-5,8-dimethoxy-1,2,3,4-tetrahydroisoquinoline:

prepared by cyclisation of N-[2-(2,5-Dimethoxy-phenyl)-ethyl]-3,4-dimethoxy-phenyl acetamide.

LC-MS: rt=3.3 min, 344 (M+1, ES+).

1-(2-Phenyl-ethyl)-6,7-dimethoxy-1,2,3,4-tetrahydroisoquinoline:

prepared by cyclisation of N-[2-(3,4-Dimethoxy-phenyl)-ethyl]-3-phenyl-propionamide.

LC-MS: rt=3.2 min, 298 (M+1, ES+).

1-(1-Phenyl-propyl)-6,7-dimethoxy-1,2,3,4-tetrahydroisoquinoline: prepared by cyclisation of N-[2-(3,4-Dimethoxy-phenyl)-ethyl]-2-phenyl-butyramide.

LC-MS: rt=3.3 min 312 (M+1, ES+).

1-(Diphenylmethyl)-5,8-dimethoxy-1,2,3,4-tetrahydroisoquinoline:

prepared by cyclisation of N-[2-(2,5-Dimethoxy-phenyl)-ethyl]-diphenyl acetamide.

LC-MS: rt=3.7 min, 360 (M+1, ES+).

1-(2,5-Dimethoxy-benzyl)-5,8-dimethoxy-1,2,3,4-tetrahydroisoquinoline:

prepared by cyclisation of N-[2-(2,5-Dimethoxy-phenyl)-ethyl]-2,5-dimethoxy-phenyl acetamide.

LC-MS: rt=3.6 min, 344 (M+1, ES+).

1-(4-Chloro-benzyl)-6,7-dimethoxy-1,2,3,4-tetrahydroisoquinoline:

prepared by cyclisation of N-[2-(3,4-Dimethoxy-phenyl)-ethyl]-4-chloro-phenyl acetamide.

LC-MS: rt=3.2 min, 318 (M+1, ES+).
1-Benzyl-5,8-dimethoxy-1,2,3,4-tetrahydroisoquinoline:
prepared by cyclisation of N-[2-(2,5-Dimethoxy-phenyl)-ethyl]-phenyl acetamide.
LC-MS: rt=3.4 min, 284 (M+1, ES+).
1-(3,4-Dimethoxy-benzyl)-6-methoxy-7-isopropoxy-1,2,3,4-tetrahydro-isoquinoline:
prepared by cyclisation of N-[2-(3-Methoxy-4-isopropoxy-phenyl)-ethyl]-3,4-dimethoxy-phenyl acetamide.
LC-MS: rt=3.32 min, 372 (M+1, ES+).
1-(3,4-Methylenedioxy-benzyl)-6,7-dimethoxy-1,2,3,4-tetrahydro-isoquinoline:
prepared by cyclisation of N-[2-(3,4-Dimethoxy-phenyl)-ethyl]-3,4-methylenedioxy-phenyl acetamide.
LC-MS: rt=3.0 min, 328 (M+1, ES+).
1-(4-Dimethylamino-benzyl)-6,7-dimethoxy-1,2,3,4-tetrahydro-isoquinoline;
prepared by cyclisation of N-[2-(3,4-Dimethoxy-phenyl)-ethyl]-4-dimethyl-amino-phenyl acetamide.
LC-MS: rt=2.6 min, 327 (M+1, ES+).
1-(4-Fluoro-benzyl)-6,7-dimethoxy-1,2,3,4-tetrahydroisoquinoline:
prepared by cyclisation of N-[2-(3,4-Dimethoxy-phenyl)-ethyl]-4-fluoro-phenyl acetamide.
LC-MS: rt=3.1 min, 302 (M+1, ES+).
1-(3,4-Difluoro-benzyl)-6,7-dimethoxy-1,2,3,4-tetrahydroisoquinoline:
prepared by cyclisation of N-[2-(3,4-Dimethoxy-phenyl)-ethyl]-3,4-difluoro-phenyl acetamide.
LC-MS: rt=3.1 min. 320 (M+1, ES+).
1-(3,4,5-Trimethoxy-benzyl)-6,7-dimethoxy-1,2,3,4-tetrahydro-isoquinoline:
prepared by cyclisation of N-[2-(3,4-Dimethoxy-phenyl)-ethyl]-3,4,5-trimethoxy-phenyl acetamide.
LC-MS: rt=3.0 min, 374 (M+1, ES+).
1-(3,4-Dimethoxy-benzyl)-6,7,8-trimethoxy-1,2,3,4-tetrahydro-isoquinoline:
prepared by cyclisation of N-[2-(3,4,5-Trimethoxy-phenyl)-ethyl]-3,4-dimethoxy-phenyl acetamide.
LC-MS: rt=3.2 min, 374 (M+1, ES+).
1-(3,4-Dimethoxy-benzyl)-5,6,7-trimethoxy-1,2,3,4-tetrahydro-isoquinoline:
prepared by cyclisation of N-[2-(2,3,4-Trimethoxy-phenyl)-ethyl]-3,4-dimethoxy-phenyl acetamide.
LC-MS: rt=3.2 min, 374 (M+1, ES+).
1-(3,4-Dimethoxy-benzyl)-6,8-dimethoxy-1,2,3,4-tetrahydro-isoquinoline:
prepared by cyclisation of N-[2-(3,5-Dimethoxy-phenyl)-ethyl]-3,4-dimethoxy-phenyl acetamide.
LC-MS: rt=3.5 min, 344 (M+1, ES+).
1-(2,3,4-Trimethoxy-benzyl)-6,7-dimethoxy-1,2,3,4-tetrahydro-isoquinoline:
prepared by cyclisation of N-[2-(3,4-Dimethoxy-phenyl)-ethyl]-2,3,4-trimethoxy-phenyl acetamide.
LC-MS: rt=3.2 min, 374 (M+1, ES+).
1-(Naphthalen-2-yl-methyl)-6,7-dimethoxy-1,2,3,4-tetrahydro-isoquinoline:
prepared by cyclisation of N-[2-(3,4-Dimethoxy-phenyl)-ethyl]-naphthalen-2-yl acetamide.
LC-MS: rt=3.6 min, 334 (M+1, ES+).
1-(3,4-Methylenedioxy-benzyl)-5,8-dimethoxy-1,2,3,4-tetrahydro-isoquinoline:
prepared by cyclisation of N-[2-(2,5-Dimethoxy-phenyl)-ethyl]-3,4-methylenedioxy-phenyl acetamide.
LC-MS: rt=3.2 min, 328 (M+1, ES+).
1-(3,4-Dimethoxy-benzyl)4-benzyloxy-7-methoxy-1,2,3,4-tetrahydro-isoquinoline:
prepared by cyclisation of N-[2-(3-Benzyloxy-4-methoxy-phenyl)-ethyl]-3,4-dimethoxy-phenyl acetamide.
LC-MS: rt=3.7 min, 420 (M+1, ES+).
1-(3,4-Dimethoxy-benzyl)-7-benzyloxy-6-methoxy-1,2,3,4-tetrahydro-isoquinoline:
prepared by cyclisation of N-[2-(4-Benzyloxy-3-methoxy-phenyl)-ethyl]-3,4-dimethoxy-phenyl acetamide.
LC-MS: rt=3.6 min, 420 (M+1, ES+).
1-(3,4-Dimethoxy-benzyl-5-benzyloxy-8-methoxy-1,2,3,4-tetrahydro-isoquinoline:
prepared by cyclisation of N-[2-(2-Benzyloxy-5-methoxy-phenyl)-ethyl]-3,4-dimethoxy-phenyl acetamide.
LC-MS: rt=4.1 min, 420 (M+1, ES+).
1-(3,4-Dimethoxy-benzyl)-8-benzyloxy-5-methoxy-1,2,3,4-tetrahydro-isoquinoline:
prepared by cyclisation of N-[2-(5-Benzyloxy-2-methoxy-phenyl)-ethyl]-3,4-dimethoxy-phenyl acetamide.
LC-MS: rt=3.9 min, 420 (M+1, ES+).
1-(4-Hydroxy-3-methoxy-benzyl)-6,7-dimethoxy-1,2,3,4-tetrahydro-isoquinoline:
prepared by cyclisation of N-[2-(3,4-dimethoxy-phenyl)-ethyl]-4-hydroxy-3-methoxy-phenyl acetamide.
LC-MS: rt=2.8 min, 330 (M+1, ES+).
1-(3-Benzyloxy-4-methoxy-benzyl)-6,7-dimethoxy-1,2,3,4-tetrahydro-isoquinoline:
prepared by cyclisation of N-[2-(3,4-dimethoxy-phenyl)-ethyl]-3-benzyloxy-4-methoxy-phenyl acetamide.
LC-MS: rt=3.6 min, 420 (M+1, ES+).
1-Benzyloxymethyl-6,7-dimethoxy-1,2,3,4-tetrahydro-isoquinoline:
prepared by cyclisation of N-[2-(3,4-dimethoxy-phenyl)-ethyl]-benzyloxy-acetamide.

B.2. Alkylation of 1,2,3,4-Tetrahydroisoquinolines with 2-Bromo-acetamides (General Procedure)

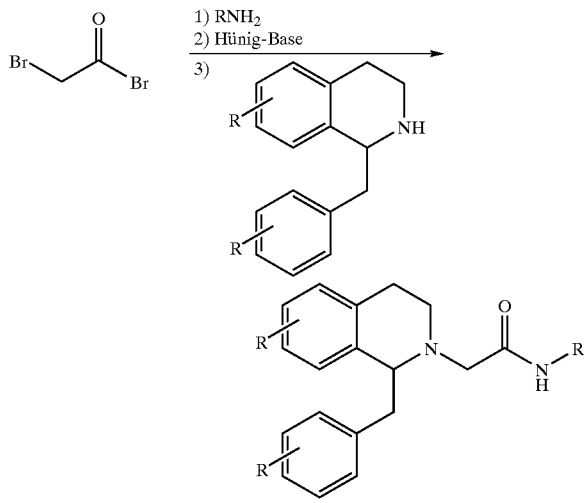

At −15° C. a solution of the respective amine in THF (250 μL, 0.40 M) was added to a solution of 2-bromoacetyl bromide in THF (500 μL, 0.20 M). The reaction mixture was treated with a solution of diisopropylethylamine in THF (250 μL, 2.0 M), allowed to warm up to room temperature and stirred for 30 min. A solution of the respective tetrahydroisoquinoline in DMSO (500 μL, 0.20 M) was added and the mixture was heated to 75° C. for 18 h. After cooling to room temperature water (2.0 mL) and ethyl acetate (2.0 mL) were added, the phases were separated and the aqueous phase was extracted two times with ethyl acetate. The combined organic phases were concentrated in vacuo to give the following tetrahydroisoquinoline derivatives:

EXAMPLE 17

2-(1-Benzyl-3,4-dihydro-1H-isoquinolin-2-yl)-N-(2-methyl-benzyl)-acetamide:

prepared by reaction of 1-Benzyl-1,2,3,4-tetrahydroisoquinoline and 2-bromoacetyl bromide with 2-methylbenzylamine LC-MS: rt=4.6 min, 385 (M+1, ES+).

EXAMPLE 18

2-(1-Benzyl-3,4-dihydro-1H-isoquinolin-2-yl)-N-(2-chloro-benzyl)-acetamide:

prepared by reaction of 1-Benzyl-1,2,3,4-tetrahydroisoquinoline and 2-bromoacetyl bromide with 2-chlorobenzylamine LC-MS: rt=4.7 min, 405 (M+1, ES+).

EXAMPLE 19

2-(1-Benzyl-3,4-dihydro-1H-isoquinolin-2-yl)-N-(1-naphthalen-1-yl-ethyl)-acetamide:

prepared by reaction of 1-Benzyl-1,2,3,4-tetrahydroisoquinoline and 2-bromoacetyl bromide with 1-naphthaleneethylamine LC-MS: rt=4.7 and 4.8 min, 435 (M+1, ES+).

EXAMPLE 20

2-(1-Benzyl-3,4-dihydro-1H-isoquinolin-2-yl)-N-benzyl-N-methyl-acetamide:

prepared by reaction of 1-Benzyl-1,2,3,4-tetrahydroisoquinoline and 2-bromoacetyl bromide with N-benzylmethylamine LC-MS: rt=3.9 min, 385 (M+1, ES+).

EXAMPLE 21

2-[1-(3,4-Dimethoxy-benzyl)-6-methoxy-3,4-dihydro-1H-isoquinolin-2-yl]-N-(2-methoxy-benzyl)-acetamide:

prepared by reaction of 1-(3,4-dimethoxy-benzyl)-6-methoxy-1,2,3,4-tetrahydroisoquinoline and 2-bromoacetyl bromide with 2-methoxybenzylamine LC-MS: rt=4.0 min, 491 (M+1, ES+).

EXAMPLE 22

2-[1-(3,4-Dimethoxy-benzyl)-6-methoxy-3,4-dihydro-1H-isoquinolin-2-yl]-N-benzyl-acetamide:

prepared by reaction of 1-(3,4-dimethoxy-benzyl)-6-methoxy-1,2,3,4-tetrahydroisoquinoline and 2-bromoacetyl bromide with benzylamine LC-MS: rt=3.9 min, 461 (M+1, ES+).

EXAMPLE 23

2-[1-(3,4-Dimethoxy-benzyl)-6-methoxy-3,4-dihydro-1H-isoquinolin-2-yl]-N-(4-methoxy-benzyl)-acetamide:

prepared by reaction of 1-(3,4-dimethoxy-benzyl)-6-methoxy-1,2,3,4-tetrahydroisoquinoline and 2-bromoacetyl bromide with 4-methoxybenzylamine LC-MS: rt=3.9 min, 491 (M+1, ES+).

EXAMPLE 24

2-[1-(3,4-Dimethoxy-benzyl)-6-methoxy-3,4-dihydro-1H-isoquinolin-2-yl]-N-(naphthalen-1-yl-methyl)-acetamide:

prepared by reaction of 1-(3,4-dimethoxy-benzyl)-6-methoxy-1,2,3,4-tetrahydroisoquinoline and 2-bromoacetyl bromide with 1-napthalenemethylamine LC-MS: rt=4.3 min, 511 (M+1, ES+).

EXAMPLE 25

2-[1-(3,4-Dimethoxy-benzyl)-6-methoxy-3,4-dihydro-1H-isoquinolin-2-yl]-N-(3-methyl-benzyl)-acetamide:

prepared by reaction of 1-(3,4-dimethoxy-benzyl)-6-methoxy-1,2,3,4-tetrahydroisoquinoline and 2-bromoacetyl bromide with 3-methylbenzylamine LC-MS: rt=4.1 min, 475 (M+1, ES+).

EXAMPLE 26

2-[1-(3,4-Dimethoxy-benzyl)-6-methoxy-3,4-dihydro-1H-isoquinolin-2-yl]-N-(indan-1-yl)-acetamide:

prepared by reaction of 1-(3,4-dimethoxy-benzyl)-6-methoxy-1,2,3,4-tetrahydroisoquinoline and 2-bromoacetyl bromide with 1-amino-indane LC-MS: rt=4.2 min, 487 (M+1, ES+).

EXAMPLE 27

2-[1-(3,4-Dimethoxy-benzyl)-6-methoxy-3,4-dihydro-1H-isoquinolin-2-yl]-N-(1,2,3,4-tetrahydro-naphthalen-1-yl)-acetamide:

prepared by reaction of 1-(3,4-dimethoxy-benzyl)-6-methoxy-1,2,3,4-tetrahydroisoquinoline and 2-bromoacetyl bromide with 1,2,3,4-tetrahydro-1-naphthylamine LC-MS: rt=4.3 min, 501 (M+1, ES+).

EXAMPLE 28

2-[1-(3,4-Dimethoxy-benzyl)-6-methoxy-3,4-dihydro-1H-isoquinolin-2-yl]-N-(pyridin-3-yl-methyl)-acetamide:

prepared by reaction of 1-(3,4-dimethoxy-benzyl)6-methoxy-1,2,3,4-tetrahydroisoquinoline and 2-bromoacetyl bromide with 3-piconylamine LC-MS: rt=3.1 min 462 (M+1, ES+).

EXAMPLE 29

2-[1-(3,4-Dimethoxy-benzyl)-6-methoxy-3,4-dihydro-1H-isoquinolin-2-yl]-N-(pyridin-4-yl-methyl)-acetamide:

prepared by reaction of 1-(3,4-dimethoxy-benzyl)-6-methoxy-1,2,3,4-tetrahydroisoquinoline and 2-bromoacetyl bromide with 4-piconylamine LC-MS: rt=3.1 min, 462 (M+1, ES+).

EXAMPLE 30

2-[1-(3,4-Dimethoxy-benzyl)-6-methoxy-3,4-dihydro-1H-isoquinolin-2-yl]-N-(2-fluoro-benzyl)-acetamide:

prepared by reaction of 1-(3,4-dimethoxy-benzyl)-6-methoxy-1,2,3,4-tetrahydroisoquinoline and 2-bromoacetyl bromide with 2-fluorobenzylamine LC-MS: rt=4.0 min; 479 (M+1, ES+).

EXAMPLE 31

2-(1-Benzyl-6,7-dimethoxy-3,4-dihydro-1H-isoquinolin-2-yl)-N-benzyl-acetamide:

prepared by reaction of 1-benzyl-6,7-dimethoxy-1,2,3,4-tetrahydroisoquinoline and 2-bromoacetyl bromide with benzylamine LC-MS: rt=3.9 min, 431 (M+1, ES+).

EXAMPLE 32

2-(1-Benzyl-6,7-dimethoxy-3,4-dihydro-1H-isoquinolin-2-yl)-N-(indan-1-yl)-acetamide:

prepared by reaction of 1-benzyl-6,7-dimethoxy-1,2,3,4-tetrahydro-isoquinoline and 2-bromoacetyl bromide with 1-amino-indane LC-MS: rt=4.2 min, 457 (M+1, ES+).

EXAMPLE 33

2-(1-Benzyl-6,7-dimethoxy-3,4-dihydro-1H-isoquinolin-2-yl)-N-(1,2,3,4-tetrahydronaphthalen-1-yl)-acetamide:

prepared by reaction of 1-benzyl-6,7-dimethoxy-1,2,3,4-tetrahydro-isoquinoline and 2-bromoacetyl bromide with 1,2,3,4-tetrahydro-1-naphthylamine LC-MS: rt=4.3 min, 471 (M+1, ES+).

EXAMPLE 34

2-(1-Benzyl-6,7-dimethoxy-3,4-dihydro-1H-isoquinolin-2-yl)-N-(pyridin-3-yl-methyl)-acetamide:

prepared by reaction of 1-benzyl-6,7-dimethoxy-1,2,3,4-tetrahydroisoquinoline and 2-bromoacetyl bromide with 3-piconylamine LC-MS: rt=3.0 min, 432 (M+1, ES+).

EXAMPLE 35

2-(1-Benzyl-6,7-dimethoxy-3,4-dihydro-1H-isoquinolin-2-yl)-N-(2-methyl-benzyl)-acetamide:

prepared by reaction of 1-benzyl-6,7-dimethoxy-1,2,3,4-tetrahydroisoquinoline and 2-bromoacetyl bromide with 2-methylbenzylamine LC-MS: rt=4.1 min, 445 (M+1, ES+).

EXAMPLE 36

2-(1-Benzyl-6,7-dimethoxy-3,4-dihydro-1H-isoquinolin-2-yl)-N-(2,5-difluoro-benzyl)-acetamide:

prepared by reaction of 1-benzyl-6,7-dimethoxy-1,2,3,4-tetrahydroisoquinoline and 2-bromoacetyl bromide with 2,5-difluorobenzylamine LC-MS: rt=4.1 min, 467 (M+1, ES+).

EXAMPLE 37

2-(1-Benzyl-6,7-dimethoxy-3,4-dihydro-1H-isoquinolin-2-yl)-N-(4-fluoro-benzyl)-acetamide:

prepared by reaction of 1-benzyl-6,7-dimethoxy-1,2,3,4-tetrahydroisoquinoline and 2-bromoacetyl bromide with 4-fluorobenzylamine LC-MS: rt=4.0 min, 449 (M+1, ES+).

EXAMPLE 38

2-(1-Benzyl-6,7-dimethoxy-3,4-dihydro-1H-isoquinolin-2-yl)-N-(2-chloro-benzyl)-acetamide:

prepared by reaction of 1-benzyl-6,7-dimethoxy-1,2,3,4-tetrahydroisoquinoline and 2-bromoacetyl bromide with 2-chlorobenzylamine LC-MS: rt=4.2 min, 465 (M+1, ES+).

EXAMPLE 39

2-(1-Benzyl-6,7-dimethoxy-3,4-dihydro-1H-isoquinolin-2-yl)-N-(1-naphthalen-1-yl-ethyl)-acetamide:

prepared by reaction of 1-benzyl-6,7-dimethoxy-1,2,3,4-tetrahydro-isoquinoline and 2-bromoacetyl bromide with 1-naphthaleneethylamine LC-MS: rt=4.3 and 4.4 min, 495 (M+1, ES+).

EXAMPLE 40

2-(1-Benzyl-6,7-dimethoxy-3,4-dihydro-1H-isoquinolin-2-yl)-N-benzyl-N-methyl-acetamide:

prepared by reaction of 1-benzyl-6,7-dimethoxy-1,2,3,4-tetrahydroisoquinoline and 2-bromoacetyl bromide with N-benzylmethylamine LC-MS: rt=3.8 min, 445 (M+1, ES+).

EXAMPLE 41

2-[1-(3-Methoxy-benzyl)-6,7-dimethoxy-3,4-dihydro-1H-isoquinolin-2-yl]-N-(2-methoxy-benzyl)-acetamide:

prepared by reaction of 1-(3-Methoxy-benzyl)-6,7-dimethoxy-1,2,3,4-tetrahydro-isoquinoline and 2-bromoacetyl bromide with 2-methoxybenzylamine LC-MS: rt=4.0 min, 491 (M+1, ES+).

EXAMPLE 42

2-[1-(3-Methoxy-benzyl)-6,7-dimethoxy-3,4-dihydro-1H-isoquinolin-2-yl]-N-benzyl-acetamide:

prepared by reaction of 1-(3-Methoxy-benzyl)-6,7-dimethoxy-1,2,3,4-tetrahydro-isoquinoline and 2-bromoacetyl bromide with benzylamine LC-MS: rt=3.9 min, 461 (M+1, ES+).

EXAMPLE 43

2-[1-(3-Methoxy-benzyl)-6,7-dimethoxy-3,4-dihydro-1H-isoquinolin-2-yl]-N-(naphthalen-1-yl-methyl)-acetamide:

prepared by reaction of 1-(3-Methoxy-benzyl)-6,7-dimethoxy-1,2,3,4-tetrahydro-isoquinoline and 2-bromoacetyl bromide with naphthalen-1-yl-methylamine LC-MS: rt=4.3 min, 511 (M+1, ES+).

EXAMPLE 44

2-[1-(3-Methoxy-benzyl)-6,7-dimethoxy-3,4-dihydro-1H-isoquinolin-2-yl]-N-(3-methyl-benzyl)-acetamide:

prepared by reaction of 1-(3-Methoxy-benzyl)-6,7-dimethoxy-1,2,3,4-tetrahydro-isoquinoline and 2-bromoacetyl bromide with 3-methyl-benzylamine LC-MS: rt=4.1 min, 475 (M+1, ES+).

EXAMPLE 45

2-[1-(3-Methoxy-benzyl)-6,7-dimethoxy-3,4-dihydro-1H-isoquinolin-2-yl]-N-(indan-1-yl)-acetamide:

prepared by reaction of 1-(3-Methoxy-benzyl)-6,7-dimethoxy-1,2,3,4-tetrahydro-isoquinoline and 2-bromoacetyl bromide with 1-Aminoindan LC-MS: rt=4.2 min, 487 (M+1, ES+).

EXAMPLE 46

2-[1-(3-Methoxy-benzyl)-6,7-dimethoxy-3,4-dihydro-1H-isoquinolin-2-yl]-N-(1,2,3,4-tetrahydronaphthalen-1-yl)-acetamide:

prepared by reaction of 1-(3-Methoxy-benzyl)-6,7-dimethoxy-1,2,3,4-tetrahydro-isoquinoline and 2-bromoacetyl bromide with 1,2,3,4-tetrahydro-1-naphthylamine LC-MS: rt=4.3 min, 501 (M+1, ES+).

EXAMPLE 47

2-[1-(3-Methoxy-benzyl)-6,7-dimethoxy-3,4-dihydro-1H-isoquinolin-2-yl]-N-(pyridin-3-yl-methyl)-acetamide:

prepared by reaction of 1-(3-Methoxy-benzyl)-6,7-dimethoxy-1,2,3,4-tetrahydro-isoquinoline and 2-bromoacetyl bromide with 3-aminomethyl-pyridine LC-MS: rt=3.1 min, 462 (M+1, ES+).

EXAMPLE 48

2-[1-(3-Methoxy-benzyl)-6,7-dimethoxy-3,4-dihydro-1H-isoquinolin-2-yl]-N-(2-fluoro-benzyl)-acetamide:

prepared by reaction of 1-(3-Methoxy-benzyl)-6,7-dimethoxy-1,2,3,4-tetrahydro-isoquinoline and 2-bromoacetyl bromide with 2-fluoro-benzylamine LC-MS: rt=4.0 min, 479 (M+1, ES+).

EXAMPLE 49

2-[1-(4-Methoxy-benzyl)-6,7-dimethoxy-3,4-dihydro-1H-isoquinolin-2-yl]-N-benzyl-acetamide:

prepared by reaction of 1-(4-Methoxy-benzyl)-6,7-dimethoxy-1,2,3,4-tetrahydro-isoquinoline and 2-bromoacetyl bromide with benzylamine LC-MS: rt=3.9 min, 461 (M+1, ES+).

EXAMPLE 50

2-[1-(4-Methoxy-benzyl)-6,7-dimethoxy-3,4-dihydro-1H-isoquinolin-2-yl]-N-(naphthalen-1-yl-methyl)-acetamide:

prepared by reaction of 1-(4-Methoxy-benzyl)-6,7-dimethoxy-1,2,3,4-tetrahydro-isoquinoline and 2-bromoacetyl bromide with naphthalen-1-yl-methylamine LC-MS: rt=4.2 min, 511 (M+1, ES+).

EXAMPLE 51

2-[1-(4-Methoxy-benzyl)-6,7-dimethoxy-3,4-dihydro-1H-isoquinolin-2-yl]-N-(indan-1-yl)-acetamide:

prepared by reaction of 1-(4-Methoxy-benzyl)-6,7-dimethoxy-1,2,3,4-tetrahydro-isoquinoline and 2-bromoacetyl bromide with 1-Aminoindan LC-MS: rt=4.1 min, 487 (M+1, ES+).

EXAMPLE 52

2-[1-(4-Methoxy-benzyl)-6,7-dimethoxy-3,4-dihydro-1H-isoquinolin-2-yl]-N-(1,2,3,4-tetrahydronaphthalen-1-yl)-acetamide:

prepared by reaction of 1-(4-Methoxy-benzyl)-6,7-dimethoxy-1,2,3,4-tetrahydro-isoquinoline and 2-bromoacetyl bromide with 1,2,3,4-tetrahydro-1-naphthylamine LC-MS: rt=4.2 min, 501 (M+1, ES+).

EXAMPLE 53

2-[1-(4-Methoxy-benzyl)-6,7-dimethoxy-3,4-dihydro-1H-isoquinolin-2-yl]-N-(2-fluoro-benzyl)-acetamide:

prepared by reaction of 1-(4-Methoxy-benzyl)-6,7-dimethoxy-1,2,3,4-tetrahydro-isoquinoline and 2-bromoacetyl bromide with 2-fluoro-benzylamine LC-MS: rt=3.9 min, 479 (M+1, ES+).

EXAMPLE 54

2-[1-(3,4-Dimethoxy-benzyl)-6,7-dimethoxy-3,4-dihydro-1H-isoquinolin-2-yl]-N-(2-methoxy-benzyl)-acetamide:

prepared by reaction of 1-(3,4-Dimethoxy-benzyl)-6,7-dimethoxy-1,2,3,4-tetrahydroisoquinoline and 2-bromoacetyl bromide with 2-methoxybenzylamine LC-MS: rt=3.7 min, 521 (M+1, ES+).

EXAMPLE 55

2-[1-(3,4-Dimethoxy-benzyl)-6,7-dimethoxy-3,4-dihydro-1H-isoquinolin-2-yl]-N-(4-methoxy-benzyl)-acetamide:

prepared by reaction of 1-(3,4-Dimethoxy-benzyl)-6,7-dimethoxy-1,2,3,4-tetrahydroisoquinoline and 2-bromoacetyl bromide with 4-methoxybenzylamine LC-MS: rt=3.7 min, 521 (M+1, ES+).

EXAMPLE 56

2-[1-(3,4-Dimethoxy-benzyl)-6,7-dimethoxy-3,4-dihydro-1H-isoquinolin-2-yl]-N-(3-methyl-benzyl)-acetamide:

prepared by reaction of 1-(3,4-Dimethoxy-benzyl)-6,7-dimethoxy-1,2,3,4-tetrahydroisoquinoline and 2-bromoacetyl bromide with 3-methylbenzylamine LC-MS: rt=3.8 min, 505 (M+1, ES+).

EXAMPLE 57

2-[1-(3,4-Dimethoxy-benzyl)-6,7-dimethoxy-3,4-dihydro-1H-isoquinolin-2-yl]-N-(indan-1-yl)-acetamide:

prepared by reaction of 1-(3,4-Dimethoxy-benzyl)-6,7-dimethoxy-1,2,3,4-tetrahydroisoquinoline and 2-bromoacetyl bromide with 1-amino-indane LC-MS: rt=3.9 min. 517 (M+1, ES+).

EXAMPLE 58

2-[1-(3,4-Dimethoxy-benzyl)-6,7-dimethoxy-3,4-dihydro-1H-isoquinolin-2-yl]-N-(4-methyl-benzyl)-acetamide:

prepared by reaction of 1-(3,4-Dimethoxy-benzyl)-6,7-dimethoxy-1,2,3,4-tetrahydroisoquinoline and 2-bromoacetyl bromide with 4-methylbenzylamine LC-MS: rt=3.8 min, 505 (M+1, ES+).

EXAMPLE 59

2-[1-(3,4-Dimethoxy-benzyl)-6,7-dimethoxy-3,4-dihydro-1H-isoquinolin-2-yl]-N-(1,2,3,4-tetrahydro-naphthalen-1-yl)-acetamide:

prepared by reaction of 1-(3,4-Dimethoxy-benzyl)-6,7-dimethoxy-1,2,3,4-tetrahydroisoquinoline and 2-bromoacetyl bromide with 1,2,3,4-tetrahydro-1-naphthylamine LC-MS: rt=4.0 min, 531 (M+1, ES+).

EXAMPLE 60

2-[1-(3,4-Dimethoxy-benzyl)-6,7-dimethoxy-3,4-dihydro-1H-isoquinolin-2-yl]-N-(pyridin-3-yl-methyl)-acetamide:

prepared by reaction of 1-(3,4-Dimethoxy-benzyl)-6,7-dimethoxy-1,2,3,4-tetrahydroisoquinoline and 2-bromoacetyl bromide with 3-piconylamine LC-MS: rt=2.9 min, 492 (M+1, ES+).

EXAMPLE 61

2-[1-(3,4-Dimethoxy-benzyl)-6,7-dimethoxy-3,4-dihydro-1H-isoquinolin-2-yl]-N-(pyridin-4-yl-methyl)-acetamide:

prepared by reaction of 1-(3,4-Dimethoxy-benzyl)-6,7-dimethoxy-1,2,3,4-tetrahydroisoquinoline and 2-bromoacetyl bromide with 4-piconylamine LC-MS: rt=2.9 min, 492 (M+1, ES+).

EXAMPLE 62

2-[1-(3,4-Dimethoxy-benzyl)-6,7-dimethoxy-3,4-dihydro-1H-isoquinolin-2-yl]-N-phenyl-acetamide:

prepared by reaction of 1-(3,4-Dimethoxy-benzyl)-6,7-dimethoxy-1,2,3,4-tetrahydroisoquinoline and 2-bromoacetyl bromide with aniline LC-MS: rt=3.7 min, 477 (M+1, ES+).

EXAMPLE 63

2-[1-(3,4-Dimethoxy-benzyl)-6,7-dimethoxy-3,4-dihydro-1H-isoquinolin-2-yl]-N-(2-fluoro-benzyl)-acetamide:

prepared by reaction of 1-(3,4-Dimethoxy-benzyl)-6,7-dimethoxy-1,2,3,4-tetrahydroisoquinoline and 2-bromoacetyl bromide with 2-fluorobenzylamine LC-MS: rt=3.7 min, 509 (M+1, ES+).

EXAMPLE 64

2-[1-(3,4-Dimethoxy-benzyl)-6,7-dimethoxy-3,4-dihydro-1H-isoquinolin-2-yl]-N-[2-(4-methoxy-phenyl)-ethyl]-acetamide:

prepared by reaction of 1-(3,4-Dimethoxy-benzyl)-6,7-dimethoxy-1,2,3,4-tetrahydroisoquinoline and 2-bromoacetyl bromide with 4-methoxyphenylethylamine LC-MS: rt=3.8 min, 535 (M+1, ES+).

EXAMPLE 65

2-[1-(3,4-Dimethoxy-benzyl)-6,7-dimethoxy-3,4-dihydro-1H-isoquinolin-2-yl]-N-(2-methyl-benzyl)-acetamide:

prepared by reaction of 1-(3,4-Dimethoxy-benzyl)-6,7-dimethoxy-1,2,3,4-tetrahydroisoquinoline and 2-bromoacetyl bromide with 2-methylbenzylamine LC-MS: rt=3.9 min, 505 (M+1, ES+).

EXAMPLE 66

2-[1-(3,4-Dimethoxy-benzyl)-6,7-dimethoxy-3,4-dihydro-1H-isoquinolin-2-yl]-N-(2-trifluoromethyl-benzyl)-acetamide:

prepared by reaction of 1-(3,4-Dimethoxy-benzyl)-6,7-dimethoxy-1,2,3,4-tetrahydroisoquinoline and 2-bromoacetyl bromide with 2-trifluorobenzylamine LC-MS: rt=4.0 min, 559 (M+1, ES+).

EXAMPLE 67

2-[1-(3,4-Dimethoxy-benzyl)-6,7-dimethoxy-3,4-dihydro-1H-isoquinolin-2-yl]-N-(2,5-difluoro-benzyl)-acetamide:

prepared by reaction of 1-(3,4-Dimethoxy-benzyl)-6,7-dimethoxy-1,2,3,4-tetrahydroisoquinoline and 2-bromoacetyl bromide with 2,5-difluorobenzylamine LC-MS: rt=3.8 min, 527 (M+1, ES+).

EXAMPLE 68

2-[1-(3,4-Dimethoxy-benzyl)-6,7-dimethoxy-3,4-dihydro-1H-isoquinolin-2-yl]-N-(4-fluoro-benzyl)-acetamide:

prepared by reaction of 1-(3,4-Dimethoxy-benzyl)-6,7-dimethoxy-1,2,3,4-tetrahydroisoquinoline and 2-bromoacetyl bromide with 4-fluorobenzylamine LC-MS: rt=3.8 min, 509 (M+1, ES+).

EXAMPLE 69

2-[1-(3,4-Dimethoxy-benzyl)-6,7-dimethoxy-3,4-dihydro-1H-isoquinolin-2-yl]-N-(2-chloro-benzyl)-acetamide:

prepared by reaction of 1-(3,4-Dimethoxy-benzyl)-6,7-dimethoxy-1,2,3,4-tetrahydroisoquinoline and 2-bromoacetyl bromide with 2-chlorobenzylamine LC-MS: rt=3.9 min, 525 (M+1, ES+).

EXAMPLE 70

2-[1-(3,4-Dimethoxy-benzyl)-6,7-dimethoxy-3,4-dihydro-1H-isoquinolin-2-yl]-N-(2,4-dimethoxy-benzyl)-acetamide:

prepared by reaction of 1-(3,4-Dimethoxy-benzyl)-6,7-dimethoxy-1,2,3,4-tetrahydroisoquinoline and 2-bromoacetyl bromide with 2,4-dimethoxybenzylamine LC-MS: rt=3.8 min, 551 (M+1, ES+).

EXAMPLE 71

2-[1-(3,4-Dimethoxy-benzyl)-6,7-dimethoxy-3,4-dihydro-1H-isoquinolin-2-yl]-N-(1-phenyl-ethyl)-acetamide:

prepared by reaction of 1-(3,4-Dimethoxy-benzyl)-6,7-dimethoxy-1,2,3,4-tetrahydroisoquinoline and 2-bromoacetyl bromide with 1-phenylethylamine LC-MS: rt=3.7 min, 505 (M+1, ES+).

EXAMPLE 72

2-[1-(3,4-Dimethoxy-benzyl)-6,7-dimethoxy-3,4-dihydro-1H-isoquinolin-2-yl]-N-(1-naphthalen-1-yl-ethyl)-acetamide:

prepared by reaction of 1-(3,4-Dimethoxy-benzyl)-6,7-dimethoxy-1,2,3,4-tetrahydroisoquinoline and 2-bromoacetyl bromide with 1-naphthaleneethylamine LC-MS: rt=4.0 min, 555 (M+1, ES+).

EXAMPLE 73

2-[1-(3,4-Dimethoxy-benzyl)-6,7-dimethoxy-3,4-dihydro-1H-isoquinolin-2-yl]-N-benzyl-N-methyl-acetamide:

prepared by reaction of 1-(3,4-Dimethoxy-benzyl)-6,7-dimethoxy-1,2,3,4-tetrahydroisoquinoline and 2-bromoacetyl bromide with N-benzylmethylamine LC-MS: rt=3.6 min. 505 (M+1, ES+).

EXAMPLE 74

2-[1-(3,4-Dimethoxy-benzyl)-6,7-dimethoxy-3,4-dihydro-1H-isoquinolin-2-yl]-N-furan-2-yl-methyl-acetamide:

prepared by reaction of 1-(3,4-Dimethoxy-benzyl)-6,7-dimethoxy-1,2,3,4-tetrahydroisoquinoline and 2-bromoacetyl bromide with 1-aminomethylfurane LC-MS: rt=3.5 min, 481 (M+1, ES+).

EXAMPLE 75

2-[1-(3,4-Dimethoxy-benzyl)-6,7-dimethoxy-3,4-dihydro-1H-isoquinolin-2-yl]-N-but-2-yl-acetamide:

prepared by reaction of 1-(3,4-Dimethoxy-benzyl)-6,7-dimethoxy-1,2,3,4-tetrahydroisoquinoline and 2-bromoacetyl bromide with 2-butylamine LC-MS: rt=0.57 min, 457 (M+1, ES+).

EXAMPLE 76

2-[1-(3,4-Dimethoxy-benzyl)-6,7-dimethoxy-3,4-dihydro-1H-isoquinolin-2-yl]-N-(pyridin-2-yl-methyl)-acetamide:

prepared by reaction of 1-(3,4-Dimethoxy-benzyl)-6,7-dimethoxy-1,2,3,4-tetrahydroisoquinoline and 2-bromoacetyl bromide with 2-picolylamine LC-MS: rt=0.46 min, 492 (M+1, ES+).

EXAMPLE 77

2-[1-(3,4-Dimethoxy-benzyl)-6,7-dimethoxy-3,4-dihydro-1H-isoquinolin-2-yl]-N-(4-methoxy-indan-1-yl)-acetamide:

prepared by reaction of 1-(3,4-Dimethoxy-benzyl)-6,7-dimethoxy-1,2,3,4-tetrahydroisoquinoline and 2-bromoacetyl bromide with 1-amino-4-methoxy-indane LC-MS: rt=0.71 min, 547 (M+1, ES+).

EXAMPLE 78

2-[1-(3,4-Dimethoxy-benzyl)-6,7-dimethoxy-3,4-dihydro-1H-isoquinolin-2-yl]-N-(5,7-dimethyl-1,2,3,4-tetrahydro-naphthalen-1-yl)-acetamide:

prepared by reaction of 1-(3,4-Dimethoxy-benzyl)-6,7-dimethoxy-1,2,3,4-tetrahydroisoquinoline and 2-bromoacetyl bromide with 5,7-dimethyl-1,2,3,4-tetrahydro-1-naphthylamine LC-MS: rt=0.80 min, 559 (M+1, ES+).

EXAMPLE 79

2-[1-(3,4-Dimethoxy-benzyl)-6,7-dimethoxy-3,4-dihydro-1H-isoquinolin-2-yl]-N-(2-methyl-1,2,3,4-tetrahydro-naphthalen-1-yl)-acetamide:

prepared by reaction of 1-(3,4-Dimethoxy-benzyl)-6,7-dimethoxy-1,2,3,4-tetrahydroisoquinoline and 2-bromoacetyl bromide with 2-methyl-1,2,3,4-tetrahydro-1-naphthylamine LC-MS: rt=0.76 min, 545 (M+1, ES+).

EXAMPLE 80

2-[1-(3,4-Dimethoxy-benzyl)6,7-dimethoxy-3,4-dihydro-1H-isoquinolin-2-yl]-N-(6-methoxy-indan-1-yl)-acetamide:

prepared by reaction of 1-(3,4-Dimethoxy-benzyl)-6,7-dimethoxy-1,2,3,4-tetrahydroisoquinoline and 2-bromoacetyl bromide with 1-amino-6-methoxy-indane LC-MS: rt=0.72 min, 547 (M+1, ES+).

EXAMPLE 81

2-[1-(3,4-Dimethoxy-benzyl)-6,7-dimethoxy-3,4-dihydro-1H-isoquinolin-2-yl]-N-(6-methyl-indan-1-yl)-acetamide:

prepared by reaction of 1-(3,4-Dimethoxy-benzyl)-6,7-dimethoxy-1,2,3,4-tetrahydroisoquinoline and 2-bromoacetyl bromide with 1-amino-6-methyl-indane LC-MS: rt=0.74 min, 531 (M+1, ES+).

EXAMPLE 82

2-[1-(3,4-Dimethoxy-benzyl)-6,7-dimethoxy-3,4-dihydro-1H-isoquinolin-2-yl]-N-(5-fluoro-indan-1-yl)-acetamide:

prepared by reaction of 1-(3,4-Dimethoxy-benzyl)-6,7-dimethoxy-1,2,3,4-tetrahydroisoquinoline and 2-bromoacetyl bromide with 1-amino-5-fluoro-indane LC-MS: rt=0.72 min, 535 (M+1, ES+).

EXAMPLE 83

2-[1-(3,4-Dimethoxy-benzyl)-6,7-dimethoxy-3,4-dihydro-1H-isoquinolin-2-yl]-N-(5-methoxy-indan-1-yl)-acetamide:

prepared by reaction of 1-(3,4-Dimethoxy-benzyl)-6,7-dimethoxy-1,2,3,4-tetrahydroisoquinoline and 2-bromoacetyl bromide with 1-amino-5-methoxy-indane LC-MS: rt=0.75 min, 547 (M+1, ES+).

EXAMPLE 84

2-[1-(3,4-Dimethoxy-benzyl)-6,7-dimethoxy-3,4-dihydro-1H-isoquinolin-2-yl]-N-(4-methyl-indan-1-yl)-acetamide:

prepared by reaction of 1-(3,4-Dimethoxy-benzyl)-6,7-dimethoxy-1,2,3,4-tetrahydroisoquinoline and 2-bromoacetyl bromide with 1-amino-4-methyl-indane LC-MS: rt=0.86 min, 531 (M+1, ES+).

EXAMPLE 85

2-[1-(3,4-Dimethoxy-benzyl)-6,7-dimethoxy-3,4-dihydro-1H-isoquinolin-2-yl]-N-(3-methyl-indan-1-yl)-acetamide:

prepared by reaction of 1-(3,4-Dimethoxy-benzyl)-6,7-dimethoxy-1,2,3,4-tetrahydroisoquinoline and 2-bromoacetyl bromide with 1-amino-3-methyl-indane LC-MS: rt=0.85 min, 531 (M+1, ES+).

EXAMPLE 86

2-[(1S)-1-(3,4-Dimethoxy-benzyl)-6,7-dimethoxy-3,4-dihydro-1H-isoquinolin-2-yl]-N-[(1S)-indan-1-yl]-acetamide:

prepared by reaction of (1S)-1-(3,4-Dimethoxy-benzyl)-6,7-dimethoxy-1,2,3,4-tetrahydroisoquinoline and 2-bromoacetyl bromide with (1S)-1-amino-indane LC-MS: rt=3.8 min, 517 (M+1, ES+).

EXAMPLE 87

2-[(1S)-1-(3,4-Dimethoxy-benzyl)-6,7-dimethoxy-3,4-dihydro-1H-isoquinolin-2-yl]-N-[(1R)-indan-1-yl]-acetamide:

prepared by reaction of (1S)-1-(3,4-Dimethoxy-benzyl)-6,7-dimethoxy-1,2,3,4-tetrahydroisoquinoline and 2-bromoacetyl bromide with (1R)-1-amino-indane LC-MS: rt=3.9 min, 517 (M+1, ES+).

EXAMPLE 88

2-[(1S)-1-(3,4-Dimethoxy-benzyl)-6,7-dimethoxy-3,4-dihydro-1H-isoquinolin-2-yl]-N-(1,2,3,4-tetrahydronaphthalen-1-yl)-acetamide:

prepared by reaction of (1S)-1-(3,4-Dimethoxy-benzyl)-6,7-dimethoxy-1,2,3,4-tetrahydroisoquinoline and 2-bromoacetyl bromide with 1,2,3,4-tetrahydro-1-naphthylamine LC-MS: rt=4.0 min, 531 (M+1, ES+).

EXAMPLE 89

2-[(1S)-1-(3,4-Dimethoxy-benzyl)-6,7-dimethoxy-3,4-dihydro-1H-isoquinolin-2-yl]-N-benzyl-acetamide:

prepared by reaction of (1S)-1-(3,4-Dimethoxy-benzyl)-6,7-dimethoxy-1,2,3,4-tetrahydroisoquinoline and 2-bromoacetyl bromide with benzylamine LC-MS: rt=3.7 min, 491 (M+1, ES+).

EXAMPLE 90

2-[(1S)-1-(3,4-Dimethoxy-benzyl)-6,7-dimethoxy-3,4-dihydro-1H-isoquinolin-2-yl]-N-(naphthalen-1-yl-methyl)-acetamide:

prepared by reaction of (1S)-1-(3,4-Dimethoxy-benzyl)-6,7-dimethoxy-1,2,3,4-tetrahydroisoquinoline and 2-bromoacetyl bromide with naphthalen-1-yl-methylamine LC-MS: rt=4.0 min, 541 (M+1, ES+).

EXAMPLE 91

2-[(1S)-1-(3,4-Dimethoxy-benzyl)-6,7-dimethoxy-3,4-dihydro-1H-isoquinolin-2-yl]-N-(2-methoxy-benzyl)-acetamide:

prepared by reaction of (1S)-1-(3,4-Dimethoxy-benzyl)-6,7-dimethoxy-1,2,3,4-tetrahydroisoquinoline and 2-bromoacetyl bromide with 2-methoxy-benzylamine LC-MS: rt=3.7 min, 521 (M+1, ES+).

EXAMPLE 92

2-[(1S)-1-(3,4-Dimethoxy-benzyl)-6,7-dimethoxy-3,4-dihydro-1H-isoquinolin-2-yl]-N-(2-ethoxy-benzyl)-acetamide:

prepared by reaction of (1S)-1-(3,4-Dimethoxy-benzyl)-6,7-dimethoxy-1,2,3,4-tetrahydroisoquinoline and 2-bromoacetyl bromide with 2-ethoxy-benzylamine LC-MS: rt=4.0 min, 535 (M+1, ES+).

EXAMPLE 93

2-[(1S)-1-(3,4-Dimethoxy-benzyl)-6,7-dimethoxy-3,4-dihydro-1H-isoquinolin-2-yl]-N-benzyl-N-methyl-acetamide:

prepared by reaction of (1S)-1-(3,4-Dimethoxy-benzyl)-6,7-dimethoxy-1,2,3,4-tetrahydroisoquinoline and 2-bromoacetyl bromide with N-benzyl-N-methylamine LC-MS: rt=3.7 min, 505 (M+1, ES+).

EXAMPLE 94

2-[(1S)-1-(3,4-Dimethoxy-benzyl)-6,7-dimethoxy-3,4-dihydro-1H-isoquinolin-2-yl]-N-[(1R,2S)-2-hydroxy-indan-1-yl]-acetamide:

prepared by reaction of (1S)-1-(3,4-Dimethoxy-benzyl)-6,7-dimethoxy-1,2,3,4-tetrahydroisoquinoline and 2-bromoacetyl bromide with (1R,2S)-1-amino-2-indanol LC-MS: rt=3.5 min, 533 (M+1, ES+).

EXAMPLE 95

2-[(1S)-1-(3,4-Dimethoxy-benzyl)-6,7-dimethoxy-3,4-dihydro-1H-isoquinolin-2-yl]-N-[(1S,2R)-2-hydroxy-indan-1-yl]-acetamide:

prepared by reaction of (1S)-1-(3,4-Dimethoxy-benzyl)-6,7-dimethoxy-1,2,3,4-tetrahydroisoquinoline and 2-bromoacetyl bromide with (1S,2R)-1-amino-2-indanol LC-MS: rt=3.5 min, 533 (M+1, ES+).

EXAMPLE 96

2-[(1S)-1-(3,4-Dimethoxy-benzyl)-6,7-dimethoxy-3,4-dihydro-1H-isoquinolin-2-yl]-N-(pyridin-2-yl-methyl)-acetamide:

prepared by reaction of (1S)-1-(3,4-Dimethoxy-benzyl)-6,7-dimethoxy-1,2,3,4-tetrahydroisoquinoline and 2-bromoacetyl bromide with 2-picolylamine LC-MS: rt=3.1 min, 492 (M+1, ES+).

EXAMPLE 97

2-[(1S)-1-(3,4-Dimethoxy-benzyl)-6,7-dimethoxy-3,4-dihydro-11-isoquinolin-2-yl]-N-(2-phenyl-ethyl)-acetamide:

prepared by reaction of (1S)-1-(3,4-Dimethoxy-benzyl)-6,7-dimethoxy-1,2,3,4-tetrahydroisoquinoline and 2-bromoacetyl bromide with 2-phenyl-ethylamine LC-MS: rt=3.8 min, 505 (M+1, ES+).

EXAMPLE 98

2-[(1S)-1-(3,4-Dimethoxy-benzyl)-6,7-dimethoxy-3,4-dihydro-1H-isoquinolin-2-yl]-N-(cyclohexyl-methyl)-acetamide:

prepared by reaction of (1S)-1-(3,4-Dimethoxy-benzyl)-6,7-dimethoxy-1,2,3,4-tetrahydroisoquinoline and 2-bromoacetyl bromide with cyclohexyl-methylamine LC-MS: rt=4.0 min, 497 (M+1, ES+).

EXAMPLE 99

2-[1-(2,5-Dimethoxy-benzyl)-6,7-dimethoxy-3,4-dihydro-1H-isoquinolin-2-yl]-N-(4-methoxy-benzyl)-acetamide:

prepared by reaction of 1-(2,5-Dimethoxy-benzyl)-6,7-dimethoxy-1,2,3,4-tetrahydroisoquinoline and 2-bromoacetyl bromide with 4-methoxybenzylamine LC-MS: rt=3.9 min. 521 (M+1, ES+).

EXAMPLE 100

2-[1-(3,4-Dimethoxy-benzyl)-5,8-dimethoxy-3,4-dihydro-1H-isoquinolin-2-yl]-N-(2-methoxy-benzyl)-acetamide:

prepared by reaction of 1-(3,4-Dimethoxy-benzyl)-5,8-dimethoxy-1,2,3,4-tetrahydroisoquinoline and 2-bromoacetyl bromide with 2-methoxybenzylamine LC-MS: rt=4.3 min, 521 (M+1, ES+).

EXAMPLE 101

2-[1-(3,4-Dimethoxy-benzyl)-5,8-dimethoxy-3,4-dihydro-1H-isoquinolin-2-yl]-N-benzyl-acetamide:

prepared by reaction of 1-(3,4-Dimethoxy-benzyl)-5,8-dimethoxy-1,2,3,4,-tetrahydroisoquinoline and 2-bromoacetyl bromide with benzylamine LC-MS: rt=4.3 min, 491 (M+1, ES+).

EXAMPLE 102

2-[1-(3,4-Dimethoxy-benzyl)-5,8-dimethoxy-3,4-dihydro-1H-isoquinolin-2-yl]-N-[2-(3,4-dimethoxy-phenyl)-ethyl]-acetamide:

prepared by reaction of 1-(3,4-Dimethoxy-benzyl)-5,8-dimethoxy-1,2,3,4-tetrahydroisoquinoline and 2-bromoacetyl bromide with 3,4-dimethoxyphenylethylamine LC-MS: rt=4.3 min, 565 (M+1, ES+).

EXAMPLE 103

2-[1-(3,4-Dimethoxy-benzyl)-5,8-dimethoxy-3,4-dihydro-1H-isoquinolin-2-yl]-N-(indan-1-yl)-acetamide:

prepared by reaction of 1-(3,4-Dimethoxy-benzyl)-5,8-dimethoxy-1,2,3,4-tetrahydroisoquinoline and 2-bromoacetyl bromide with 1-amino-indane LC-MS: rt=4.5 min, 517 (M+1, ES+).

EXAMPLE 104

2-[1-(3,4-Dimethoxy-benzyl)-5,8-dimethoxy-3,4-dihydro-1H-isoquinolin-2-yl]-N-(pyridin-3-yl-methyl)-acetamide:

prepared by reaction of 1-(3,4-Dimethoxy-benzyl)-5,8-dimethoxy-1,2,3,4-tetrahydroisoquinoline and 2-bromoacetyl bromide with 3-picolylamine LC-MS: rt=3.4 min, 492 (M+1, ES+).

EXAMPLE 105

2-[1-(3,4-Dimethoxy-benzyl)-5,8-dimethoxy-3,4-dihydro-1-isoquinolin-2-yl]-N-butyl-acetamide:

prepared by reaction of 1-(3,4-Dimethoxy-benzyl)-5,8-dimethoxy-1,2,3,4-tetrahydroisoquinoline and 2-bromoacetyl bromide with n-butylamine LC-MS: rt=4.2 min, 457 (M+1, ES+).

EXAMPLE 106

2-[1-(3,4-Dimethoxy-benzyl)-5,8-dimethoxy-3,4-dihydro-1H-isoquinolin-2-yl]-N-(2-fluoro-benzyl)-acetamide:

prepared by reaction of 1-(3,4-Dimethoxy-benzyl)-5,8-dimethoxy-1,2,3,4-tetrahydroisoquinoline and 2-bromoacetyl bromide with 2-fluorobenzylamine LC-MS: rt=4.4 min, 509 (M+1, ES+).

EXAMPLE 107

2-[1-(3,4-Dimethoxy-benzyl)-5,8-dimethoxy-3,4-dihydro-1H-isoquinolin-2-yl]-N-(pyridin-2-yl-methyl)-acetamide:

prepared by reaction of 1-(3,4-Dimethoxy-benzyl)-5,8-dimethoxy-1,2,3,4-tetrahydroisoquinoline and 2-bromoacetyl bromide with 2-picolylamine LC-MS: rt=3.7 min, 492 (M+1, ES+).

EXAMPLE 108

2-[1-(3,4-Dimethoxy-benzyl)-5,8-dimethoxy-3,4-dihydro-1H-isoquinolin-2-yl]-N-[1,3,4]thiadiazol-2-yl-acetamide:

prepared by reaction of 1-(3,4-Dimethoxy-benzyl)-5,8-dimethoxy-1,2,3,4-tetrahydroisoquinoline and 2-bromoacetyl bromide with 2-amino-1,3,4-thiadiazole LC-MS: rt=3.8 min, 485 (M+1, ES+).

EXAMPLE 109

2-[1-(3,4-Dimethoxy-benzyl)-5,8-dimethoxy-3,4-dihydro-1H-isoquinolin-2-yl]-N-(1H-benzoimidazol-2-yl-methyl)-acetamide:

prepared by reaction of 1-(3,4-Dimethoxy-benzyl)-5,8-dimethoxy-1,2,3,4-tetrahydroisoquinoline and 2-bromoacetyl bromide with 2-(aminomethyl)-benzimidazole LC-MS: rt=3.4 min, 531 (M+1, ES+).

EXAMPLE 110

2-[1-(2-Phenyl-ethyl)-6,7-dimethoxy-3,4-dihydro-1H-isoquinolin-2-yl]-N-(pyridin-3-yl-methyl)-acetamide:

prepared by reaction of 1-(2-Phenyl-ethyl)-6,7-dimethoxy-1,2,3,4-tetrahydroisoquinoline and 2-bromoacetyl bromide with 3-picolylamine LC-MS: rt=2.7 min, 446 (M+1, ES+).

EXAMPLE 111

2-[1-(2-Phenyl-ethyl)-6,7-dimethoxy-3,4-dihydro-1H-isoquinolin-2-yl]-N-(2-fluoro-benzyl)-acetamide:

prepared by reaction of 1-(2-Phenyl-ethyl)-6,7-dimethoxy-1,2,3,4-tetrahydroisoquinoline and 2-bromoacetyl bromide with 2-fluorobenzylamine LC-MS: rt=4.0 min, 463 (M+1, ES+).

EXAMPLE 112

2-[1-(2-Phenyl-ethyl)-6,7-dimethoxy-3,4-dihydro-1H-isoquinolin-2-yl]-N-cyclohexyl-acetamide:

prepared by reaction of 1-(2-Phenyl-ethyl)-6,7-dimethoxy-1,2,3,4-tetrahydroisoquinoline and 2-bromoacetyl bromide with cyclohexylamine LC-MS: rt=4.0 min, 437 (M+1, ES+).

EXAMPLE 113

2-[1-(1-Phenyl-propyl)-6,7-dimethoxy-3,4-dihydro-1H-isoquinolin-2-yl]-N-benzyl-acetamide:

prepared by reaction of 1-(1-Phenyl-propyl)-6,7-dimethoxy-1,2,3,4-tetrahydroisoquinoline and 2-bromoacetyl bromide with benzylamine LC-MS: rt=4.4 min, 459 (M+1, ES+).

EXAMPLE 114

2-[1-(1-Phenyl-propyl)-6,7-dimethoxy-3,4-dihydro-1H-isoquinolin-2-yl]-N-(pyridin-2-yl-methyl)-acetamide:

prepared by reaction of 1-(1-Phenyl-propyl)-6,7-dimethoxy-1,2,3,4-tetrahydroisoquinoline and 2-bromoacetyl bromide with 2-picolylamine LC-MS: rt=3.7 min, 460 (M+1, ES+).

EXAMPLE 115

2-[1-(Diphenyl-methyl)-5,8-dimethoxy-3,4-dihydro-1H-isoquinolin-2-yl]-N-(2-methoxy-benzyl)-acetamide:

prepared by reaction of 1-(Diphenyl-methyl)-5,8-dimethoxy-1,2,3,4-tetrahydroisoquinoline and 2-bromoacetyl bromide with 2-methoxy-benzylamine LC-MS: rt=5.2 min, 537 (M+1, ES+).

EXAMPLE 116

2-[1-(Diphenyl-methyl)-5,8-dimethoxy-3,4-dihydro-1H-isoquinolin-2-yl]-N-(pyridin-2-yl-methyl)-acetamide:

prepared by reaction of 1-(Diphenyl-methyl)-5,8-dimethoxy-1,2,3,4-tetrahydroisoquinoline and 2-bromoacetyl bromide with 2-picolylamine LC-MS: rt=4.3 min, 508 (M+1, ES+).

EXAMPLE 117

2-[1-(2,5-Dimethoxy-benzyl)-5,8-dimethoxy-3,4-dihydro-1H-isoquinolin-2-yl]-N-(indan-1-yl)-acetamide:

prepared by reaction of 1-(2,5-Dimethoxy-benzyl)-5,8-dimethoxy-1,2,3,4-tetrahydroisoquinoline and 2-bromoacetyl bromide with 1-amino-indane LC-MS: rt=4.6 min, 517 (M+1, ES+).

EXAMPLE 118

2-[1-(2,5-Dimethoxy-benzyl)-5,8-dimethoxy-3,4-dihydro-1H-isoquinolin-2-yl]-N-benzyl-acetamide:

prepared by reaction of 1-(2,5-Dimethoxy-benzyl)-5,8-dimethoxy-1,2,3,4-tetrahydroisoquinoline and 2-bromoacetyl bromide with benzylamine LC-MS: rt=4.4 min, 491 (M+1, ES+).

EXAMPLE 119

2-[1-(2,5-Dimethoxy-benzyl)-5,8-dimethoxy-3,4-dihydro-1H-isoquinolin-2-yl]-N-(2-methoxy-benzyl)-acetamide:

prepared by reaction of 1-(2,5-Dimethoxy-benzyl)-5,8-dimethoxy-1,2,3,4-tetrahydroisoquinoline and 2-bromoacetyl bromide with 2-methoxy-benzyl-amine LC-MS: rt=4.5 min, 521 (M+1, ES+).

EXAMPLE 120

2-[1-(2,5-Dimethoxy-benzyl)-5,8-dimethoxy-3,4-dihydro-1H-isoquinolin-2-yl]-N-(2-ethoxy-benzyl)-acetamide:

prepared by reaction of 1-(2,5-Dimethoxy-benzyl)-5,8-dimethoxy-1,2,3,4-tetrahydroisoquinoline and 2-bromoacetyl bromide with 2-ethoxy-benzyl-amine LC-MS: rt=4.6 min, 535 (M+1, ES+).

EXAMPLE 121

2-[1-(2,5-Dimethoxy-benzyl)-5,8-dimethoxy-3,4-dihydro-1H-isoquinolin-2-yl]-N-[(1R,2S)-2-hydroxy-indan-1-yl]-acetamide:

prepared by reaction of 1-(2,5-Dimethoxy-benzyl)-5,8-dimethoxy-1,2,3,4-tetrahydroisoquinoline and 2-bromoacetyl bromide with (1R,2S)-1-amino-2-indanol LC-MS: rt=4.1 min, 533 (M+1, ES+).

EXAMPLE 122

2-[1-(2,5-Dimethoxy-benzyl)-5,8-dimethoxy-3,4-dihydro-1H-isoquinolin-2-yl]-N-[(1S,2R)-2-hydroxy-indan-1-yl]-acetamide:

prepared by reaction of 1-(2,5-Dimethoxy-benzyl)-5,8-dimethoxy-1,2,3,4-tetrahydroisoquinoline and 2-bromoacetyl bromide with (1S,2R)-1-amino-2-indanol LC-MS: rt=4.1 min, 533 (M+1, ES+).

EXAMPLE 123

2-[1-(2,5-Dimethoxy-benzyl)-5,8-dimethoxy-3,4-dihydro-1H-isoquinolin-2-yl]-N-(pyridin-2-yl-methyl)-acetamide:

prepared by reaction of 1-(2,5-Dimethoxy-benzyl)-5,8-dimethoxy-1,2,3,4-tetrahydroisoquinoline and 2-bromoacetyl bromide with 2-picolylamine LC-MS: rt=3.8 min, 492 (M+1, ES+).

EXAMPLE 124

2-[1-(2,5-Dimethoxy-benzyl)-5,8-dimethoxy-3,4-dihydro-1H-isoquinolin-2-yl]-N-(indan-2-yl)-acetamide:

prepared by reaction of 1-(2,5-Dimethoxy-benzyl)-5,8-dimethoxy-1,2,3,4-tetrahydroisoquinoline and 2-bromoacetyl bromide with 2-amino-indane LC-MS: rt=4.6 min, 517 (M+1, ES+).

EXAMPLE 125

2-[1-(4-Chloro-benzyl)-6,7-dimethoxy-3,4-dihydro-1H-isoquinolin-2-yl]-N-(indan-1-yl)-acetamide:

prepared by reaction of 1-(4-Chloro-benzyl)-6,7-dimethoxy-1,2,3,4-tetrahydroisoquinoline and 2-bromoacetyl bromide with 1-amino-indane LC-MS: rt=4.8 min, 491 (M+1, ES+).

EXAMPLE 126

2-[1-(4-Chloro-benzyl)-6,7-dimethoxy-3,4-dihydro-1H-isoquinolin-2-yl]-N-benzyl-acetamide:

prepared by reaction of 1-(4-Chloro-benzyl)-6,7-dimethoxy-1,2,3,4-tetrahydroisoquinoline and 2-bromoacetyl bromide with benzylamine LC-MS: rt=4.4 min. 465 (M+1, ES+).

EXAMPLE 127

2-[1-(4-Chloro-benzyl)-6,7-dimethoxy-3,4-dihydro-1H-isoquinolin-2-yl]-N-(2-ethoxy-benzyl)-acetamide:

prepared by reaction of 1-(4-Chloro-benzyl)-6,7-dimethoxy-1,2,3,4-tetrahydroisoquinoline and 2-bromoacetyl bromide with 2-ethoxy-benzylamine LC-MS: rt=4.7 min, 509 (M+1, ES+).

EXAMPLE 128

2-[1-(4-Chloro-benzyl)-6,7-dimethoxy-3,4-dihydro-1H-isoquinolin-2-yl]-N-[(1R,2S)-2-hydroxy-indan-1-yl]-acetamide:

prepared by reaction of 1-(4-Chloro-benzyl)-6,7-dimethoxy-1,2,3,4-tetrahydroisoquinoline and 2-bromoacetyl bromide with (1R,2S)-1-amino-2-indanol LC-MS: rt=4.0 min, 507 (M+1, ES+), 505 (M−1, ES−).

EXAMPLE 129

2-[1-(4-Chloro-benzyl)-6,7-dimethoxy-3,4-dihydro-1H-isoquinolin-2-yl]-N-(pyridin-2-yl-methyl)-acetamide:

prepared by reaction of 1-(4-Chloro-benzyl)-6,7-dimethoxy-1,2,3,4-tetrahydroisoquinoline and 2-bromoacetyl bromide with 2-picolylamine LC-MS: rt=3.6 min, 466 (M+1, ES+).

EXAMPLE 130

2-[1-(4-Chloro-benzyl)-6,7-dimethoxy-3,4-dihydro-1H-isoquinolin-2-yl]-N-(indan-2-yl)-acetamide:

prepared by reaction of 1-(4-Chloro-benzyl)-6,7-dimethoxy-1,2,3,4-tetrahydroisoquinoline and 2-bromoacetyl bromide with 2-amino-indane LC-MS: rt=4.5 min, 491 (M+1, ES+).

EXAMPLE 131

2-(1-Benzyl-5,8-dimethoxy-3,4-dihydro-1H-isoquinolin-2-yl)-N-[(1S,2R)-2-hydroxy-indan-1-yl)-acetamide:

prepared by reaction of 1-Benzyl-5,8-dimethoxy-1,2,3,4-tetrahydro-isoquinoline and 2-bromoacetyl bromide with (1S,2R)-1-amino-2-indanol LC-MS: rt=4.2 min, 473 (M+1, ES+).

EXAMPLE 132

2-[1-(3,4-Dimethoxy-benzyl)-6-methoxy-7-isopropoxy-3,4-dihydro-1H-isoquinolin-2-yl]-N-[(1S)-indan-1-yl]-acetamide:

prepared by reaction of 1-3,4-Dimethoxy-benzyl)-6-methoxy-7-isopropoxy-1,2,3,4-tetrahydroisoquinoline and 2-bromoacetyl bromide with (1S)-1-amino-indane LC-MS: rt=4.1 min, 545 (M+1, ES+).

EXAMPLE 133

2-[1-(3,4-Dimethoxy-benzyl)-6-methoxy-7-isopropoxy-3,4-dihydro-1H-isoquinolin-2-yl]-N-(1,2,3,4-tetrahydronaphthalen-1-yl)-acetamide:

prepared by reaction of 1-(3,4-Dimethoxy-benzyl)-6-methoxy-7-isopropoxy-1,2,3,4-tetrahydroisoquinoline and 2-bromoacetyl bromide with 1,2,3,4-tetrahydro-1-naphthylamine LC-MS: rt=4.3 min, 559 (M+1, ES+).

EXAMPLE 134

2-[1-(3,4-Dimethoxy-benzyl)-6-methoxy-7-isopropoxy-3,4-dihydro-1H-isoquinolin-2-yl]-N-benzyl-acetamide:

prepared by reaction of 1-(3,4-Dimethoxy-benzyl)-6-methoxy-7-isopropoxy-1,2,3,4-tetrahydroisoquinoline and 2-bromoacetyl bromide with benzylamine LC-MS: rt=3.9 min, 519 (M+1, ES+).

EXAMPLE 135

2-[1-(3,4-Dimethoxy-benzyl)-6-methoxy-7-isopropoxy-3,4-dihydro-1H-isoquinolin-2-yl]-N-(naphthalen-1-yl-methyl)-acetamide:

prepared by reaction of 1-(3,4-Dimethoxy-benzyl)-6-methoxy-7-isopropoxy-1,2,3,4-tetrahydroisoquinoline and 2-bromoacetyl bromide with naphthalen-1-yl-methylamine LC-MS: rt=4.3 min, 569 (M+1, ES+).

EXAMPLE 136

2-[1-(3,4-Dimethoxy-benzyl)-6-methoxy-7-isopropoxy-3,4-dihydro-1H-isoquinolin-2-yl]-N-(2-methoxy-benzyl)-acetamide:

prepared by reaction of 1-(3,4-Dimethoxy-benzyl)-6-methoxy-7-isopropoxy-1,2,3,4-tetrahydroisoquinoline and 2-bromoacetyl bromide with 2-methoxy-benzylamine LC-MS: rt=4.0 min, 549 (M+1, ES+).

EXAMPLE 137

2-[1-(3,4-Dimethoxy-benzyl)-6-methoxy-7-isopropoxy-3,4-dihydro-1H-isoquinolin-2-yl]-N-(2-ethoxy-benzyl)-acetamide:

prepared by reaction of 1-(3,4-Dimethoxy-benzyl)-6-methoxy-7-isopropoxy-1,2,3,4-tetrahydroisoquinoline and 2-bromoacetyl bromide with 2-ethoxy-benzylamine LC-MS: rt=4.2 min, 563 (M+1, ES+).

EXAMPLE 138

2-[1-(3,4-Dimethoxy-benzyl)-6-methoxy-7-isopropoxy-3,4-dihydro-1H-isoquinolin-2-yl]-N-[(1R)-indan-1-yl]-acetamide:

prepared by reaction of 1-(3,4-Dimethoxy-benzyl)-6-methoxy-7-isopropoxy-1,2,3,4-tetrahydroisoquinoline and 2-bromoacetyl bromide with (1R)-1-amino-indane LC-MS: rt=4.1 min, 545 (M+1, ES+).

EXAMPLE 139

2-[1-(3,4-Dimethoxy-benzyl)-6-methoxy-7-isopropoxy-3,4-dihydro-1H-isoquinolin-2-yl]-N-benzyl-N-methyl-acetamide:

prepared by reaction of 1-(3,4-Dimethoxy-benzyl)-6-methoxy-7-isopropoxy-1,2,3,4-tetrahydroisoquinoline and 2-bromoacetyl bromide with N-benzyl-N-methyl-amine LC-MS: rt=3.9 min, 533 (M+1, ES+).

EXAMPLE 140

2-[1-(3,4-Dimethoxy-benzyl)-6-methoxy-7-isopropoxy-3,4-dihydro-1H-isoquinolin-2-yl]-N-(1,2,3,4-tetrahydronaphthalen-1-y)-acetamide:

prepared by reaction of 1-(3,4-Dimethoxy-benzyl)-6-methoxy-7-isopropoxy-1,2,3,4-tetrahydroisoquinoline and 2-bromoacetyl bromide with 1,2,3,4-tetrahydro-1-naphthylamine LC-MS: rt=4.0 min, 545 (M+1, ES+).

EXAMPLE 141

2-[1-(3,4-Dimethoxy-benzyl)-6-methoxy-7-isopropoxy-3,4-dihydro-1H-isoquinolin-2-yl]-N-(pyridin-2-yl-methyl)-acetamide:

prepared by reaction of 1-(3,4-Dimethoxy-benzyl)-6-methoxy-7-isopropoxy-1,2,3,4-tetrahydroisoquinoline and 2-bromoacetyl bromide with 2-picolylamine LC-MS: rt=3.4 min, 520 (M+1, ES+).

EXAMPLE 142

2-[1-(3,4-Dimethoxy-benzyl)-6-methoxy-7-isopropoxy-3,4-dihydro-1H-isoquinolin-2-yl]-N-[(1S,2R)-2-hydroxy-indan-1-yl]-acetamide:

prepared by reaction of 1-(3,4-Dimethoxy-benzyl)-6-methoxy-7-isopropoxy-1,2,3,4-tetrahydroisoquinoline and 2-bromoacetyl bromide with (1S,2R)-1-amino-2-indanol LC-MS: rt=3.8 min, 561 (M+1, ES+).

EXAMPLE 143

2-[1-(3,4-Dimethoxy-benzyl)-6-methoxy-7-isopropoxy-3,4-dihydro-1H-isoquinolin-2-yl]-N-(2-phenyl-ethyl)-acetamide:

prepared by reaction of 1-(3,4-Dimethoxy-benzyl)-6-methoxy-7-isopropoxy-1,2,3,4-tetrahydroisoquinoline and 2-bromoacetyl bromide with 2-phenyl-ethylamine LC-MS: rt=4.0 min, 533 (M+1, ES+).

EXAMPLE 144

2-[1-(3,4-Dimethoxy-benzyl)-6-methoxy-7-isopropoxy-3,4-dihydro-1H-isoquinolin-2-yl]-N-cyclohexyl-methyl-acetamide:

prepared by reaction of 1-(3,4-Dimethoxy-benzyl)-6-methoxy-7-isopropoxy-1,2,3,4-tetrahydroisoquinoline and 2-bromoacetyl bromide with cyclohexyl-methylamine LC-MS: rt=4.2 min, 525 (M+1, ES+).

EXAMPLE 145

2-[1-(3,4-Dimethoxy-benzyl)-6-methoxy-7-isopropoxy-3,4-dihydro-1H-isoquinolin-2-yl]-N-(5,7-dimethyl-1,2,3,4-tetrahydronaphthalen-1-yl)-acetamide:

prepared by reaction of 1-(3,4-Dimethoxy-benzyl)-6-methoxy-7-isopropoxy-1,2,3,4-tetrahydroisoquinoline and 2-bromoacetyl bromide with 5,7-dimethyl-1,2,3,4-tetrahydro-1-naphthylamine LC-MS: rt=0.84 min, 587 (M+1, ES+).

EXAMPLE 146

2-[1-(3,4-Dimethoxy-benzyl)-6-methoxy-7-isopropoxy-3,4-dihydro-1H-isoquinolin-2-yl]-N-(2-methyl-1,2,3,4-tetrahydronaphthalen-1-yl)-acetamide:

prepared by reaction of 1-(3,4-Dimethoxy-benzyl)-6-methoxy-7-isopropoxy-1,2,3,4-tetrahydroisoquinoline and 2-bromoacetyl bromide with 2-methyl-1,2,3,4-tetrahydro-1-naphthylamine LC-MS: rt=0.81 min, 573 (M+1, ES+).

EXAMPLE 147

2-[1-(3,4-Dimethoxy-benzyl)-6-methoxy-7-isopropoxy-3,4-dihydro-1H-isoquinolin-2-yl]-N-(4-methyl-indan-1-yl)-acetamide:

prepared by reaction of 1-(3,4-Dimethoxy-benzyl)-6-methoxy-7-isopropoxy-1,2,3,4-tetrahydroisoquinoline and 2-bromoacetyl bromide with 1-amino-4-methyl-indane LC-MS: rt=0.79 min, 559 (M+1, ES+).

EXAMPLE 148

2-[1-(3,4-Dimethoxy-benzyl)-6-methoxy-7-isopropoxy-3,4-dihydro-1H-isoquinolin-2-yl]-N-(4-methyl-1,2,3,4-tetrahydronaphthalen-1-yl)-acetamide:

prepared by reaction of 1-(3,4-Dimethoxy-benzyl)-6-methoxy-7-isopropoxy-1,2,3,4-tetrahydroisoquinoline and 2-bromoacetyl bromide with 4-methyl-1,2,3,4-tetrahydro-1-naphthylamine LC-MS: rt=0.81 min, 573 (M+1, ES+).

EXAMPLE 149

2-[1-(3,4-Dimethoxy-benzyl)-6-methoxy-7-isopropoxy-3,4-dihydro-1H-isoquinolin-2-yl]-N-(6-methoxy-indan-1-yl)-acetamide:

prepared by reaction of 1-(3,4-Dimethoxy-benzyl)-6-methoxy-7-isopropoxy-1,2,3,4-tetrahydroisoquinoline and 2-bromoacetyl bromide with 1-amino-6-methoxy-indane LC-MS: rt=0.77 min, 575 (M+1, ES+).

EXAMPLE 150

2-[1-(3,4-Dimethoxy-benzyl)-6-methoxy-7-isopropoxy-3,4-dihydro-1H-isoquinolin-2-yl]-N-(6-methyl-indan-1-yl)-acetamide:

prepared by reaction of 1-(3,4-Dimethoxy-benzyl)-6-methoxy-7-isopropoxy-1,2,3,4-tetrahydroisoquinoline and 2-bromoacetyl bromide with 1-amino-6-methyl-indane LC-MS: rt=0.80 min. 559 (M+1, ES+).

EXAMPLE 151

2-[1-(3,4-Dimethoxy-benzyl)-6-methoxy-7-isopropoxy-3,4-dihydro-1H-isoquinolin-2-yl]-N-(5-fluoro-indan-1-yl)-acetamide:

prepared by reaction of 1-(3,4-Dimethoxy-benzyl)-6-methoxy-7-isopropoxy-1,2,3,4-tetrahydroisoquinoline and 2-bromoacetyl bromide with 1-amino-5-fluoro-indane LC-MS: rt=0.78 min, 563 (M+1, ES+).

EXAMPLE 152

2-[1-(3,4-Dimethoxy-benzyl)-6-methoxy-7-isopropoxy-3,4-dihydro-1H-isoquinolin-2-yl]-N-(2-methyl-indan-1-yl)-acetamide:

prepared by reaction of 1-(3,4-Dimethoxy-benzyl)-6-methoxy-7-isopropoxy-1,2,3,4-tetrahydroisoquinoline and 2-bromoacetyl bromide with 1-amino-2-methyl-indane LC-MS: rt=0.79 min, 559 (M+1, ES+).

EXAMPLE 153

2-[1-(3,4-Dimethoxy-benzyl)-6-methoxy-7-isopropoxy-3,4-dihydro-1H-isoquinolin-2-yl]-N-(3-methyl-indan-1-yl)-acetamide:

prepared by reaction of 1-(3,4-Dimethoxy-benzyl)-6-methoxy-7-isopropoxy-1,2,3,4-tetrahydroisoquinoline and 2-bromoacetyl bromide with 1-amino-3-methyl-indane LC-MS: rt=0.79 min, 559 (M+1, ES+).

EXAMPLE 154

2-[1-(3,4-Dimethoxy-benzyl)-6-methoxy-7-isopropoxy-3,4-dihydro-1H-isoquinolin-2-yl]-N-(3-phenyl-indan-1-yl)-acetamide:

prepared by reaction of 1-(3,4-Dimethoxy-benzyl)-6-methoxy-7-isopropoxy-1,2,3,4-tetrahydroisoquinoline and 2-bromoacetyl bromide with 1-amino-3-phenyl-indane LC-MS: rt=0.86 min, 621 (M+1, ES+).

EXAMPLE 155

2-[1-(3,4-Dimethoxy-benzyl)-6-methoxy-7-isopropoxy-3,4-dihydro-1H-isoquinolin-2-yl]-N-(5,6-dimethoxy-indan-1-yl)-acetamide:

prepared by reaction of 1-(3,4-Dimethoxy-benzyl)-6-methoxy-7-isopropoxy-1,2,3,4-tetrahydroisoquinoline and 2-bromoacetyl bromide with 1-amino-5,6-dimethoxy-indane LC-MS: rt=0.72 min, 605 (M+1, ES+).

EXAMPLE 156

2-[1-(3,4-Dimethoxy-benzyl)-6-methoxy-7-isopropoxy-3,4-dihydro-1H-isoquinolin-2-yl]-N-(5-methoxy-indan-1-yl)-acetamide:

prepared by reaction of 1-(3,4-Dimethoxy-benzyl)-6-methoxy-7-isopropoxy-1,2,3,4-tetrahydroisoquinoline and 2-bromoacetyl bromide with 1-amino-5-methoxy-indane LC-MS: rt=0.76 min, 575 (M+1, ES+).

EXAMPLE 157

2-[1-(3,4-Dimethoxy-benzyl)-6-methoxy-7-isopropoxy-3,4-dihydro-1H-isoquinolin-2-yl]-N-(5-bromo-indan-1-yl)-acetamide:

prepared by reaction of 1-(3,4-Dimethoxy-benzyl)-6-methoxy-7-isopropoxy-1,2,3,4-tetrahydroisoquinoline and 2-bromoacetyl bromide with 1-amino-5-bromo-indane LC-MS: rt=0.82 min, 623 (M+1, ES+).

EXAMPLE 158

2-[1-(3,4-Dimethoxy-benzyl)-6-methoxy-7-isopropoxy-3,4-dihydro-1H-isoquinolin-2-yl]-N-(6,7,8,9-tetrahydro-5H-benzocyclohepten-5-yl)-acetamide:

prepared by reaction of 1-(3,4-Dimethoxy-benzyl)-6-methoxy-7-isopropoxy-1,2,3,4-tetrahydroisoquinoline and 2-bromoacetyl bromide with 6,7,8,9-tetrahydro-5H-benzocyclohepten-5-ylamine LC-MS: rt=0.81 min, 573 (M+1, ES+).

EXAMPLE 159

2-[1-(3,4-Methylenedioxy-benzyl)-6,7-dimethoxy-3,4-dihydro-1H-isoquinolin-2-yl]-N-(indan-1-yl)-acetamide:

prepared by reaction of 1-(3,4-Methylenedioxy-benzyl)-6,7-dimethoxy-1,2,3,4-tetrahydroisoquinoline and 2-bromoacetyl bromide with 1-amino-indane LC-MS: rt=4.2 min, 501 (M+1, ES+).

EXAMPLE 160

2-[1-(3,4-Methylenedioxy-benzyl)-6,7-dimethoxy-3,4-dihydro-1H-isoquinolin-2-yl]-N-benzyl-acetamide:

prepared by reaction of 1-(3,4-Methylenedioxy-benzyl)-6,7-dimethoxy-1,2,3,4-tetrahydroisoquinoline and 2-bromoacetyl bromide with benzylamine LC-MS: rt=4.0 min, 475 (M+1, ES+).

EXAMPLE 161

2-[1-(3,4-Methylenedioxy-benzyl)-6,7-dimethoxy-3,4-dihydro-1H-isoquinolin-2-yl]-N-(2-ethoxy-benzyl)-acetamide:

prepared by reaction of 1-(3,4-Methylenedioxy-benzyl)-6,7-dimethoxy-1,2,3,4-tetrahydroisoquinoline and 2-bromoacetyl bromide with 2-ethoxy-benzylamine LC-MS: rt=4.2 min, 519 (M+1, ES+).

EXAMPLE 162

2-[1-(3,4-Methylenedioxy-benzyl)-6,7-dimethoxy-3,4-dihydro-1H-isoquinolin-2-yl]-N-[(1R,2S)-2-hydroxy-indan-1-yl]-acetamide:

prepared by reaction of 1-(3,4-Methylenedioxy-benzyl)-6,7-dimethoxy-1,2,3,4-tetrahydroisoquinoline and 2-bromoacetyl bromide with (1R,2S)-1-amino-2-indanol LC-MS: rt=3.7 min, 517 (M+1, ES+), 515 (M−1, ES−).

EXAMPLE 163

2-[1-(3,4-Methylenedioxy-benzyl)-6,7-dimethoxy-3,4-dihydro-1H-isoquinolin-2-yl]-N-(indan-2-yl)-acetamide:

prepared by reaction of 1-(3,4-Methylenedioxy-benzyl)-6,7-dimethoxy-1,2,3,4-tetrahydroisoquinoline and 2-bromoacetyl bromide with 2-amino-indane LC-MS: rt=4.1 min, 501 (M+1, ES+).

EXAMPLE 164

2-[1-(4-Dimethylamino-benzyl)-6,7-dimethoxy-3,4-dihydro-1H-isoquinolin-2-yl]-N-(indan-1-yl)-acetamide:

prepared by reaction of 1-(4-Dimethylamino-benzyl)-6,7-dimethoxy-1,2,3,4-tetrahydroisoquinoline and 2-bromoacetyl bromide with 1-amino-indane LC-MS: rt=3.7 min, 500 (M+1, ES+).

EXAMPLE 165

2-[1-(4-Dimethylamino-benzyl)-6,7-dimethoxy-3,4-dihydro-1H-isoquinolin-2-yl]-N-(1,2,3,4-tetrahydro-naphthalen-1-yl)-acetamide:

prepared by reaction of 1-(4-Dimethylamino-benzyl)-6,7-dimethoxy-1,2,3,4-tetrahydroisoquinoline and 2-bromoacetyl bromide with 1,2,3,4-tetrahydro-1-naphthylamine LC-MS: rt=3.9 min, 514 (M+1, ES+).

EXAMPLE 166

2-[1-(4-Dimethylamino-benzyl)-6,7-dimethoxy-3,4-dihydro-1H-isoquinolin-2-yl]-N-benzyl-acetamide:

prepared by reaction of 1-(4-Dimethylamino-benzyl)-6,7-dimethoxy-1,2,3,4-tetrahydroisoquinoline and 2-bromoacetyl bromide with benzylamine LC-MS: rt=3.5 min, 474 (M+1, ES+).

EXAMPLE 167

2-[1-(4-Dimethylamino-benzyl)-6,7-dimethoxy-3,4-dihydro-1H-isoquinolin-2-yl]-N-(naphthalen-1-yl-methyl)-acetamide:

prepared by reaction of 1-(4-Dimethylamino-benzyl)-6,7-dimethoxy-1,2,3,4-tetrahydroisoquinoline and 2-bromoacetyl bromide with naphthalen-1-yl-methylamine LC-MS: rt=4.0 min, 524 (M+1, ES+).

EXAMPLE 168

2-[1-(4-Dimethylamino-benzyl)-6,7-dimethoxy-3,4-dihydro-1H-isoquinolin-2-yl]-N-(2-methoxy-benzyl)-acetamide:

prepared by reaction of 1-(4-Dimethylamino-benzyl)-6,7-dimethoxy-1,2,3,4-tetrahydroisoquinoline and 2-bromoacetyl bromide with 2-methoxy-benzylamine LC-MS: rt=3.6 min, 504 (M+1, ES+).

EXAMPLE 169

2-[1-(4-Dimethylamino-benzyl)-6,7-dimethoxy-3,4-dihydro-1H-isoquinolin-2-yl]-N-(2-ethoxy-benzyl)-acetamide:

prepared by reaction of 1-(4-Dimethylamino-benzyl)-6,7-dimethoxy-1,2,3,4-tetrahydroisoquinoline and 2-bromoacetyl bromide with 2-ethoxy-benzylamine LC-MS: rt=3.8 min, 518 (M+1, ES+).

EXAMPLE 170

2-[1-(4-Dimethylamino-benzyl)-6,7-dimethoxy-3,4-dihydro-1H-isoquinolin-2-yl]-N-[(1R,2S)-2-hydroxy-indan-1-yl]-acetamide:

prepared by reaction of 1-(4-Dimethylamino-benzyl)-6,7-dimethoxy-1,2,3,4-tetrahydroisoquinoline and 2-bromoacetyl bromide with (1R,2S)-1-amino-2-indanol LC-MS: rt=3.3 min, 516 (M+1, ES+).

EXAMPLE 171

2-[1-(4-Dimethylamino-benzyl)-6,7-dimethoxy-3,4-dihydro-11H-isoquinolin-2-yl]-N-(pyridin-2-yl-methyl)-acetamide:

prepared by reaction of 1-(4-Dimethylamino-benzyl)-6,7-dimethoxy-1,2,3,4-tetrahydroisoquinoline and 2-bromoacetyl bromide with 2-picolylamine LC-MS: rt=2.9 min, 475 (M+1, ES+).

EXAMPLE 172

2-[1-(4-Fluoro-benzyl)-6,7-dimethoxy-3,4-dihydro-1H-isoquinolin-2-yl]-N-(indan-1-yl)-acetamide:

prepared by reaction of 1-(4-Fluoro-benzyl)-6,7-dimethoxy-1,2,3,4-tetrahydroisoquinoline and 2-bromoacetyl bromide with 1-amino-indane LC-MS: rt=4.3 min, 475 (M+1, ES+).

EXAMPLE 173

2-[1-(4-Fluoro-benzyl)-6,7-dimethoxy-3,4-dihydro-1H-isoquinolin-2-yl]-N-(1,2,3,4-tetrahydro-naphthalen-1-yl)-acetamide:

prepared by reaction of 1-(4-Fluoro-benzyl)-6,7-dimethoxy-1,2,3,4-tetrahydroisoquinoline and 2-bromoacetyl bromide with 1,2,3,4-tetrahydro-1-naphthylamine LC-MS: rt=4.5 min, 489 (M+1, ES+).

EXAMPLE 174

2-[1-(4-Fluoro-benzyl)-6,7-dimethoxy-3,4-dihydro-1H-isoquinolin-2-yl]-N-(2-ethoxy-benzyl)-acetamide:

prepared by reaction of 1-(4-Fluoro-benzyl)-6,7-dimethoxy-1,2,3,4-tetrahydroisoquinoline and 2-bromoacetyl bromide with 2-ethoxy-benzylamine LC-MS: rt=4.3 min, 493 (M+1, ES+).

EXAMPLE 175

2-[1-(4-Fluoro-benzyl)-6,7-dimethoxy-3,4-dihydro-1H-isoquinolin-2-yl]-N-benzyl-N-methyl-acetamide:

prepared by reaction of 1-(4-Fluoro-benzyl)-6,7-dimethoxy-1,2,3,4-tetrahydroisoquinoline and 2-bromoacetyl bromide with N-benzyl-N-methylamine LC-MS: rt=3.8 min, 463 (M+1, ES+).

EXAMPLE 176

2-[1-(3,4-Difluoro-benzyl)-6,7-dimethoxy-3,4-dihydro-1H-isoquinolin-2-yl]-N-benzyl-N-methyl-acetamide:

prepared by reaction of 1-(3,4-Difluoro-benzyl)-6,7-dimethoxy-1,2,3,4-tetrahydroisoquinoline and 2-bromoacetyl bromide with N-benzyl-N-methylamine LC-MS: rt=3.9 min, 481 (M+1, ES+).

EXAMPLE 177

2-[1-(3,4,5-Trimethoxy-benzyl)6,7-dimethoxy-3,4-dihydro-1H-isoquinolin-2-yl]-N-(indan-1-yl)-acetamide:

prepared by reaction of 1-(3,4,5-Trimethoxy-benzyl)-6,7-dimethoxy-1,2,3,4-tetrahydroisoquinoline and 2-bromoacetyl bromide with 1-amino-indane LC-MS: rt=4.0 min, 547 (M+1, ES+).

EXAMPLE 178

2-[1-(3,4-Dimethoxy-benzyl)-6,7,8-trimethoxy-3,4-dihydro-1H-isoquinolin-2-yl]-N-(indan-1-yl)-acetamide:

prepared by reaction of 1-(3,4-Dimethoxy-benzyl)-6,7,8-trimethoxy-1,2,3,4-tetrahydroisoquinoline and 2-bromoacetyl bromide with 1-amino-indane LC-MS: rt=4.5 min, 547 (M+1, ES+).

EXAMPLE 179

2-[1-(3,4-Dimethoxy-benzyl)-6,7,8-trimethoxy-3,4-dihydro-1H-isoquinolin-2-yl]-N-(1,2,3,4-tetrahydro-naphthalen-1-yl)-acetamide:

prepared by reaction of 1-(3,4-Dimethoxy-benzyl)-6,7,8-trimethoxy-1,2,3,4-tetrahydroisoquinoline and 2-bromoacetyl bromide with 1,2,3,4-tetrahydro-1-naphthylamine LC-MS: rt=4.7 min, 561 (M+1, ES+).

EXAMPLE 180

2-[1-(3,4-Dimethoxy-benzyl)-6,7,8-trimethoxy-3,4-dihydro-1H-isoquinolin-2-yl]-N-benzyl-acetamide:

prepared by reaction of 1-(3,4-Dimethoxy-benzyl)-6,7,8-trimethoxy-1,2,3,4-tetrahydroisoquinoline and 2-bromoacetyl bromide with benzylamine LC-MS: rt=4.4 min, 521 (M+1, ES+).

EXAMPLE 181

2-[1-(3,4-Dimethoxy-benzyl)6,7,8-trimethoxy-3,4-dihydro-1H-isoquinolin-2-yl]-N-(naphthalen-1-yl-methyl)-acetamide:

prepared by reaction of 1-(3,4-Dimethoxy-benzyl)-6,7,8-trimethoxy-1,2,3,4-tetrahydroisoquinoline and 2-bromoacetyl bromide with naphthalen-1-yl-methylamine LC-MS: rt=4.8 min, 571 (M+1, ES+).

EXAMPLE 182

2-[1-(3,4-Dimethoxy-benzyl)-6,7,8-trimethoxy-3,4-dihydro-1H-isoquinolin-2-yl]-N-(2-methoxy-benzyl)-acetamide:

prepared by reaction of 1-(3,4-Dimethoxy-benzyl)-6,7,8-trimethoxy-1,2,3,4-tetrahydroisoquinoline and 2-bromoacetyl bromide with 2-methoxy-benzyl-amine LC-MS: rt=4.4 min, 551 (M+1, ES+).

EXAMPLE 183

2-[1-(3,4-Dimethoxy-benzyl)-6,7,8-trimethoxy-3,4-dihydro-1H-isoquinolin-2-yl]-N-(2-ethoxy-benzyl)-acetamide:

prepared by reaction of 1-(3,4-Dimethoxy-benzyl)-6,7,8-trimethoxy-1,2,3,4-tetrahydroisoquinoline and 2-bromoacetyl bromide with 2-ethoxy-benzyl-amine LC-MS: rt=4.6 min, 565 (M+1, ES+).

EXAMPLE 184

2-[1-(3,4-Dimethoxy-benzyl)-6,7,8-trimethoxy-3,4-dihydro-1H-isoquinolin-2-yl]-N-benzyl-N-methyl-acetamide:

prepared by reaction of 1-(3,4-Dimethoxy-benzyl)-6,7,8-trimethoxy-1,2,3,4-tetrahydroisoquinoline and 2-bromoacetyl bromide with N-benzyl-N-methylamine LC-MS: rt=4.0 min, 535 (M+1, ES+).

EXAMPLE 185

2-[1-(3,4-Dimethoxy-benzyl)-6,7,8-trimethoxy-3,4-dihydro-1H-isoquinolin-2-yl]-N-[(1S,2R)-2-hydroxy-indan-1-yl]-acetamide:

prepared by reaction of 1-(3,4-Dimethoxy-benzyl)-6,7,8-trimethoxy-1,2,3,4-tetrahydroisoquinoline and 2-bromoacetyl bromide with (1S,2R)-1-amino-2-indanol LC-MS: rt=4.0 min, 563 (M+1, ES+), 561 (M−1, ES−).

EXAMPLE 186

2-[1-(3,4-Dimethoxy-benzyl)-6,7,8-trimethoxy-3,4-dihydro-1H-isoquinolin-2-yl]-N-[(1R,2S)-2-hydroxy-indan-1-yl]-acetamide:

prepared by reaction of 1-(3,4-Dimethoxy-benzyl)-6,7,8-trimethoxy-1,2,3,4-tetrahydroisoquinoline and 2-bromoacetyl bromide with (1R,2S)-1-amino-2-indanol LC-MS: rt=4.0 min, 563 (M+1, ES+).

EXAMPLE 187

2-[1-(3,4-Dimethoxy-benzyl)-6,7,8-trimethoxy-3,4-dihydro-1H-isoquinolin-2-yl]-N-(pyridin-2-yl-methyl)-acetamide:

prepared by reaction of 1-(3,4-Dimethoxy-benzyl)-6,7,8-trimethoxy-1,2,3,4-tetrahydroisoquinoline and 2-bromoacetyl bromide with 2-picolylamine LC-MS: rt=3.7 min, 522 (M+1, ES+).

EXAMPLE 188

2-[1-(3,4-Dimethoxy-benzyl)-6,7,8-trimethoxy-3,4-dihydro-1H-isoquinolin-2-yl]-N-(2-phenyl-ethyl)-acetamide:

prepared by reaction of 1-(3,4-Dimethoxy-benzyl)-6,7,8-trimethoxy-1,2,3,4-tetrahydroisoquinoline and 2-bromoacetyl bromide with 2-phenyl-ethylamine LC-MS: rt=4.5 min, 535 (M+1, ES+).

EXAMPLE 189

2-[1-(3,4-Dimethoxy-benzyl)-6,7,8-trimethoxy-3,4-dihydro-1H-isoquinolin-2-yl]-N-(cyclohexyl-methyl)-acetamide:

prepared by reaction of 1-(3,4-Dimethoxy-benzyl)-6,7,8-trimethoxy-1,2,3,4-tetrahydroisoquinoline and 2-bromoacetyl bromide with cyclohexyl-methylamine LC-MS: rt=4.6 min, 527 (M+1, ES+).

EXAMPLE 190

2-[1-(3,4-Dimethoxy-benzyl)-5,6,7-trimethoxy-3,4-dihydro-1H-isoquinolin-2-yl]-N-(indan-1-yl)-acetamide:

prepared by reaction of 1-(3,4-Dimethoxy-benzyl)-5,6,7-trimethoxy-1,2,3,4-tetrahydroisoquinoline and 2-bromoacetyl bromide with 1-amino-indane LC-MS: rt=4.3 min. 547 (M+1, ES+).

EXAMPLE 191

2-[1-(3,4-Dimethoxy-benzyl)-5,6,7-trimethoxy-3,4-dihydro-1H-isoquinolin-2-yl]-N-(1,2,3,4-tetrahydro-naphthalen-1-yl)-acetamide:

prepared by reaction of 1-(3,4-Dimethoxy-benzyl)-5,6,7-trimethoxy-1,2,3,4-tetrahydroisoquinoline and 2-bromoacetyl bromide with 1,2,3,4-tetrahydro-1-naphthylamine LC-MS: rt=4.4 min, 561 (M+1, ES+).

EXAMPLE 192

2-[1-(3,4-Dimethoxy-benzyl)-5,6,7-trimethoxy-3,4-dihydro-1H-isoquinolin-2-yl]-N-benzyl-acetamide:

prepared by reaction of 1-(3,4-Dimethoxy-benzyl)-5,6,7-trimethoxy-1,2,3,4-tetrahydroisoquinoline and 2-bromoacetyl bromide with benzylamine LC-MS: rt=4.1 min, 521 (M+1, ES+).

EXAMPLE 193

2-[1-(3,4-Dimethoxy-benzyl)-5,6,7-trimethoxy-3,4-dihydro-1H-isoquinolin-2-yl]-N-(naphthalen-1-yl-methyl)-acetamide:

prepared by reaction of 1-(3,4-Dimethoxy-benzyl)-5,6,7-trimethoxy-1,2,3,4-tetrahydroisoquinoline and 2-bromoacetyl bromide with naphthalen-1-yl-methylamine LC-MS: rt=4.5 min, 571 (M+1, ES+).

EXAMPLE 194

2-[1-(3,4-Dimethoxy-benzyl)-5,6,7-trimethoxy-3,4-dihydro-1H-isoquinolin-2-yl]-N-(2-methoxy-benzyl)-acetamide:

prepared by reaction of 1-(3,4-Dimethoxy-benzyl)-5,6,7-trimethoxy-1,2,3,4-tetrahydroisoquinoline and 2-bromoacetyl bromide with 2-methoxy-benzyl-amine LC-MS: rt=4.2 min, 551 (M+1, ES+).

EXAMPLE 195

2-[1-(3,4-Dimethoxy-benzyl)-5,6,7-trimethoxy-3,4-dihydro-1H-isoquinolin-2-yl]-N-(2-ethoxy-benzyl)-acetamide:

prepared by reaction of 1-(3,4-Dimethoxy-benzyl)-5,6,7-trimethoxy-1,2,3,4-tetrahydroisoquinoline and 2-bromoacetyl bromide with 2-ethoxy-benzyl-amine LC-MS: rt=4.3 min. 565 (M+1, ES+).

EXAMPLE 196

2-[1-(3,4-Dimethoxy-benzyl)-5,6,7-trimethoxy-3,4-dihydro-1H-isoquinolin-2-yl]-N-benzyl-N-methyl-acetamide:

prepared by reaction of 1-(3,4-Dimethoxy-benzyl)-5,6,7-trimethoxy-1,2,3,4-tetrahydroisoquinoline and 2-bromoacetyl bromide with N-benzyl-N-methyl-amine LC-MS: rt=3.9 min, 535 (M+1, ES+).

EXAMPLE 197

2-[1-(3,4-Dimethoxy-benzyl)-5,6,7-trimethoxy-3,4-dihydro-1H-isoquinolin-2-yl]-N-[(1R,2S)-2-hydroxy-indan-1-yl]-acetamide:

prepared by reaction of 1-(3,4-Dimethoxy-benzyl)-5,6,7-trimethoxy-1,2,3,4-tetrahydroisoquinoline and 2-bromoacetyl bromide with (1R,2S)-1-amino-2-indanol LC-MS: rt=3.8 min, 563 (M+1, ES+), 561 (M−1, ES−).

EXAMPLE 198

2-[1-(3,4-Dimethoxy-benzyl)-5,6,7-trimethoxy-3,4-dihydro-1H-isoquinolin-2-yl]-N-[(1S,2R)-2-hydroxy-indan-1-yl]-acetamide:

prepared by reaction of 1-(3,4-Dimethoxy-benzyl)-5,6,7-trimethoxy-1,2,3,4-tetrahydroisoquinoline and 2-bromoacetyl bromide with (1S,2R)-1-amino-2-indanol LC-MS: rt=3.8 min, 563 (M+1, ES+), 561 (M−1, ES−).

EXAMPLE 199

2-[1-(3,4-Dimethoxy-benzyl)-5,6,7-trimethoxy-3,4-dihydro-1H-isoquinolin-2-yl]-N-(pyridin-2-yl-methyl)-acetamide:

prepared by reaction of 1-(3,4-Dimethoxy-benzyl)-5,6,7-trimethoxy-1,2,3,4-tetrahydroisoquinoline and 2-bromoacetyl bromide with 2-picolylamine LC-MS: rt=3.4 min, 522 (M+1, ES+).

EXAMPLE 200

2-[1-(3,4-Dimethoxy-benzyl)-5,6,7-trimethoxy-3,4-dihydro-1H-isoquinolin-2-yl]-N-(2-phenyl-ethyl)-acetamide:

prepared by reaction of 1-(3,4-Dimethoxy-benzyl)-5,6,7-trimethoxy-1,2,3,4-tetrahydroisoquinoline and 2-bromoacetyl bromide with 2-phenyl-ethylamine LC-MS: rt=4.2 min, 535 (M+1, ES+).

EXAMPLE 201

2-[1-(3,4-Dimethoxy-benzyl)-5,6,7-trimethoxy-3,4-dihydro-1H-isoquinolin-2-yl]-N-(cyclohexyl-methyl)-acetamide:

prepared by reaction of 1-(3,4-Dimethoxy-benzyl)-5,6,7-trimethoxy-1,2,3,4-tetrahydroisoquinoline and 2-bromoacetyl bromide with cyclohexyl-methylamine LC-MS: rt=4.3 min, 527 (M+1, ES+).

EXAMPLE 202

2-[1-(3,4-Dimethoxy-benzyl)-5,6,7-trimethoxy-3,4-dihydro-1H-isoquinolin-2-yl]-N-(indan-2-yl)-acetamide:

prepared by reaction of 1-(3,4-Dimethoxy-benzyl)-5,6,7-trimethoxy-1,2,3,4-tetrahydroisoquinoline and 2-bromoacetyl bromide with 2-amino-indane LC-MS: rt=4.2 min, 547 (M+1, ES+).

EXAMPLE 203

2-[1-(3,4-Dimethoxy-benzyl)-6,8-dimethoxy-3,4-dihydro-1H-isoquinolin-2-yl]-N-[(1S)-indan-1-yl]-acetamide:

prepared by reaction of 1-(3,4-Dimethoxy-benzyl)-6,8-dimethoxy-1,2,3,4-tetrahydroisoquinoline and 2-bromoacetyl bromide with (1S)-1-amino-indane LC-MS: rt=4.4 min, 517 (M+1, ES+).

EXAMPLE 204

2-[1-(3,4-Dimethoxy-benzyl)-6,8-dimethoxy-3,4-dihydro-1H-isoquinolin-2-yl]-N-[(1R)-indan-1-yl]-acetamide:

prepared by reaction of 1-(3,4-Dimethoxy-benzyl)-6,8-dimethoxy-1,2,3,4-tetrahydroisoquinoline and 2-bromoacetyl bromide with (1R)-1-amino-indane LC-MS: rt=4.4 min, 517 (M+1, ES+).

EXAMPLE 205

2-[1-(3,4-Dimethoxy-benzyl)-6,8-dimethoxy-3,4-dihydro-1H-isoquinolin-2-yl]-N-(1,2,3,4-tetrahydro-naphthalen-1-yl)-acetamide:

prepared by reaction of 1-(3,4-Dimethoxy-benzyl)-6,8-dimethoxy-1,2,3,4-tetrahydroisoquinoline and 2-bromoacetyl bromide with 1,2,3,4-tetrahydro-1-naphthylamine LC-MS: rt=4.5 min, 531 (M+1, ES+).

EXAMPLE 206

2-[1-(3,4-Dimethoxy-benzyl)-6,8-dimethoxy-3,4-dihydro-1H-isoquinolin-2-yl]-N-benzyl-acetamide:

prepared by reaction of 1-(3,4-Dimethoxy-benzyl)-6,8-dimethoxy-1,2,3,4-tetrahydroisoquinoline and 2-bromoacetyl bromide with benzylamine LC-MS: rt=4.2 min, 491 (M+1, ES+).

EXAMPLE 207

2-[1-(3,4-Dimethoxy-benzyl)-6,8-dimethoxy-3,4-dihydro-1H-isoquinolin-2-yl]-N-(naphthalen-1-yl-methyl)-acetamide:

prepared by reaction of 1-(3,4-Dimethoxy-benzyl)-6,8-dimethoxy-1,2,3,4-tetrahydroisoquinoline and 2-bromoacetyl bromide with naphthalen-1-yl-methylamine LC-MS: rt=4.5 min, 541 (M+1, ES+).

EXAMPLE 208

2-[1-(3,4-Dimethoxy-benzyl)-6,8-dimethoxy-3,4-dihydro-1H-isoquinolin-2-yl]-N-(2-methoxy-benzyl)-acetamide:

prepared by reaction of 1-(3,4-Dimethoxy-benzyl)-6,8-dimethoxy-1,2,3,4-tetrahydroisoquinoline and 2-bromoacetyl bromide with 2-methoxy-benzyl-amine LC-MS: rt=4.2 min, 521 (M+1, ES+).

EXAMPLE 209

2-[1-(3,4-Dimethoxy-benzyl)-6,8-dimethoxy-3,4-dihydro-1H-isoquinolin-2-yl]-N-(2-ethoxy-benzyl)-acetamide:

prepared by reaction of 1-(3,4-Dimethoxy-benzyl)-6,8-dimethoxy-1,2,3,4-tetrahydroisoquinoline and 2-bromoacetyl bromide with 2-ethoxy-benzyl-amine LC-MS: rt=4.4 min, 535 (M+1, ES+).

EXAMPLE 210

2-[1-(3,4-Dimethoxy-benzyl)-6,8-dimethoxy-3,4-dihydro-1H-isoquinolin-2-yl]-N-(pyridin-2-yl-methyl)-acetamide:

prepared by reaction of 1-(3,4-Dimethoxy-benzyl)-6,8-dimethoxy-1,2,3,4-tetrahydroisoquinoline and 2-bromoacetyl bromide with 2-picolylamine LC-MS: rt=4.2 min, 492 (M+1, ES+).

EXAMPLE 211

2-[1-(3,4-Dimethoxy-benzyl)-6,8-dimethoxy-3,4-dihydro-1H-isoquinolin-2-yl]-N-[(1R,2S)-2-hydroxy-indan-1-yl]-acetamide:

prepared by reaction of 1-(3,4-Dimethoxy-benzyl)-6,8-dimethoxy-1,2,3,4-tetrahydroisoquinoline and 2-bromoacetyl bromide with (1R,2S)-1-amino-2-indanol LC-MS: rt=3.9 min, 533 (M+1, ES+).

EXAMPLE 212

2-[1-(3,4-Dimethoxy-benzyl)-6,8-dimethoxy-3,4-dihydro-1H-isoquinolin-2-yl]-N-[(1S,2R)-2-hydroxy-indan-1-yl]-acetamide:

prepared by reaction of 1-(3,4-Dimethoxy-benzyl)-6,8-dimethoxy-1,2,3,4-tetrahydroisoquinoline and 2-bromoacetyl bromide with (1S,2R)-1-amino-2-indanol LC-MS: rt=3.9 min, 533 (M+1, ES+).

EXAMPLE 213

2-[1-(2,3,4-Trimethoxy-benzyl)-6,7-dimethoxy-3,4-dihydro-1H-isoquinolin-2-yl]-N-(indan-1-yl)-acetamide:

prepared by reaction of 1-(2,3,4-Trimethoxy-benzyl)-6,7-dimethoxy-1,2,3,4-tetrahydroisoquinoline and 2-bromoacetyl bromide with 1-amino-indane LC-MS: rt=4.1 min, 547 (M+1, ES+).

EXAMPLE 214

2-[1-(2,3,4-Trimethoxy-benzyl)-6,7-dimethoxy-3,4-dihydro-1H-isoquinolin-2-yl]-N-(1,2,3,4-tetrahydro-naphthalen-1-yl)-acetamide:

prepared by reaction of 1-(2,3,4-Trimethoxy-benzyl)-6,7-dimethoxy-1,2,3,4-tetrahydroisoquinoline and 2-bromoacetyl bromide with 1,2,3,4-tetrahydro-1-naphthylamine LC-MS: rt=4.3 min, 561 (M+1, ES+).

EXAMPLE 215

2-[1-(2,3,4-Trimethoxy-benzyl)-6,7-dimethoxy-3,4-dihydro-1H-isoquinolin-2-yl]-N-benzyl-acetamide:

prepared by reaction of 1-(2,3,4-Trimethoxy-benzyl)-6,7-dimethoxy-1,2,3,4-tetrahydroisoquinoline and 2-bromoacetyl bromide with benzylamine LC-MS: rt=3.9 min, 521 (M+1, ES+).

EXAMPLE 216

2-[1-(2,3,4-Trimethoxy-benzyl)-6,7-dimethoxy-3,4-dihydro-1H-isoquinolin-2-yl]-N-(naphthalen-1-yl-methyl)-acetamide:

prepared by reaction of 1-(2,3,4-Trimethoxy-benzyl)-6,7-dimethoxy-1,2,3,4-tetrahydroisoquinoline and 2-bromoacetyl bromide with naphthalen-1-yl-methylamine LC-MS: rt=4.3 min, 571 (M+1, ES+).

EXAMPLE 217

2-[1-(2,3,4-Trimethoxy-benzyl)-6,7-dimethoxy-3,4-dihydro-1H-isoquinolin-2-yl]-N-(2-methoxy-benzyl)-acetamide:

prepared by reaction of 1-(2,3,4-Trimethoxy-benzyl)-6,7-dimethoxy-1,2,3,4-tetrahydroisoquinoline and 2-bromoacetyl bromide with 2-methoxy-benzyl-amine LC-MS: rt=4.0 min, 551 (M+1, ES+).

EXAMPLE 218

2-[1-(2,3,4-Trimethoxy-benzyl)-6,7-dimethoxy-3,4-dihydro-1H-isoquinolin-2-yl]-N-(2-ethoxy-benzyl)-acetamide:

prepared by reaction of 1-(2,3,4-Trimethoxy-benzyl)-6,7-dimethoxy-1,2,3,4-tetrahydroisoquinoline and 2-bromoacetyl bromide with 2-ethoxy-benzyl-amine LC-MS: rt=4.1 min, 565 (M+1, ES+).

EXAMPLE 219

2-[1-(2,3,4-Trimethoxy-benzyl)-6,7-dimethoxy-3,4-dihydro-1H-isoquinolin-2-yl]-N-[(1R,2S)-2-hydroxy-indan-1-yl]-acetamide:

prepared by reaction of 1-(2,3,4-Trimethoxy-benzyl)-6,7-dimethoxy-1,2,3,4-tetrahydroisoquinoline and 2-bromoacetyl bromide with (1R,2S)-1-amino-2-indanol LC-MS: rt=3.7 min, 563 (M+1, ES+), 561 (M−1, ES−).

EXAMPLE 220

2-[1-(2,3,4-Trimethoxy-benzyl)-6,7-dimethoxy-3,4-dihydro-1H-isoquinolin-2-yl]-N-(2-phenyl-ethyl)-acetamide:

prepared by reaction of 1-(2,3,4-Trimethoxy-benzyl)-6,7-dimethoxy-1,2,3,4-tetrahydroisoquinoline and 2-bromoacetyl bromide with 2-phenyl-ethylamine LC-MS: rt=4.0 min, 535 (M+1, ES+).

EXAMPLE 221

2-[1-(2,3,4-Trimethoxy-benzyl)-6,7-dimethoxy-3,4-dihydro-1H-isoquinolin-2-yl]-N-(indan-2-yl)-acetamide:

prepared by reaction of 1-(2,3,4-Trimethoxy-benzyl)-6,7-dimethoxy-1,2,3,4-tetrahydroisoquinoline and 2-bromoacetyl bromide with 2-ammo-indane LC-MS: rt=4.1 min, 547 (M+1, ES+).

EXAMPLE 222

2-[1-(Naphthalen-2-yl-methyl)-6,7-dimethoxy-3,4-dihydro-1H-isoquinolin-2-yl]-N-(indan-1-yl)-acetamide:

prepared by reaction of 1-(Naphthalen-2-yl-methyl)-6,7-dimethoxy-1,2,3,4-tetrahydroisoquinoline and 2-bromoacetyl bromide with 1-amino-indane LC-MS: rt=4.8 min, 507 (M+1, ES+).

EXAMPLE 223

2-[1-Naphthalen-2-yl-methyl)-6,7-dimethoxy-3,4-dihydro-11H-isoquinolin-2-yl]-N-(1,2,3,4-tetrahydro-naphthalen-1-yl)-acetamide:

prepared by reaction of 1-(Naphthalen-2-yl-methyl)-6,7-dimethoxy-1,2,3,4-tetrahydroisoquinoline and 2-bromoacetyl bromide with 1,2,3,4-tetrahydro-1-naphthylamine LC-MS: rt=4.9 min, 521 (M+1, ES+).

EXAMPLE 224

2-[1-(Naphthalen-2-yl-methyl)-6,7-dimethoxy-3,4-dihydro-1H-isoquinolin-2-yl]-N-benzyl-acetamide:

prepared by reaction of 1-(Naphthalen-2-yl-methyl)-6,7-dimethoxy-1,2,3,4-tetrahydroisoquinoline and 2-bromoacetyl bromide with benzylamine LC-MS: rt=4.5 min, 481 (M+1, ES+).

EXAMPLE 225

2-[1-(Naphthalen-2-yl-methyl)-6,7-dimethoxy-3,4-dihydro-1H-isoquinolin-2-yl]-N-(naphthalen-1-yl-methyl)-acetamide:

prepared by reaction of 1-(Naphthalen-2-yl-methyl)-6,7-dimethoxy-1,2,3,4-tetrahydroisoquinoline and 2-bromoacetyl bromide with naphthalen-1-yl-methylamine LC-MS: rt=4.8 min, 531 (M+1, ES+).

EXAMPLE 226

2-[1-(Naphthalen-2-yl-methyl)-6,7-dimethoxy-3,4-dihydro-1H-isoquinolin-2-yl]-N-(2-methoxy-benzyl)-acetamide:

prepared by reaction of 1-(Naphthalen-2-yl-methyl)-6,7-dimethoxy-1,2,3,4-tetrahydroisoquinoline and 2-bromoacetyl bromide with 2-methoxy-benzyl-amine LC-MS: rt=4.5 min, 511 (M+1, ES+).

EXAMPLE 227

2-[1-(Naphthalen-2-yl-methyl)-6,7-dimethoxy-3,4-dihydro-1H-isoquinolin-2-yl]-N-(2-ethoxy-benzyl)-acetamide:

prepared by reaction of 1-Naphthalen-2-yl-methyl)-6,7-dimethoxy-1,2,3,4-tetrahydroisoquinoline and 2-bromoacetyl bromide with 2-ethoxy-benzyl-amine LC-MS: rt=4.7 min, 525 (M+1, ES+).

EXAMPLE 228

2-[1-(Naphthalen-2-yl-methyl)-6,7-dimethoxy-3,4-dihydro-1H-isoquinolin-2-yl]-N-benzyl-N-methyl-acetamide:

prepared by reaction of 1-(Naphthalen-2-yl-methyl)-6,7-dimethoxy-1,2,3,4-tetrahydroisoquinoline and 2-bromoacetyl bromide with N-benzyl-N-methyl-amine LC-MS: rt=4.2 min. 495 (M+1, ES+).

EXAMPLE 229

1-(3,4-Dihydro-1H-isoquinolin-2-yl)-2-[1-Naphthalen-2-yl-methyl)-6,7-dimethoxy-3,4-dihydro-1H-isoquinolin-2-yl]-ethanone:

prepared by reaction of 1-(Naphthalen-2-yl-methyl)-6,7-dimethoxy-1,2,3,4-tetrahydroisoquinoline and 2-bromoacetyl bromide with 1,2,3,4-tetrahydroisoquinoline LC-MS: rt=4.3 min, 507 (M+1, ES+).

EXAMPLE 230

2-[1-(Naphthalen-2-yl-methyl)-6,7-dimethoxy-3,4-dihydro-1H-isoquinolin-2-yl]-N-(pyridin-2-yl-methyl)-acetamide:

prepared by reaction of 1-(Naphthalen-2-yl-methyl)-6,7-dimethoxy-1,2,3,4-tetrahydroisoquinoline and 2-bromoacetyl bromide with 2-picolylamine LC-MS: rt=4.4 min, 482 (M+1, ES+).

EXAMPLE 231

2-[1-(Naphthalen-2-yl-methyl)-6,7-dimethoxy-3,4-dihydro-1H-isoquinolin-2-yl]-N-[(1R,2S)-2-hydroxy-indan-1-yl]-acetamide:

prepared by reaction of 1-(Naphthalen-2-yl-methyl)-6,7-dimethoxy-1,2,3,4-tetrahydroisoquinoline and 2-bromoacetyl bromide with (1R,2S)-1-amino-2-indanol LC-MS: rt=4.1 min, 523 (M+1, ES+), 521 (M−1, ES−).

EXAMPLE 232

2-[1-(Naphthalen-2-yl-methyl)-6,7-dimethoxy-3,4-dihydro-1H-isoquinolin-2-yl]-N-[(1S,2R)-2-hydroxy-indan-1-yl]-acetamide:

prepared by reaction of 1-(Naphthalen-2-yl-methyl)-6,7-dimethoxy-1,2,3,4-tetrahydroisoquinoline and 2-bromoacetyl bromide with (1S,2R)-1-amino-2-indanol LC-MS: rt=4.1 min, 523 (M+1, ES+), 521 (M−1, ES−).

EXAMPLE 233

2-[1-(Naphthalen-2-yl-methyl)-6,7-dimethoxy-3,4-dihydro-1H-isoquinolin-2-yl]-N-(indan-2-yl)-acetamide:

prepared by reaction of 1-(Naphthalen-2-yl-methyl)-6,7-dimethoxy-1,2,3,4-tetrahydroisoquinoline and 2-bromoacetyl bromide with 2-amino-indane LC-MS: rt=4.7 min, 507 (M+1, ES+).

EXAMPLE 234

2-[1-(3-Bromo-4-methoxy-benzyl)-6,7-dimethoxy-3,4-dihydro-1H-isoquinolin-2-yl]-N-(1,2,3,4-tetrahydro-naphthalen-1-yl)-acetamide:

prepared by reaction of 1-(3-Bromo-4-methoxy-benzyl)-6,7-dimethoxy-1,2,3,4-tetrahydroisoquinoline and 2-bromoacetyl bromide with 1,2,3,4-tetrahydro-1-naphthylamine LC-MS: rt=4.7 min, 579 (M+1, ES+).

EXAMPLE 235

2-[1-(3-Bromo-4-methoxy-benzyl)-6,7-dimethoxy-3,4-dihydro-1H-isoquinolin-2-yl]-N-(indan-1-yl)-acetamide:

prepared by reaction of 1-(3-Bromo-4-methoxy-benzyl)-6,7-dimethoxy-1,2,3,4-tetrahydroisoquinoline and 2-bromoacetyl bromide with 1-amino-indane LC-MS: rt=4.5 min, 565 (M+1, ES+).

EXAMPLE 236

2-[1-(3-Bromo-4-methoxy-benzyl)-6,7-dimethoxy-3,4-dihydro-1H-isoquinolin-2-yl]-N-benzyl-acetamide:

prepared by reaction of 1-(3-Bromo-4-methoxy-benzyl)-6,7-dimethoxy-1,2,3,4-tetrahydroisoquinoline and 2-bromoacetyl bromide with benzylamine LC-MS: rt=4.3 min, 539 (M+1, ES+).

EXAMPLE 237

2-[1-(3-Bromo-4-methoxy-benzyl)-6,7-dimethoxy-3,4-dihydro-1H-isoquinolin-2-yl]-N-(naphthalen-1-yl-methyl)-acetamide:

prepared by reaction of 1-(3-Bromo-4-methoxy-benzyl)-6,7-dimethoxy-1,2,3,4-tetrahydroisoquinoline and 2-bromoacetyl bromide with naphthalen-1-yl-methylamine LC-MS: rt=4.7 min, 589 (M+1, ES+).

EXAMPLE 238

2-[1-(3-Bromo-4-methoxy-benzyl)-6,7-dimethoxy-3,4-dihydro-1H-isoquinolin-2-yl]-N-(2-ethoxy-benzyl)-acetamide:

prepared by reaction of 1-(3-Bromo-4-methoxy-benzyl)-6,7-dimethoxy-1,2,3,4-tetrahydroisoquinoline and 2-bromoacetyl bromide with 2-ethoxy-benzylamine LC-MS: rt=4.6 min, 583 (M+1, ES+).

EXAMPLE 239

2-[1-(3-Bromo-4-methoxy-benzyl)-6,7-dimethoxy-3,4-dihydro-1H-isoquinolin-2-yl]-N-(pyridin-2-yl-methyl)-acetamide:

prepared by reaction of 1-(3-Bromo-4-methoxy-benzyl)-6,7-dimethoxy-1,2,3,4-tetrahydroisoquinoline and 2-bromoacetyl bromide with 2-picolylamine LC-MS: rt=3.6 min, 541 (M+1, ES+).

EXAMPLE 240

2-[1-(3-Bromo-4-methoxy-benzyl)-6,7-dimethoxy-3,4-dihydro-1H-isoquinolin-2-yl]-N-[(1R,2S)-2-hydroxy-indan-1-yl]-acetamide:

prepared by reaction of 1-(3-Bromo-4-methoxy-benzyl)-6,7-methoxy-1,2,3,4-tetrahydroisoquinoline and 2-bromoacetyl bromide with (1R,2S)-1-amino-2-indanol LC-MS: rt=4.0 min 581 (M+1, ES+), 579 (M−1, ES−).

EXAMPLE 241

2-[1-(3,4-Methylenedioxy-benzyl)-5,8-dimethoxy-3,4-dihydro-1H-isoquinolin-2-yl]-N-(pyridin-2-yl-methyl)-acetamide:

prepared by reaction of 1-(3,4-Methylenedioxy-benzyl)-5,8-dimethoxy-1,2,3,4-tetrahydroisoquinoline and 2-bromoacetyl bromide with 2-picolylamine LC-MS: rt=3.8 min, 476 (M+1, ES+).

EXAMPLE 242

2-[1-(3,4-Methylenedioxy-benzyl)-5,8-dimethoxy-3,4-dihydro-1H-isoquinolin-2-yl]-N-(2-methoxy-benzyl)-acetamide:

prepared by reaction of 1-(3,4-Methylenedioxy-benzyl)-5,8-dimethoxy-1,2,3,4-tetrahydroisoquinoline and 2-bromoacetyl bromide with 2-methoxy-benzylamine LC-MS: rt=4.6 min, 505 (M+1, ES+).

EXAMPLE 243

2-[1-(3,4-Methylenedioxy-benzyl)-5,8-dimethoxy-3,4-dihydro-1H-isoquinolin-2-yl]-N-[1,3,4]thiadiazol-2-yl-acetamide:

prepared by reaction of 1-(3,4-Methylenedioxy-benzyl)-5,8-dimethoxy-1,2,3,4-tetrahydroisoquinoline and 2-bromoacetyl bromide with 2-amino-1,3,4-thiadiazole LC-MS: rt=4.4 min, 469 (M+1, ES+).

EXAMPLE 244

2-[1-(3,4-Methylenedioxy-benzyl)-5,8-dimethoxy-3,4-dihydro-1H-isoquinolin-2-yl]-N-(1H-benzoimidazol-2-yl-methyl)-acetamide:

prepared by reaction of 1-(3,4-Methylenedioxy-benzyl)5,8-dimethoxy-1,2,3,4-tetrahydroisoquinoline and 2-bromoacetyl bromide with 2-(aminomethyl)-benzimidazole LC-MS: rt=3.8 min, 515 (M+1, ES+).

EXAMPLE 245

2-[1-(3,4-Methylenedioxy-benzyl)-5,8-dimethoxy-3,4-dihydro-1H-isoquinolin-2-yl]-N-(1H-indazol-6-yl)-acetamide:

prepared by reaction of 1-(3,4-Methylenedioxy-benzyl)-5,8-dimethoxy-1,2,3,4-tetrahydroisoquinoline and 2-bromoacetyl bromide with 6-aminoindazole LC-MS: rt=4.4 min, 501 (M+1, ES+).

Analogous to the above mentioned procedure, but in larger scale, the following tetrahydroisoquinoline derivatives were synthesized:

EXAMPLE 246

2-[1-(3,4-Dimethoxy-benzyl)-6-benzyloxy-7-methoxy-3,4-dihydro-1H-isoquinolin-2-yl]-N-benzyl-acetamide:

prepared by reaction of 1-(3,4-Dimethoxy-benzyl)-6-benzyloxy-7-methoxy-1,2,3,4-tetrahydroisoquinoline and 2-bromoacetyl bromide with benzylamine LC-MS: rt=4.5 min, 567 (M+1, ES+).

EXAMPLE 247

2-[1-(3,4-Dimethoxy-benzyl)-7-benzyloxy-6-methoxy-3,4-dihydro-1H-isoquinolin-2-yl]-N-benzyl-acetamide:

prepared by reaction of 1-(3,4-Dimethoxy-benzyl)-7-benzyloxy-6-methoxy-1,2,3,4-tetrahydroisoquinoline and 2-bromoacetyl bromide with benzylamine LC-MS: rt=4.4 min, 567 (M+1, ES+).

2-[1-(3,4-Dimethoxy-benzyl)-7-benzyloxy-6-methoxy-3,4-dihydro-1H-isoquinolin-2-yl]-N-(indan-1-yl)-acetamide:

prepared by reaction of 1-(3,4-Dimethoxy-benzyl)-7-benzyloxy-6-methoxy-1,2,3,4-tetrahydroisoquinoline and 2-bromoacetyl bromide with 1-amino-indane LC-MS: rt=4.5 min, 593 (M+1, ES+).

EXAMPLE 248

2-[1-(3,4-Dimethoxy-benzyl)-5-benzyloxy-8-methoxy-3,4-dihydro-1H-isoquinolin-2-yl]-N-(pyridin-2-yl-methyl)-acetamide:

prepared by reaction of 1-(3,4-Dimethoxy-benzyl)-5-benzyloxy-8-methoxy-1,2,3,4-tetrahydroisoquinoline and 2-bromoacetyl bromide with 2-picolylamine LC-MS: rt=4.4 min, 568 (M+1, ES+).

2-[1-(3,4-Dimethoxy-benzyl)-8-benzyloxy-5-methoxy-3,4-dihydro-1H-isoquinolin-2-yl]-N-(pyridin-2-yl-methyl)-acetamide:

prepared by reaction of 1-(3,4-Dimethoxy-benzyl)-8-benzyloxy-5-methoxy-1,2,3,4-tetrahydroisoquinoline and 2-bromoacetyl bromide with 2-picolylamine LC-MS: rt=4.4 min, 568 (M+1, ES+).

EXAMPLE 249

2-[1-(4-Hydroxy-3-methoxy-benzyl)-6,7-dimethoxy-3,4-dihydro-1H-isoquinolin-2-yl]-N-benzyl-acetamide:

prepared by reaction of 1-(4-Hydroxy-3-methoxy-benzyl)-6,7-dimethoxy-1,2,3,4-tetrahydroisoquinoline and 2-bromoacetyl bromide with benzylamine LC-MS: rt=3.4 min, 477 (M+1, ES+).

2-[1-(3-Benzyloxy-4-methoxy-benzyl)-6,7-dimethoxy-3,4-dihydro-1H-isoquinolin-2-yl]-N-benzyl-acetamide:

prepared by reaction of 1-(3-Benzyloxy-4-methoxy-benzyl)-6,7-dimethoxy-1,2,3,4-tetrahydroisoquinoline and 2-bromoacetyl bromide with benzylamine LC-MS: rt=4.4 min, 567 (M+1, ES+).

2-(1-Benzyloxymethyl-6,7-dimethoxy-3,4-dihydro-1H-isoquinolin-2-yl)-N-(indan-1-yl)-acetamide:

prepared by reaction of 1-Benzyloxymethyl-6,7-dimethoxy-1,2,3,4-tetrahydroisoquinoline and 2-bromoacetyl bromide with 1-amino-indane LC-MS: rt=4.3 min, 487 (M+1, ES+).

C Coupling of Phenols with Alkylbromides, Heteroarylchlorides, Heteroaryl-methyl-sulfones and Carbamoylchlorides C.1 Starting Materials: Deprotection of Benzylic Ethers:

To a mixture of MeOH (60 mL) and formic acid (11.0 mL) was added Palladium (10% Pd/C, wet, 274 mg). The respective benzylic ether (4.0 mmol) was added portionwise and the mixture was stirred for 40 h. During this period further portions of Pd/C were added until the starting material was consumed. The mixture was filtered, the solvent was removed in vacuo and the residue was purified by flash-chromatography to give the following phenols:

EXAMPLE 250

2-[1-(3,4-dimethoxy-benzyl)-6-hydroxy-7-methoxy-3,4-dihydro-1H-isoquinolin-2-yl]-N-benzyl-acetamide:

prepared by deprotection of 2-[1-(3,4-dimethoxy-benzyl)-6-benzyloxy-7-methoxy-3,4-dihydro-1H-isoquinolin-2-yl]-N-benzyl-acetamide LC-MS: rt=3.5 min, 477 (M+1, ES+).

EXAMPLE 251

2-[1-(3,4-dimethoxy-benzyl)-7-hydroxy-6-methoxy-3,4-dihydro-1H-isoquinolin-2-yl]-N-benzyl-acetamide:

prepared by deprotection of 2-[1-(3,4-dimethoxy-benzyl)-7-benzyloxy-6-methoxy-3,4-dihydro-1H-isoquinolin-2-yl]-N-benzyl-acetamide LC-MS: rt=3.5 min, 477 (M+1, ES+).

EXAMPLE 252

2-[1-(3,4-dimethoxy-benzyl)-7-hydroxy-6-methoxy-3,4-dihydro-1H-isoquinolin-2-yl]-N-(indan-1-yl)-acetamide:

prepared by deprotection of 2-[1-(3,4-dimethoxy-benzyl)-7-benzyloxy-6-methoxy-3,4-dihydro-1H-isoquinolin-2-yl]-N-(indan-1-yl)-acetamide LC-MS: rt=3.7 min, 503 (M+1, ES+), 501 (M−1, ES−).

2-[1-(3,4-dimethoxy-benzyl)-5-hydroxy-8-methoxy-3,4-dihydro-1H-isoquinolin-2-yl]-N-(pyridin-2-yl-methyl)-acetamide:

prepared by deprotection of 2-[1-(3,4-dimethoxy-benzyl)-5-benzyloxy-8-methoxy-3,4-dihydro-1H-isoquinolin-2-yl]-N-(pyridin-2-yl-methyl)-acetamide LC-MS: rt=3.2 min, 478 (M+1, ES+), 476 (M−1, ES−).

2-[1-(3,4-dimethoxy-benzyl)-8-hydroxy-5-methoxy-3,4-dihydro-1H-isoquinolin-2-yl]-N-(pyridin-2-yl-methyl)-acetamide:

prepared by deprotection of 2-[1-(3,4-dimethoxy-benzyl)-8-benzyloxy-5-methoxy-3,4-dihydro-1H-isoquinolin-2-yl]-N-(pyridin-2-yl-methyl)-acetamide LC-MS: rt=3.3 min, 478 (M+1, ES+), 476 (M−1, ES−).

EXAMPLE 253

2-[1-(3-Hydroxy-4-methoxy-benzyl)-6,7-dimethoxy-3,4-dihydro-1H-isoquinolin-2-yl]-N-benzyl-acetamide:

prepared by deprotection of 2-[1-(3-Benzyloxy-4-methoxy-benzyl)-6,7-dimethoxy-3,4-dihydro-1H-isoquinolin-2-yl]-N-benzyl-acetamide:

LC-MS: rt=3.5 min, 477 (M+1, ES+), 475 (M−1, ES−).

2-(1-Hydroxymethyl-6,7-dimethoxy-3,4-dihydro-1H-isoquinolin-2-yl)-N-(indan-1-yl)-acetamide:

prepared by deprotection of 2-(1-Benzyloxymethyl-6,7-dimethoxy-3,4-dihydro-1H-isoquinolin-2-yl)-N-(indan-1-yl)-acetamide:

LC-MS: rt=3.1 min, 397 (M+1, ES+).

C.2 Alkylation of Phenols with Alkylbromides (General Procedure):

At RT a solution of the respective phenol in DMF (250 µL, 0.40 M) was added to $K_2CO_3$ (70 mg). The reaction mixture was treated with a solution of the respective alkyl bromide in DMF (150 µL, 1.00 M, shaken at 100° C. for 90 min and cooled to RT. After addition of another portion of alkyl bromide (150 µL, 1.00 M), shaking (100° C., 90 min) and cooling to RT a solution of triethylamine in THF (250 µL, 2.0 M) was added and the mixture was shaken for 14 h. Water (2.0 mL) and ethyl acetate (2.0 mL) were added, the phases were separated and the aqueous phase was extracted two times with ethyl acetate. The combined organic phases were concentrated in vacuo to give the following tetrahydroisoquinoline derivatives:

EXAMPLE 254

2-[1-(3,4-dimethoxy-benzyl)-6-ethoxy-7-methoxy-3,4-dihydro-1H-isoquinolin-2-yl]-N-benzyl-acetamide:

prepared by reaction of 2-[1-(3,4-dimethoxy-benzyl)-6-hydroxy-7-methoxy-3,4-dihydro-1H-isoquinolin-2-yl]-N-benzyl-acetamide with ethyl iodide LC-MS: rt=3.8 min, 505 (M+1, ES+).

EXAMPLE 255

2-[1-(3,4-dimethoxy-benzyl)-6-propoxy-7-methoxy-3,4-dihydro-1H-isoquinolin-2-yl]-N-benzyl-acetamide:

prepared by reaction of 2-[1-(3,4-dimethoxy-benzyl)-6-hydroxy-7-methoxy-3,4-dihydro-1H-isoquinolin-2-yl]-N-benzyl-acetamide with propyl bromide LC-MS: rt=4.1 min, 519 (M+1, ES+).

EXAMPLE 256

2-[1-(3,4-dimethoxy-benzyl)-6-allyloxy-7-methoxy-3,4-dihydro-1H-isoquinolin-2-yl]-N-benzyl-acetamide:

prepared by reaction of 2-[1-(3,4-dimethoxy-benzyl)-6-hydroxy-7-methoxy-3,4-dihydro-1H-isoquinolin-2-yl]-N-benzyl-acetamide with allyl bromide LC-MS: rt=4.0 min, 517 (M+1, ES+).

EXAMPLE 257

2-[1-(3,4-dimethoxy-benzyl)-6-(cyclopropyl-methoxy)-7-methoxy-3,4-dihydro-1H-isoquinolin-2-yl]-N-benzyl-acetamide:

prepared by reaction of 2-[1-(3,4-dimethoxy-benzyl)-6-hydroxy-7-methoxy-3,4-dihydro-1H-isoquinolin-2-yl]-N-benzyl-acetamide with cyclopropylmethyl bromide LC-MS: rt=4.1 min, 531 (M+1, ES+).

EXAMPLE 258

[2-(Benzylcarbamoyl-methyl)-1-(3,4-dimethoxy-benzyl)-7-methoxy-1,2,3,4-tetrahydro-isoquinolin-6-yloxy]-acetic acid ethyl ester:

prepared by reaction of 2-[1-(3,4-dimethoxy-benzyl)-6-hydroxy-7-methoxy-3,4-dihydro-1H-isoquinolin-2-yl]-N-benzyl-acetamide with ethyl bromoacetate

EXAMPLE 259

2-[1-(3,4-dimethoxy-benzyl)-6-(3-fluoro-propoxy)-7-methoxy-3,4-dihydro-1H-isoquinolin-2-yl]-N-benzyl-acetamide:

prepared by reaction of 2-[1-(3,4-dimethoxy-benzyl)-6-hydroxy-7-methoxy-3,4-dihydro-1H-isoquinolin-2-yl]-N-benzyl-acetamide with 1-bromo-3-fluoro-propane LC-MS: rt=4.0 min, 537 (M+1, ES+).

EXAMPLE 260

2-[1-(3,4-dimethoxy-benzyl)-7-ethoxy-6-methoxy-3,4-dihydro-1H-isoquinolin-2-yl]-N-benzyl-acetamide:

prepared by reaction of 2-[1-(3,4-dimethoxy-benzyl)-7-hydroxy-6-methoxy-3,4-dihydro-1H-isoquinolin-2-yl]-N-benzyl-acetamide with ethyl iodide LC-MS: rt=3.8 min, 505 (M+1, ES+).

EXAMPLE 261

2-[1-(3,4-dimethoxy-benzyl)-7-propoxy-6-methoxy-3,4-dihydro-1H-isoquinolin-2-yl]-N-benzyl-acetamide:

prepared by reaction of 2-[1-(3,4-dimethoxy-benzyl)-7-hydroxy-6-methoxy-3,4-dihydro-1H-isoquinolin-2-yl]-N-benzyl-acetamide with propyl bromide LC-MS: rt=4.0 min, 519 (M+1, ES+).

EXAMPLE 262

2-[1-(3,4-dimethoxy-benzyl)-7-butoxy-6-methoxy-3,4-dihydro-1H-isoquinolin-2-yl]-N-benzyl-acetamide:

prepared by reaction of 2-[1-(3,4-dimethoxy-benzyl)-7-hydroxy-6-methoxy-3,4-dihydro-1H-isoquinolin-2-yl]-N-benzyl-acetamide with butyl bromide LC-MS: rt=4.2 min, 533 (M+1, ES+).

EXAMPLE 263

2-[1-(3,4-dimethoxy-benzyl)-7-allyloxy-6-methoxy-3,4-dihydro-1H-isoquinolin-2-yl]-N-benzyl-acetamide:

prepared by reaction of 2-[1-(3,4-dimethoxy-benzyl)-7-hydroxy-6-methoxy-3,4-dihydro-1H-isoquinolin-2-yl]-N-benzyl-acetamide with allyl bromide LC-MS: rt=3.9 min, 517 (M+1, ES+).

EXAMPLE 264

2-[1-(3,4-dimethoxy-benzyl)-7-(cyclopropyl-methoxy)-6-methoxy-3,4-dihydro-1H-isoquinolin-2-yl]-N-benzyl-acetamide:

prepared by reaction of 2-[1-(3,4-dimethoxy-benzyl)-7-hydroxy-6-methoxy-3,4-dihydro-1H-isoquinolin-2-yl]-N-benzyl-acetamide with cyclopropylmethyl bromide LC-MS: rt=4.0 min, 531 (M+1, ES+).

EXAMPLE 265

[2-(Benzylcarbamoyl-methyl)-1-(3,4-dimethoxy-benzyl)-6-methoxy-1,2,3,4-tetrahydro-isoquinolin-7-yloxy]-acetic acid ethyl ester:

prepared by reaction of 2-[1-(3,4-dimethoxy-benzyl)-7-hydroxy-6-methoxy-3,4-dihydro-1H-isoquinolin-2-yl]-N-benzyl-acetamide with ethyl bromoacetate LC-MS: rt=4.0 min.

EXAMPLE 266

2-[1-(3,4-dimethoxy-benzyl)-7-ethoxy-6-methoxy-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with ethyl iodide LC-MS: rt=0.73 min, 531 (M+1, ES+).

EXAMPLE 267

2-[1-(3,4-dimethoxy-benzyl)-7-propoxy-6-methoxy-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with propyl bromide LC-MS: rt=0.77 min, 545 (M+1, ES+).

EXAMPLE 268

2-[1-(3,4-dimethoxy-benzyl)-7-allyloxy-6-methoxy-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with allyl bromide LC-MS: rt=0.75 min, 543 (M+1, ES+).

EXAMPLE 269

2-[1-(3,4-dimethoxy-benzyl)-7-isopropoxy-6-methoxy-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with isopropyl bromide LC-MS: rt=0.75 min, 545 (M+1, ES+).

EXAMPLE 270

2-[1-(3,4-dimethoxy-benzyl)-7-butoxy-6-methoxy-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with butyl bromide LC-MS: rt=0.81 min, 559 (M+1, ES+).

EXAMPLE 271

2-[1-(3,4-dimethoxy-benzyl)-7-isobutoxy-6-methoxy-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with 1-bromo-2-methyl-propane LC-MS: rt=0.80 min, 559 (M+1, ES+).

EXAMPLE 272

2-[1-(3,4-dimethoxy-benzyl)-7-(but-2-oxy)-6-methoxy-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with 2-bromo-butane LC-MS: rt=0.78 min, 559 (M+1, ES+).

EXAMPLE 273

2-[1-(3,4-dimethoxy-benzyl)-7-(cyclopropyl-methoxy)-6-methoxy-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with cyclopropyl-methyl bromide LC-MS: rt=0.76 min, 557 (M+1, ES+).

EXAMPLE 274

2-[1-(3,4-dimethoxy-benzyl)-7-cyclohexyloxy-6-methoxy-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with cyclohexyl bromide LC-MS: rt=0.82 min, 585 (M+1, ES+).

EXAMPLE 275

[2-(Indan-1-ylcarbamoyl-methyl)-1-(3,4-dimethoxy-benzyl)-6-methoxy-1,2,3,4-tetrahydro-isoquinolin-7-yloxy]-acetic acid methyl ester:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with methyl bromoacetate LC-MS: rt=0.70 min, 575 (M+1, ES+).

EXAMPLE 276

2-[1-(3,4-dimethoxy-benzyl)-7-(3-fluoro-propoxy)-6-methoxy-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with 1-bromo-3-fluoro-propane LC-MS: rt=0.74 min, 563 (M+1, ES+).

EXAMPLE 277

2-[1-(3,4-dimethoxy-benzyl)-7-(2-fluoro-ethoxy)-6-methoxy-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with 1-bromo-2-fluoro-ethane LC-MS: rt=0.72 min, 549 (M+1, ES+).

EXAMPLE 278

2-[1-(3,4-dimethoxy-benzyl)-7-(2,2-difluoro-ethoxy)-6-methoxy-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with 1-bromo-2,2-difluoro-ethane LC-MS: rt=0.75 min, 567 (M+1, ES+).

EXAMPLE 279

2-[1-(3,4-dimethoxy-benzyl)-5-ethoxy-8-methoxy-3,4-dihydro-1H-isoquinolin-2-yl]-N-(pyridin-2-yl-methyl)-acetamide:

prepared by reaction of 2-[1-(3,4-dimethoxy-benzyl)-5-hydroxy-8-methoxy-3,4-dihydro-1H-isoquinolin-2-yl]-N-(pyridin-2-yl-methyl)-acetamide with ethyl iodide LC-MS: rt=0.61 min, 506 (M+1, ES+).

EXAMPLE 280

2-[1-(3,4-dimethoxy-benzyl)-5-propoxy-8-methoxy-3,4-dihydro-1H-isoquinolin-2-yl]-N-(pyridin-2-yl-methyl)-acetamide:

prepared by reaction of 2-[1-(3,4-dimethoxy-benzyl)-5-hydroxy-8-methoxy-3,4-dihydro-1H-isoquinolin-2-yl]-N-(pyridin-2-yl-methyl)-acetamide with propyl bromide LC-MS: rt=0.66 min, 520 (M+1, ES+).

EXAMPLE 281

2-[1-(3,4-dimethoxy-benzyl)-5-allyloxy-8-methoxy-3,4-dihydro-1H-isoquinolin-2-yl]-N-(pyridin-2-yl-methyl)-acetamide:

prepared by reaction of 2-[1-(3,4-dimethoxy-benzyl)-5-hydroxy-8-methoxy-3,4-dihydro-1H-isoquinolin-2-yl]-N-(pyridin-2-yl-methyl)-acetamide with allyl bromide LC-MS: rt=0.63 min, 518 (M+1, ES+).

EXAMPLE 282

2-[1-(3,4-dimethoxy-benzyl)-5-isopropoxy-8-methoxy-3,4-dihydro-1H-isoquinolin-2-yl]-N-(pyridin-2-yl-methyl)-acetamide:

prepared by reaction of 2-[1-(3,4-dimethoxy-benzyl)-5-hydroxy-8-methoxy-3,4-dihydro-1H-isoquinolin-2-yl]-N-(pyridin-2-yl-methyl)-acetamide with isopropyl bromide LC-MS: rt=0.64 min, 520 (M+1, ES+).

EXAMPLE 283

2-[1-(3,4-dimethoxy-benzyl)-5-butoxy-8-methoxy-3,4-dihydro-1H-isoquinolin-2-yl]-N-(pyridin-2-yl-methyl)-acetamide:

prepared by reaction of 2-[1-(3,4-dimethoxy-benzyl)-5-hydroxy-8-methoxy-3,4-dihydro-1H-isoquinolin-2-yl]-N-(pyridin-2-yl-methyl)-acetamide with butyl bromide LC-MS: rt=0.70 min, 534 (M+1, ES+).

EXAMPLE 284

2-[1-(3,4-dimethoxy-benzyl)-5-isobutoxy-8-methoxy-3,4-dihydro-1H-isoquinolin-2-yl]-N-(pyridin-2-yl-methyl)-acetamide:

prepared by reaction of 2-[1-(3,4-dimethoxy-benzyl)-5-hydroxy-8-methoxy-3,4-dihydro-1H-isoquinolin-2-yl]-N-(pyridin-2-yl-methyl)-acetamide with 1-bromo-2-methyl-propane LC-MS: rt=0.70 min, 534 (M+1, ES+).

EXAMPLE 285

2-[1-(3,4-dimethoxy-benzyl)-5-(but-2-oxy)-8-methoxy-3,4-dihydro-1H-isoquinolin-2-yl]-N-(pyridin-2-yl-methyl)-acetamide:

prepared by reaction of 2-[1-(3,4-dimethoxy-benzyl)-5-hydroxy-8-methoxy-3,4-dihydro-1H-isoquinolin-2-yl]-N-(pyridin-2-yl-methyl)-acetamide with 2-bromo-butane LC-MS: rt=0.68 min, 534 (M+1, ES+).

EXAMPLE 286

2-[1-(3,4-dimethoxy-benzyl)-5-(cyclopropyl-methoxy)-8-methoxy-3,4-dihydro-1H-isoquinolin-2-yl]-N-(pyridin-2-yl-methyl)-acetamide:

prepared by reaction of 2-[1-(3,4-dimethoxy-benzyl)-5-hydroxy-8-methoxy-3,4-dihydro-1H-isoquinolin-2-yl]-N-(pyridin-2-yl-methyl)-acetamide with cyclopropyl-methyl bromide LC-MS: rt=0.66 min, 532 (M+1, ES+).

EXAMPLE 287

2-[1-(3,4-dimethoxy-benzyl)-5-(3-fluoro-propoxy)-8-methoxy-3,4-dihydro-1H-isoquinolin-2-yl]-N-(pyridin-2-yl-methyl)-acetamide:

prepared by reaction of 2-[1-(3,4-dimethoxy-benzyl)-5-hydroxy-8-methoxy-3,4-dihydro-1H-isoquinolin-2-yl]-N-(pyridin-2-yl-methyl)-acetamide with 1-bromo-3-fluoro-propane LC-MS: rt=0.62 min, 538 (M+1, ES+).

EXAMPLE 288

2-[1-(3,4-dimethoxy-benzyl)-5-(2-fluoro-ethoxy)-8-methoxy-3,4-dihydro-1H-isoquinolin-2-yl]-N-(pyridin-2-yl-methyl)-acetamide:

prepared by reaction of 2-[1-(3,4-dimethoxy-benzyl)-5-hydroxy-8-methoxy-3,4-dihydro-1H-isoquinolin-2-yl]-N-(pyridin-2-yl-methyl)-acetamide with 1-bromo-2-fluoro-ethane LC-MS: rt=0.59 min 524 (M+1, ES+).

EXAMPLE 289

2-[1-(3,4-dimethoxy-benzyl)-5-(2,2-difluoro-ethoxy)-8-methoxy-3,4-dihydro-1H-isoquinolin-2-yl]-N-(pyridin-2-yl-methyl)-acetamide:

prepared by reaction of 2-[1-(3,4-dimethoxy-benzyl)-5-hydroxy-8-methoxy-3,4-dihydro-1H-isoquinolin-2-yl]-N-pyridin-2-yl-methyl)-acetamide with 1-bromo-2,2-difluoro-ethane LC-MS: rt=0.61 m, 542 (M+1, ES+).

EXAMPLE 290

[2-[(Pyridin-2-yl-methyl)-carbamoyl-methyl]-1-(3,4-dimethoxy-benzyl)-8-methoxy-1,2,3,4-tetrahydro-isoquinolin-5-yloxy]-acetic acid methyl ester:

prepared by reaction of 2-[1-(3,4-dimethoxy-benzyl)-5-hydroxy-8-methoxy-3,4-dihydro-1H-isoquinolin-2-yl]-N-(pyridin-2-yl-methyl)-acetamide with methyl bromoacetate LC-MS: rt=0.58 min, 550 (M+1, ES+).

EXAMPLE 291

2-[1-(3,4-dimethoxy-benzyl)-8-ethoxy-5-methoxy-3,4-dihydro-1H-isoquinolin-2-yl]-N-(pyridin-2-yl-methyl)-acetamide:

prepared by reaction of 2-[1-(3,4-dimethoxy-benzyl)-8-hydroxy-5-methoxy-3,4-dihydro-1H-isoquinolin-2-yl]-N-(pyridin-2-yl-methyl)-acetamide with ethyl iodide LC-MS: rt=0.62 min, 506 (M+1, ES+).

EXAMPLE 292

2-[1-(3,4-dimethoxy-benzyl)-8-propoxy-5-methoxy-3,4-dihydro-1H-isoquinolin-2-yl]-N-(pyridin-2-yl-methyl)-acetamide:

prepared by reaction of 2-[1-(3,4-dimethoxy-benzyl)-8-hydroxy-5-methoxy-3,4-dihydro-1H-isoquinolin-2-yl]-N-(pyridin-2-yl-methyl)-acetamide with propyl bromide LC-MS: rt=0.66 min, 520 (M+1, ES+).

EXAMPLE 293

2-[1-(3,4-dimethoxy-benzyl)-8-allyloxy-5-methoxy-3,4-dihydro-1H-isoquinolin-2-yl]-N-(pyridin-2-yl-methyl)-acetamide:

prepared by reaction of 2-[1-(3,4-dimethoxy-benzyl)-8-hydroxy-5-methoxy-3,4-dihydro-1H-isoquinolin-2-yl]-N-(pyridin-2-yl-methyl)-acetamide with allyl bromide LC-MS: rt=0.63 min, 518 (M+1, ES+).

EXAMPLE 294

2-[1-(3,4-dimethoxy-benzyl)-8-isopropoxy-5-methoxy-3,4-dihydro-1H-isoquinolin-2-yl]-N-(pyridin-2-yl-methyl)-acetamide:

prepared by reaction of 2-[1-(3,4-dimethoxy-benzyl)-8-hydroxy-5-methoxy-3,4-dihydro-1H-isoquinolin-2-yl]-N-(pyridin-2-yl-methyl)-acetamide with isopropyl bromide LC-MS: rt=0.64 min, 520 (M+1, ES+).

EXAMPLE 295

2-[1-(3,4-dimethoxy-benzyl)-8-butoxy-5-methoxy-3,4-dihydro-1H-isoquinolin-2-yl]-N-(pyridin-2-yl-methyl)-acetamide:

prepared by reaction of 2-[1-(3,4-dimethoxy-benzyl)-8-hydroxy-5-methoxy-3,4-dihydro-1H-isoquinolin-2-yl]-N-pyridin-2-yl-methyl)-acetamide with butyl bromide LC-MS: rt=0.69 min, 534 (M+1, ES+).

EXAMPLE 296

2-[1-(3,4-dimethoxy-benzyl)-8-isobutoxy-5-methoxy-3,4-dihydro-1H-isoquinolin-2-yl]-N-(pyridin-2-yl-methyl)-acetamide:

prepared by reaction of 2-[1-(3,4-dimethoxy-benzyl)-8-hydroxy-5-methoxy-3,4-dihydro-1H-isoquinolin-2-yl]-N-pyridin-2-yl-methyl)-acetamide with 1-bromo-2-methyl-propane LC-MS: rt=0.69 min, 534 (M+1, ES+).

EXAMPLE 297

2-[1-(3,4-dimethoxy-benzyl)-8-(but-2-oxy)-5-methoxy-3,4-dihydro-1H-isoquinolin-2-yl]-N-(pyridin-2-yl-methyl)-acetamide:

prepared by reaction of 2-[1-(3,4-dimethoxy-benzyl)-8-hydroxy-5-methoxy-3,4-dihydro-1H-isoquinolin-2-yl]-N-(pyridin-2-yl-methyl)-acetamide with 2-bromo-butane LC-MS: rt=0.68 min, 534 (M+1, ES+).

EXAMPLE 298

2-[1-(3,4-dimethoxy-benzyl)-8-(cyclopropyl-methoxy)-5-methoxy-3,4-dihydro-1H-isoquinolin-2-yl]-N-(pyridin-2-yl-methyl)-acetamide:

prepared by reaction of 2-[1-(3,4-dimethoxy-benzyl)-8-hydroxy-5-methoxy-3,4-dihydro-1H-isoquinolin-2-yl]-N-(pyridin-2-yl-methyl)-acetamide with cyclopropyl-methyl bromide LC-MS: rt=0.66 min, 532 (M+1, ES+).

EXAMPLE 299

2-[1-(3,4-dimethoxy-benzyl)-8-cyclohexyloxy-5-methoxy-3,4-dihydro-1H-isoquinolin-2-yl]-N-(pyridin-2-yl-methyl)-acetamide:

prepared by reaction of 2-[1-(3,4-dimethoxy-benzyl)-8-hydroxy-5-methoxy-3,4-dihydro-1H-isoquinolin-2-yl]-N-(pyridin-2-yl-methyl)-acetamide with cyclohexyl bromide LC-MS: rt=0.73 min, 560 (M+1, ES+).

EXAMPLE 300

2-[1-(3,4-dimethoxy-benzyl)-8-(3-fluoro-propoxy)-5-methoxy-3,4-dihydro-1H-isoquinolin-2-yl]-N-(pyridin-2-yl-methyl)-acetamide:

prepared by reaction of 2-[1-(3,4-dimethoxy-benzyl)-8-hydroxy-5-methoxy-3,4-dihydro-1H-isoquinolin-2-yl]-N-(pyridin-2-yl-methyl)-acetamide with 1-bromo-3-fluoro-propane LC-MS: rt=0.62 min, 538 (M+1, ES+).

EXAMPLE 301

2-[1-(3,4-dimethoxy-benzyl)-8-(2-fluoro-ethoxy)-5-methoxy-3,4-dihydro-1H-isoquinolin-2-yl]-N-(pyridin-2-yl-methyl)-acetamide:

prepared by reaction of 2-[1-(3,4-dimethoxy-benzyl)-8-hydroxy-5-methoxy-3,4-dihydro-1H-isoquinolin-2-yl]-N-(pyridin-2-yl-methyl)-acetamide with 1-bromo-2-fluoro-ethane LC-MS: rt=0.59 min, 524 (M+1, ES+).

EXAMPLE 302

2-[1-(3,4-dimethoxy-benzyl)-8-(2,2-difluoro-ethoxy)-5-methoxy-3,4-dihydro-1H-isoquinolin-2-yl]-N-(pyridin-2-yl-methyl)-acetamide:

prepared by reaction of 2-[1-(3,4-dimethoxy-benzyl)-8-hydroxy-5-methoxy-3,4-dihydro-1H-isoquinolin-2-yl]-N-pyridin-2-yl-methyl)-acetamide with 1-bromo-2,2-difluoro-ethane LC-MS: rt=0.62 min, 542 (M+1, ES+).

EXAMPLE 303

2-[1-(4-ethoxy-3-methoxy-benzyl)-6,7-dimethoxy-3,4-dihydro-1H-isoquinolin-2-yl]-N-benzyl-acetamide:

prepared by reaction of 2-[1-(4-hydroxy-3-methoxy-benzyl)-6,7-dimethoxy-3,4-dihydro-1H-isoquinolin-2-yl]-N-benzyl-acetamide with ethyl iodide LC-MS: rt=3.9 min, 505 (M+1, ES+).

EXAMPLE 304

2-[1-(4-propoxy-3-methoxy-benzyl)-6,7-dimethoxy-3,4-dihydro-1H-isoquinolin-2-yl]-N-benzyl-acetamide:

prepared by reaction of 2-[1-(4-hydroxy-3-methoxy-benzyl)-6,7-dimethoxy-3,4-dihydro-1H-isoquinolin-2-yl]-N-benzyl-acetamide with propyl bromide LC-MS: rt=4.2 min, 519 (M+1, ES+).

EXAMPLE 305

2-[1-(4-butoxy-3-methoxy-benzyl)6,7-dimethoxy-3,4-dihydro-1H-isoquinolin-2-yl]-N-benzyl-acetamide:

prepared by reaction of 2-[1-(4-hydroxy-3-methoxy-benzyl)-6,7-dimethoxy-3,4-dihydro-1H-isoquinolin-2-yl]-N-benzyl-acetamide with butyl bromide LC-MS: rt=4.4 min, 533 (M+1, ES+).

EXAMPLE 306

2-[1-(4-allyloxy-3-methoxy-benzyl)-6,7-dimethoxy-3,4-dihydro-1H-isoquinolin-2-yl]-N-benzyl-acetamide:

prepared by reaction of 2-[1-(4-hydroxy-3-methoxy-benzyl)-6,7-dimethoxy-3,4-dihydro-1H-isoquinolin-2-yl]-N-benzyl-acetamide with allyl bromide LC-MS: rt=4.0 min, 517 (M+1, ES+).

EXAMPLE 307

2-[1-(4-isopropoxy-3-methoxy-benzyl)-6,7-dimethoxy-3,4-dihydro-1H-isoquinolin-2-yl]-N-benzyl-acetamide:

prepared by reaction of 2-[1-(4-hydroxy-3-methoxy-benzyl)6,7-dimethoxy-3,4-dihydro-1H-isoquinolin-2-yl]-N-benzyl-acetamide with isopropyl bromide LC-MS: rt=4.0 min. 519 (M+1, ES+).

EXAMPLE 308

2-[1-(4-isobutoxy-3-methoxy-benzyl)-6,7-dimethoxy-3,4-dihydro-1H-isoquinolin-2-yl]-N-benzyl-acetamide:

prepared by reaction of 2-[1-(4-hydroxy-3-methoxy-benzyl)-6,7-dimethoxy-3,4-dihydro-1H-isoquinolin-2-yl]-N-benzyl-acetamide with 1-bromo-2-methyl-propane LC-MS: rt=4.5 min, 533 (M+1, ES+).

EXAMPLE 309

2-[1-(4-(cyclopropyl-methoxy)-3-methoxy-benzyl)-6,7-dimethoxy-3,4-dihydro-1H-isoquinolin-2-yl]-N-benzyl-acetamide:

prepared by reaction of 2-[1-(4-hydroxy-3-methoxy-benzyl)-6,7-dimethoxy-3,4-dihydro-1H-isoquinolin-2-yl]-N-benzyl-acetamide with cyclopropyl-methyl bromide LC-MS: rt=4.2 min, 531 (M+1, ES+).

EXAMPLE 310

{4-[2-(Benzylcarbamoyl-methyl)-6,7-dimethoxy-1,2,3,4-tetrahydro-isoquinolin-1-ylmethyl]-2-methoxy-phenoxy}-acetic acid ethyl ester prepared by reaction of 2-[1-(4-hydroxy-3-methoxy-benzyl)-6,7-dimethoxy-3,4-dihydro-1H-isoquinolin-2-yl]-N-benzyl-acetamide with ethyl bromoacetate LC-MS: rt=3.9 min, 563 (M+1, ES+).

EXAMPLE 311

2-[1-(3-ethoxy-4-methoxy-benzyl)-6,7-dimethoxy-3,4-dihydro-1H-isoquinolin-2-yl]-N-benzyl-acetamide:

prepared by reaction of 2-[1-(3-hydroxy-4-methoxy-benzyl)-6,7-dimethoxy-3,4-dihydro-1H-isoquinolin-2-yl]-N-benzyl-acetamide with ethyl iodide LC-MS: rt=3.8 min, 505 (M+1, ES+).

EXAMPLE 312

2-[1-(3-propoxy-4-methoxy-benzyl)-6,7-dimethoxy-3,4-dihydro-1H-isoquinolin-2-yl]-N-benzyl-acetamide:

prepared by reaction of 2-[1-(3-hydroxy-4-methoxy-benzyl)-6,7-dimethoxy-3,4-dihydro-1H-isoquinolin-2-yl]-N-benzyl-acetamide with propyl bromide LC-MS: rt=4.1 min, 519 (M+1, ES+).

EXAMPLE 313

2-[1-(3-allyloxy-4-methoxy-benzyl)-6,7-dimethoxy-3,4-dihydro-1H-isoquinolin-2-yl]-N-benzyl-acetamide:

prepared by reaction of 2-[1-(3-hydroxy-4-methoxy-benzyl)-6,7-dimethoxy-3,4-dihydro-1H-isoquinolin-2-yl]-N-benzyl-acetamide with allyl bromide LC-MS: rt=4.0 min, 517 (M+1, ES+).

EXAMPLE 314

2-[1-(3-isopropoxy-4-methoxy-benzyl)6,7-dimethoxy-3,4-dihydro-1H-isoquinolin-2-yl]-N-benzyl-acetamide:

prepared by reaction of 2-[1-(3-hydroxy-4-methoxy-benzyl)-6,7-dimethoxy-3,4-dihydro-1H-isoquinolin-2-yl]-N-benzyl-acetamide with isopropyl bromide LC-MS: rt=4.0 min, 519 (M+1, ES+).

EXAMPLE 315

2-[1-(3-butoxy-4-methoxy-benzyl)-6,7-dimethoxy-3,4-dihydro-1H-isoquinolin-2-yl]-N-benzyl-acetamide:

prepared by reaction of 2-[1-(3-hydroxy-4-methoxy-benzyl)-6,7-dimethoxy-3,4-dihydro-1H-isoquinolin-2-yl]-N-benzyl-acetamide with butyl bromide LC-MS: rt=4.3 min, 533 (M+1, ES+).

EXAMPLE 316

2-{1-[3-(but-2-oxy)4-methoxy-benyl]-6,7-dimethoxy-3,4-dihydro-1H-isoquinolin-2-yl}-N-benzyl-acetamide:

prepared by reaction of 2-[1-(3-hydroxy-4-methoxy-benzyl)-6,7-dimethoxy-3,4-dihydro-1H-isoquinolin-2-yl]-N-benzyl-acetamide with 2-bromo-butane LC-MS: rt=4.2 min, 533 (M+1, ES+).

EXAMPLE 317

2-{1-[3-(cyclopropyl-methoxy)-4-methoxy-benzyl]-6,7-dimethoxy-3,4-dihydro-1H-isoquinolin-2-yl}-N-benzyl-acetamide:

prepared by reaction of 2-[1-(3-hydroxy-4-methoxy-benzyl)-6,7-dimethoxy-3,4-dihydro-1H-isoquinolin-2-yl]-N-benzyl-acetamide with cyclopropyl-methyl bromide LC-MS: rt=4.0 min, 531 (M+1, ES+).

EXAMPLE 318

2-{1-[3-(3-fluoro-propoxy)-4-methoxy-benzyl]-6,7-dimethoxy-3,4-dihydro-1H-isoquinolin-2-yl}-N-benzyl-acetamide:

prepared by reaction of 2-[1-(3-hydroxy-4-methoxy-benzyl)-6,7-dimethoxy-3,4-dihydro-1H-isoquinolin-2-yl]-N-benzyl-acetamide with 1-bromo-3-fluoro-propane LC-MS: rt=3.9 min, 537 (M+1, ES+).

EXAMPLE 319

2-[1-(3,4-dimethoxy-benzyl)-7-(1-methyl-prop-2-oxy)-6-methoxy-3,4-dihydro-1H-isoquinolin-2-yl]-N-benzyl-acetamide:

At room temperature tert.-butyl 2,2,2-trichloroacetimidate (437 mg, 0.36 mL, 2.0 mmol) was added to a solution of 2-[1-(3,4-dimethoxy-benzyl)-7-hydroxy-6-methoxy-3,4-dihydro-1H-isoquinolin-2-yl]-N-benzyl-acetamide (95.3 mg, 0.2 mmol) in dichloromethane (5.0 mL) and cyclohexane (5.0 mL). The reaction mixture was treated with a solution of boron trifluoride diethyl etherate (50 µL, 0.4 mmol) in 10 mL dichloromethane and stirred for 22 h. Another portion of tert.-butyl 2,2,2-trichloroacetimidate (244 mg, 0.20 mL, 1.1 mmol) was added. After stirring for three days a saturated solution of $NaHCO_3$ (10 mL), water (10 mL) and ethyl acetate (40 mL) were added, the phases were separated and the aqueous phase was extracted three times with ethyl acetate (30 mL). The combined organic phases were concentrated in vacuo and purified by flash-chromatography to give the titled product (80.4 mg, 75%) as pale yellow oil.

LC-MS: rt=4.2 min, 533 (M+1, ES+).

C.3 Reaktion of Phenols with Heteroaryl Chlorides or Heteroaryl-methyl Sulfones (General Procedure):

A solution of the respective heteroaryl chloride or methyl-sulfone in DMF (1.0 mL, 0.20 M) was added to a mixture of the respective phenol (0.15 mmol) and $K_2CO_3$ (75 mg). The reaction mixture was stirred at 100° C. for 16 h. Water (2.0 mL) and ethyl acetate (2.0 mL) were added, the phases were separated and the aqueous phase was extracted two times with ethyl acetate. The combined organic phases were concentrated in vacuo to give the following tetrahydroiso-quinoline derivatives:

EXAMPLE 320

2-{1-[3-(pyrimidin-2-yloxy)-4-methoxy-benzyl]-6,7-dimethoxy-3,4-dihydro-1H-isoquinolin-2-yl}-N-benzyl-acetamide:

prepared by reaction of 2-[1-(3-hydroxy-4-methoxy-benzyl)-6,7-dimethoxy-3,4-dihydro-1H-isoquinolin-2-yl]-N-benzyl-acetamide with 2-chloro-pyrimidine LC-MS: rt=0.60 min, 555 (M+1, ES+).

EXAMPLE 321

2-{1-[4-(pyrimidin-2-yloxy)-3-methoxy-benzyl]-6,7-dimethoxy-3,4-dihydro-1H-isoquinolin-2-yl}-N-benzyl-acetamide:

prepared by reaction of 2-[1-(4-hydroxy-3-methoxy-benzyl)-6,7-dimethoxy-3,4-dihydro-1H-isoquinolin-2-yl]-N-benzyl-acetamide with 2-chloro-pyrimidine LC-MS: rt=0.60 min, 555 (M+1, ES+).

EXAMPLE 322

2-[1-(3,4-dimethoxy-benzyl)-6-methoxy-7-(pyrimidin-2-yloxy)-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with 2-chloro-pyrimidine LC-MS: rt=3.81 min, 581 (M+1, ES+).

EXAMPLE 323

2-[1-(3,4-dimethoxy-benzyl)-6-methoxy-7-(5-methoxy-pyrimidin-2-yloxy)-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with 2-methane-sulfonyl-5-methoxy-pyrimidine LC-MS: rt=0.69 min, 611 (M+1, ES+).

EXAMPLE 324

2-[1-(3,4-dimethoxy-benzyl)-6-methoxy-7-(4,6-dimethyl-pyrimidin-2-yloxy)-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with 2-methane-sulfonyl-4,6-dimethyl-pyrimidine LC-MS: rt=0.70 min, 609 (M+1, ES+).

EXAMPLE 325

2-[1-(3,4-dimethoxy-benzyl-6-methoxy-7-(5-bromo-pyrimidin-2-yloxy)-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with 5-bromo-2-chloro-pyrimidine LC-MS: rt=0.74 min, 659 (M+1, ES+).

EXAMPLE 326

2-[1-(3,4-dimethoxy-benzyl)-6-methoxy-7-(5-methyl-pyrimidin-2-yloxy)-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with 2-chloro-5-methyl-pyrimidine LC-MS: rt=0.68 min, 595 (M+1, ES+).

EXAMPLE 327

2-[1-(3,4-dimethoxy-benzyl)-6-methoxy-7-(4,6-dimethoxy-pyrimidin-2-yloxy)-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-

(indan-1-yl)-acetamide with 2-methane-sulfonyl-4,6-dimethoxy-pyrimidine

LC-MS: rt=0.75 min, 641 (M+1, ES+).

EXAMPLE 328

2-[1-(3,4-dimethoxy-benzyl)-6-methoxy-7-(5-trifluoromethyl-pyrimidin-2-yloxy)-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with 2-methane-sulfonyl-5-trifluoromethyl-pyrimidine LC-MS: rt=0.77 min, 649 (M+1, ES+).

EXAMPLE 329

2-[1-(3,4-dimethoxy-benzyl)-6-methoxy-7-(5-chloro-pyridin-2-yloxy)-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with 2,5-dichloro-pyridine LC-MS: rt=0.77 min, 614 (M+1, ES+).

EXAMPLE 330

2-[1-(3,4-dimethoxy-benzyl)-6-methoxy-7-(5-trifluoromethyl-pyridin-2-yloxy)-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with 2-chloro-5-trifluoromethyl-pyridine LC-MS: rt=0.80 min, 648 (M+1, ES+).

EXAMPLE 331

2-[1-(3,4-dimethoxy-benzyl)-6-methoxy-7-(4-trifluoromethyl-pyrimidin-2-yloxy)-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with 2-chloro-4-trifluoromethyl-pyrimidine LC-MS: rt=0.77 min, 649 (M+1, ES+).

EXAMPLE 332

2-[1-(3,4-dimethoxy-benzyl)-6-methoxy-7-(2,6-dimethoxy-pyrimidin-4-yloxy)-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with 4-chloro-2,6-dimethoxy-pyrimidine LC-MS: rt=0.76 min, 641 (M+1, ES+).

EXAMPLE 333

2-[1-(3,4-dimethoxy-benzyl)-6-methoxy-7-(pyrazin-2-yloxy)-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with 2-chloro-pyrazine LC-MS: rt=0.68 min, 581 (M+1, ES+).

EXAMPLE 334

2-[1-(3,4-dimethoxy-benzyl)6-methoxy-7-(thiazol-2-yloxy)-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with 2-bromo-thiazole LC-MS: rt=0.72 min, 586 (M+1, ES+).

C.4 Reaktion of Phenols with Carbamoylchlorides (General Procedure):

A solution of the respective phenol (0.20 mmol) and triethylamine (0.30 mL, 2.15 mmol) in THF (1.0 mL) was treated with the respective carbamoylchloride (2.2 mmol) and stirred at reflux for 16 h. Water (2.0 mL) and ethyl acetate (2.0 mL) were added, the phases were separated and the aqueous phase was extracted two times with ethyl acetate. The combined organic phases were concentrated in vacuo to give the following tetrahydroisoquinoline derivatives:

EXAMPLE 335

2-[1-(3,4-dimethoxy-benzyl)-6-methoxy-7-(N,N-dimethylcarbamoyloxy)-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with N,N-dimethylcarbamoyl chloride LC-MS: rt=0.74 min, 574 (M+1, ES+).

EXAMPLE 336

2-[1-(3,4-dimethoxy-benzyl)-6-methoxy-7-(4-morpholine-carbonyloxy)-3,4-dihydro-1H-isoquinolin-2-yl]-N-(indan-1-yl)-acetamide:

prepared by reaction of 2-[1-(3,4-dimethoxy-benzyl)-7-hydroxy-6-methoxy-3,4-dihydro-1H-isoquinolin-2-yl]-N-(indan-1-yl)-acetamide with 4-morpholinecarbonyl chloride LC-MS: rt=0.72 min, 616 (M+1, ES+).

EXAMPLE 337

2-{1-[4-Methoxy-3-(N,N-dimethylcarbamoyloxy)-benzyl]-6,7-dimethoxy-3,4-dihydro-1H-isoquinolin-2-yl}-N-benzyl-acetamide:

prepared by reaction of 2-[1-(3-hydroxy-4-methoxy-benzyl)-6,7-dimethoxy-3,4-dihydro-1H-isoquinolin-2-yl]-N-benzyl-acetamide with N,N-dimethyl-carbamoyl chloride LC-MS: rt=0.62 min, 548 (M+1, ES+).

EXAMPLE 338

2-{1-[3-Methoxy-4-(N,N-dimethylcarbamoyloxy)-benzyl]-6,7-dimethoxy-3,4-dihydro-1H-isoquinolin-2-yl}-N-benzyl-acetamide:

prepared by reaction of 2-[1-(4-hydroxy-3-methoxy-benzyl)-6,7-dimethoxy-3,4-dihydro-1H-isoquinolin-2-yl]-N-benzyl-acetamide with N,N-dimethyl-carbamoyl chloride LC-MS: rt=0.63 min, 548 (M+1, ES+).

EXAMPLE 339

2-{1-[3-Methoxy-4-(4-morpholine-carbonyloxy)-benzyl]-6,7-dimethoxy-3,4-dihydro-1H-isoquinolin-2-yl}-N-benzyl-acetamide:

prepared by reaction of 2-[1-(4-hydroxy-3-methoxy-benzyl)-6,7-dimethoxy-3,4-dihydro-1H-isoquinolin-2-yl]-N-benzyl-acetamide with 4-morpholine-carbonyl chloride LC-MS: rt=0.61 min, 590 (M+1, ES+).

D Coupling of 1-Hydroxymethyl-Substituted Tetrahydroisoquinolines with Nitrogen-Nucleophiles (General Procedure):

To a solution of 2-(1-Hydroxymethyl-6,7-dimethoxy-3,4-dihydro-1H-isoquinolin-2-yl)-N-(indan-1-yl)-acetamide (0.10 mmol) and diisopropylethyl-amine (0.25 mmol) in THF (0.50 mL) was added a solution of methanesulfonyl chloride in THF (0.25 mL, 0.44 M). After 60 min the reaction mixture was treated with a solution of the respective nitrogen-nucleophile in THF (0.25 mL, 0.48 M) and stirred for 18 h. Water (2.0 mL) and ethyl acetate (2.0 mL) were added, the phases were separated and the aqueous phase was extracted two times with ethyl acetate. The combined organic phases were concentrated in vacuo to give the following tetrahydroisoquinoline derivatives:

EXAMPLE 340

2-[1-(5,6-Dimethyl-benzoimidazol-1-ylmethyl)-6,7-dimethoxy-3,4-dihydro-1H-isoquinolin-2-yl]-N-(indan-1-yl)-acetamide:

prepared by reaction of 2-(1-Hydroxymethyl-6,7-dimethoxy-3,4-dihydro-1H-isoquinolin-2-yl)-N-(indan-1-yl)-acetamide with 5,6-dimethylbenzimidazole LC-MS: rt=0.64 min 525 (M+1, ES+).

EXAMPLE 341

2-[1-(1,2,3,4-Tetrahydroisoquinolin-2-ylmethyl)-6,7-dimethoxy-3,4-dihydro-1H-isoquinolin-2-yl]-N-(indan-1-yl)-acetamide:

prepared by reaction of 2-(1-Hydroxymethyl-6,7-dimethoxy-3,4-dihydro-1H-isoquinolin-2-yl)-N-(indan-1-yl)-acetamide with 1,2,3,4-tetrahydro-isoquinoline LC-MS: rt=0.71 min, 512 (M+1, ES+).

E. General Procedure for the Preparation of the Isonitrile Derivatives

Isonitriles (or isocyanides) have been prepared by reaction of the N-alkyl-formamides (formed by reaction of the corresponding amine with formic ethyl ester) with $POCl_3$.

ABBREVIATIONS

BSA Bovine serum albumine
CHO Chinese hamster ovary
DMF Dimethylformamide
DMSO Dimethylsulfoxide
ES Electron spray
FCS Foetal calf serum
FLIPR Fluorescent imaging plate reader
HBSS Hank's balanced salt solution
HEPES 4-(2-Hydroxyethyl)-piperazine-1-ethanesulfonic acid
MeOH Methanol
MS Mass spectroscopy
LC Liquid chromatography
PyBOP Benzotriazole-1-yl-oxy-tris-pyrrolidino-Phosphoniumhexafluorophosphate
$R_f$ Retention front
$R_t$ retention time
RT Room temperature
THF Tetrahydrofuran

What is claimed is:
1. A compound of formula (I):

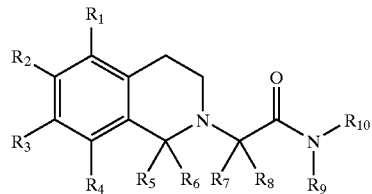

wherein:
$R^1$, $R^2$, $R^3$, $R^4$ independently represent cyano, nitro, halogen, hydrogen, hydroxy, lower alkyl, lower alkenyl, lower alkoxy, lower alkenyloxy, trifluoromethyl, trifluoromethoxy, cycloalkyloxy, aryloxy, aralkyloxy, heterocyclyloxy, heterocyclylalkyloxy, $R^{11}CO-$, $NR^{12}R^{13}CO-$, $R^{12}R^{13}N-$, $R^{11}OOC-$, $R^{11}SO_2NH-$ or $R^{14}-CO-NH-$, or $R^2$ and $R^3$ together as well as $R^1$ and $R^2$ together and $R^3$ and $R^4$ together may form with the phenyl ring a five, six or seven-membered ring containing one or two oxygen atoms;

$R^5$ represents aryl, aralkyl, lower alkenyl, trifluoromethyl, cycloalkyl, heterocyclyl or heterocyclyl-lower alkyl;

$R^6$ represents hydrogen, aryl, aralkyl, lower alkyl, lower alkenyl, trifluoromethyl, cycloalkyl, heterocyclyl or heterocyclyl-lower alkyl;

$R^7$ and $R^8$ independently represent hydrogen, aryl, aralkyl, lower alkyl, lower alkenyl, cycloalkyl, heterocyclyl or heterocyclyl-lower alkyl;

$R^9$ represents aryl, aralkyl, lower alkyl, lower alkenyl, trifluoromethyl, cycloalkyl, heterocyclyl or heterocyclyl-lower alkyl;

$R^{10}$ represents hydrogen, aryl, aralkyl, lower alkyl, lower alkenyl, trifluoromethyl, cycloalkyl, heterocyclyl or heterocyclyl-lower alkyl;

$R^{11}$ represents lower alkyl, aryl, aralkyl, heterocyclyl or heterocyclyl-lower alkyl;

$R^{12}$ and $R^{13}$ independently represent hydrogen, alkyl, cycloalkyl, aryl, aralkyl, heterocyclyl or heterocyclyl-lower alkyl; and $R^{14}$ represents alkyl, aryl, cycloalkyl, heterocyclyl, $R^{12}R^{13}N-$ or $R^{11}O-$, including optically pure enantiomers, mixtures of enantiomers, racemates, optically pure diastereoisomers, mixtures of diastereoisomers, diastereoisomeric racemates, mixtures of diastereolsomeric racemates, meso forms, and pharmaceutically acceptable salts thereof.

2. A compound of formula (II)

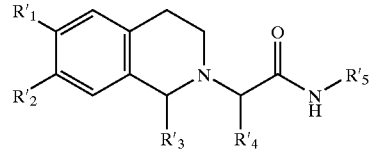

wherein:
$R'^1$ and $R'^2$ independently represent hydrogen, hydroxy, lower alkoxy or halogen or may form with the phenyl ring a five, six or seven membered-ring containing one or two oxygen atoms;

$R'^3$ represents aryl, aralkyl, lower alkenyl, cycloalkyl, heterocyclyl or heterocyclyl-lower alkyl;

$R'^4$ represents hydrogen, aryl, aralkyl, lower alkyl, lower alkenyl, cycloalkyl, heterocyclyl or heterocyclyl-lower alkyl; and $R'^5$ represents aryl, aralkyl, lower alkyl, lower alkenyl, cycloalkyl, heterocyclyl or heterocyclyl-lower alkyl;

including optically pure enantiomers, mixtures of enantiomers, racemates, optically pure diastereoisomers, mixtures of diastercoisomers, diastercoisomeric racemates, mixtures of diastereoisomeric racemates, meso forms, and pharmaceutically acceptable salts thereof.

3. A compound selected from:

2-[1-(3,4-Dimethoxy-benzyl)-5,8-dimethoxy-3,4-dihydro-1H-isoquinolin-2-yl]-N-(pyridin-2-yl-methyl)-acetamide;

2-[1-(3,4-dimethoxy-benzyl)-8-(cyclopropyl-methoxy)-5-methoxy-3,4-dihydro-1H-isoquinolin-2-yl]-N-(pyridin-2-yl-methyl)-acetamide;

2-[1-(3,4-dimethoxy-benzyl)-8-(2-fluoro-ethoxy)-5-methoxy-3,4-dihydro-1H-isoquinolin-2-yl]-N-(pyridin-2-yl-methyl)-acetamide;

2-[1-(3,4-dimethoxy-benzyl)-8-(2,2-difluoro-ethoxy)-5-methoxy-3,4-dihydro-1H-isoquinolin-2-yl]-N-(pyridin-2-yl-methyl)-acetamide;

2-[1-(3,4-dimethoxy-benzyl)-8-ethoxy-5-methoxy-3,4-dihydro-1H-isoquinolin-2-yl]-N-(pyridin-2-yl-methyl)-acetamide;

2-[1-(3,4-dimethoxy-benzyl)-8-propoxy-5-methoxy-3,4-dihydro-1H-isoquinolin-2-yl]-N-(pyridin-2-yl-methyl)-acetamide;

2-[1-(3,4-dimethoxy-benzyl)-8-allyloxy-5-methoxy-3,4-dihydro-1H-isoquinolin-2-yl]-N-(pyridin-2-yl-methyl)-acetamide;

2-[1-(3,4-dimethoxy-benzyl)-8-isopropoxy-5-methoxy-3,4-dihydro-1H-isoquinolin-2-yl]-N-(pyridin-2-yl-methyl)-acetamide;

2-[1-(3,4-dimethoxy-benzyl)-5-propoxy-8-methoxy-3,4-dihydro-1H-isoquinolin-2-yl]-N-(pyridin-2-yl-methyl)-acetamide;

2-[1-(3,4-Dimethoxy-benzyl)-6,7-dimethoxy-3,4-dihydro-1H-isoquinolin-2-yl]-N-benzyl-acetamide;

2-[1-(3,4-Dimethoxy-benzyl)-6,7-dimethoxy-3,4-dihydro-1H-isoquinolin-2-yl]-N-naphthalen-1-yl-methyl-acetamide;

2-[1-(3,4-Dimethoxy-benzyl)-6,7-dimethoxy-3,4-dihydro-1H-isoquinolin-2-yl]-N-(indan-1-yl)-acetamide;

2-[1-(3,4-Dimethoxy-benzyl)6,7-dimethoxy-3,4-dihydro-1H-isoquinolin-2-yl]-N-(1,2,3,4-tetrahydro-naphthalen-1-yl)-acetamide;

2-[1-(3,4-dimethoxy-benzyl)-6-methoxy-7-(pyrazin-2-yloxy)-3,4-dihydro-1H-isoquinolin-2-yl]-N-(indan-1-yl)-acetamide;

2-[1-(3,4-dimethoxy-benzyl)-6-methoxy-7(thiazol-2-yloxy)-3,4-dihydro-1H-isoquinolin-2-yl]-N-(indan-1-yl)-acetamide;

2-[1-(3,4-Dimethoxy-benzyl)-6-methoxy-7-isopropoxy-3,4-dihydro-1H-isoquinolin-2-yl]-N-(5-methoxy-indan-1-yl)-acetamide;

2-[1-(3,4-Dimethoxy-benzyl]-6-methoxy-7-isopropoxy-3,4-dihydro-1H-isoquinolin-2-yl]-N-(6-methoxy-indan-1-yl)-acetamide;

2-[1-(3,4-Dimethoxy-benzyl)-6-methoxy-7-isopropoxy-3,4-dihydro-1H-isoquinolin-2-yl]-N-(6-methyl-indan-1-yl)-acetamide;

2-[1-(3,4-Dimethoxy-benzyl)-6-methoxy-7-isopropoxy-3,4-dihydro-1H-isoquinolin-2-yl]-N-(2-methyl-1,2,3,4-tetrahydronaphthalen-1-yl)-acetamide;

2-[1-(3,4-Dimethoxy-benzyl)-6-methoxy-7 isopropoxy-3,4-dihydro-1H-isoquinolin-2-yl]-N-(4-methyl-indan-1-yl)-acetamide;

2-[1-(3,4-Dimethoxy-benzyl)-6,7-dimethoxy-3,4-dihydro-1H-isoquinolin-2-yl]-N-6-methoxy-indan-1-yl)-acetamide;

2-[1-(3,4-Dimethoxy-benzyl)-6,7-dimethoxy-3,4-dihydro-1H-isoquinolin-2-yl]N-(6-methyl-indan-1-yl)-acetamide;

2-{1-[4-(pyrimidin-2-yloxy)-3-methoxy-benzyl]-6,7-dimethoxy-3,4-dihydro-1H-isoquinolin-2-yl}-N-benzyl-acetamide;

2-[1-(3,4-dimethoxy-benzyl)-6-methoxy-7-(N,N-dimethylcarbamoyloxy)-3,4-dihydro-1H-isoquinolin-2-yl]-N-(indan-1-yl)-acetamide;

2-[1-(3,4-dimethoxy-benzyl)-7-(3-fluoro-propoxy)-6-methoxy-3,4-dihydro-1H-isoquinolin-2-yl]-N-(indan-1-yl)-acetamide;

2-[1-(3,4-dimethoxy-benzyl)-7-(2-fluoro-ethoxy)-6-methoxy-3,4-dihydro-1H-isoquinolin-2-yl]-N-(indan-1-yl)-acetamide;

2-[1-(3,4-dimethoxy-benzyl)-7(2,2-difluoro-ethoxy)-6-methoxy-3,4-dihydro-1H-isoquinolin-2-yl]-N-(indan 1-yl)-acetamide;

2-[1-(3,4-dimethoxy-benzyl)-7-(but-2-oxy)-6-methoxy-3,4-dihydro-1H-isoquinolin-2-yl]-N-(indan-1-yl)-acetamide;

2-[1-(3,4-dimethoxy-benzyl]-7(cyclopropyl-methoxy)-6-methoxy-3,4-dihydro-1H-isoquinolin-2-yl]-N-(indan 1-yl)-acetamide;

2-[1-(3,4-dimethoxy-benzyl)-7-ethoxy-6-methoxy-3,4-dihydro-1H-isoquinolin-2-yl]-N-(indan-1-yl)-acetamide;

2-[1-(3,4-dimethoxy-benzyl)-7-propoxy-6-methoxy-3,4-dihydro-1H-isoquinolin-2-yl]-N-(indan-1-yl)-acetamide;

2-[1-(3,4-dimethoxy-benzyl)-7-allyloxy-6-methoxy-3,4-dihydro-1H-isoquinolin-2-yl]-N-(indan-1-yl)-acetamide;

2-[1-(3,4-dimethoxy-benzyl)-7-isopropoxy-6-methoxy-3,4-dihydro-1H-isoquinolin-2-yl]-N-(indan-1-yl)-acetamide;

2-[1-(3,4-dimethoxy-benzyl)-7-(1-methyl-prop-2-oxy)-6-methoxy-3,4-dihydro-1H-isoquinolin-2-yl]-N-benzyl-acetamide;

2-[1-(3,4-Dimethoxy-benzyl)-6-methoxy-7-isopropoxy-3,4-dihydro-1H-isoquinolin-2-yl]-N-[(1S)-indan-1-yl]-acetamide;

2-[1-(3,4-Dimethoxy-benzyl)-6-methoxy-7 isopropoxy-3,4-dihydro-1H-isoquinolin-2-yl]-N-benzyl-acetamide;

2-[(1S)-1-(3,4-Dimethoxy-benzyl)-6,7-dimethoxy-3,4-dihydro-1H-isoquinolin-2-yl]-N-[(1S)-indan-1-yl]-acetamide;

2-[1-(3,4-dimethoxy-benzyl)-7-ethoxy-6-methoxy-3,4-dihydro-1H-isoquinolin-2-yl]-N-benzyl-acetamide;

2-[1-(3,4-dimethoxy-benzyl)-7-propoxy-6-methoxy-3,4-dihydro-1H-isoquinolin-2-yl]-N-benzyl-acetamide;

2-[1-(3,4-dimethoxy-benzyl)-7-allyloxy-6-methoxy-3,4-dihydro-1H-isoquinolin-2-yl]-N-benzyl-acetamide;

N-benzyl-2-[1-(3,4-Dimethyl-benzyl)-6,7-dimethoxy-3,4-dihydro-1H-isoquinolin-2-yl]-acetamide;
2-[1-(3,4-Dimethyl-benzyl)-6,7-dimethoxy-3,4-dihydro-1H-isoquinolin-2-yl]-N-[(1S)-indan-1-yl]-acetamide;
N-benzyl-2-[1-(3,4-Diethyl-benzyl)-6,7-dimethoxy-3,4-dihydro-1H-isoquinolin-2-yl]-acetamide;
2-[1-(3,4-Diethyl-benzyl)-6,7-dimethoxy-3,4-dihydro-1H-isoquinolin-2-yl]-N-(pyridin-2-yl-methyl)-acetamide;
2-[1-(3,4-Diethyl-benzyl)-6,7-dimethoxy-3,4-dihydro-1H-isoquinolin-2-yl]-N-(pyridin-3-yl-methyl)-acetamide;
2-[1-(3,4-Diethyl-benzyl)-6,7-dimethoxy-3,4-dihydro-1H-isoquinolin-2-yl]-N-(pyridin-4-yl-methyl)-acetamide; or
2-[1-(3,4-Dichloro-benzyl)-6,7-dimethoxy-3,4-dihydro-1H-isoquinolin-2-yl]-N-(pyridin-3-yl-methyl)-acetamide.

4. A process for the combinatorial preparation of a compound of formula (I) of claim 1, wherein $R^6$, $R^7$ and $R^9$ are hydrogen, using an Ugi-three-components-condensation reaction, comprising one pot reaction of a compound of formula (III):

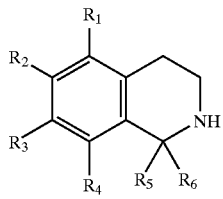

wherein $R_1$, $R_2$, $R_3$, $R_4$ and $R_5$ are as defined in formula (I) of claim 1 and $R_6$ represents hydrogen, with a compound of formula (IV):

wherein $R_7$ represents hydrogen and $R_8$ is as defined in formula (I) of claim 1, and a compound of formula (V):

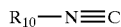

wherein $R_{10}$ is as defined in formula (I) of claim 1, optionally isolating a pharmacologically active compound, optionally resolving a racemate and, optionally converting a compound obtained into a salt.

5. A process for the preparation of a compound of formula (I) of claim 1, comprising reacting a compound of formula (III'):

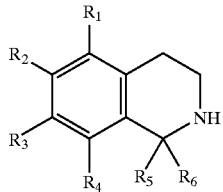

wherein the substituents $R_1$ to $R_6$ are as defined in formula (I) of claim 1, with a compound of formula (VI):

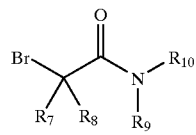

wherein $R_7$ to $R_{10}$ are as defined in formula (I) of claim 1.

6. A process for the preparation of a compound of formula (I) of claim 1, comprising reacting a compound of formula (III'):

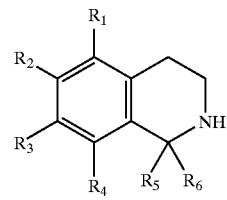

wherein the substituents $R_1$ to $R_6$ are as defined in formula (I) of claim 1, with
a) a compound of formula (IX):

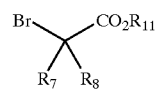

wherein $R_7$, $R_8$ and $R_{11}$ are as defined in formula (I) of claim 1,
b) cleaving an ester and reacting the acid formed with
c) a compound of formula (X):

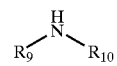

wherein the substituents $R_9$ and $R_{10}$ are as defined in formula (I) of claim 1, optionally resolving a racemate and, optionally converting a compound obtained into a salt.

7. A pharmaceutical composition comprising the compound of claim 1, or a pharmaceutically acceptable salt thereof, and a pharmaceutically acceptable carrier and/or adjuvant.

8. A method of treating a subject with a disorder which is associated with a role of orexin, comprising administering the compound of claim 1, or a pharmaceutically acceptable salt thereof.

9. A method of treating or preventing a disease or disorder where an antagonist of a human orexin receptor is required, comprising administering to a subject in need thereof an effective amount of the compound of claim 1, or a pharmaceutically acceptable salt thereof.

10. A process for the manufacture of a pharmaceutical composition which comprises a compound of claim 1, or a pharmaceutically acceptable salt thereof, as an active ingredient, comprising mixing one or more active ingredient or ingredients with a pharmaceutically acceptable excipient and/or adjuvant.

11. The method according to claim 8, wherein the disorder is obesity or a sleep disorder.

12. A compound of claim 1 that is 2-[1-(3,4-dimethoxy-benzyl)-6,7-dimethoxy-3,4-dihydro-1H-isoquinolin-2-yl]-N-(indan-1-yl) acetamide.

13. A pharmaceutical composition comprising the compound of claim 2, or a pharmaceutically acceptable salt thereof, and a pharmaceutically acceptable carrier and/or adjuvant.

14. A method of treating a subject with a disorder which is associated with a role of orexin, comprising administering the compound of claim 2, or a pharmaceutically acceptable salt thereof.

15. A method of treating or preventing a disease or disorder where an antagonist of a human orexin receptor is required, comprising administering to a subject in need thereof an effective amount of the compound of claim 2, or a pharmaceutically acceptable salt thereof.

16. A process for the manufacture of a pharmaceutical composition which comprises a compound of claim 2, or a pharmaceutically acceptable salt thereof, as an active ingredient, comprising mixing one or more active ingredient or ingredients with a pharmaceutically acceptable excipient and/or adjuvant.

17. The method of claim 14, wherein the disorder is obesity or a sleep disorder.

18. A pharmaceutical composition comprising the compound of claim 3, or a pharmaceutically acceptable salt thereof, and a pharmaceutically acceptable carrier and/or adjuvant.

19. A method of treating a subject with a disorder which is associated with a role of orexin, comprising administering the compound of claim 3, or a pharmaceutically acceptable salt thereof.

20. A method of treating or preventing a disease or disorder where an antagonist of a human orexin receptor is required, comprising administering to a subject in need thereof an effective amount of the compound of claim 3, or a pharmaceutically acceptable salt thereof.

21. A process for the manufacture of a pharmaceutical composition which comprises a compound of claim 3, or a pharmaceutically acceptable salt thereof, as an active ingredient, comprising mixing one or more active ingredient or ingredients with a pharmaceutically acceptable excipient and/or adjuvant.

22. The method of claim 19, wherein the disorder is obesity or a sleep disorder.

* * * * *